United States Patent [19]
Ayscough et al.

[11] Patent Number: 5,866,588
[45] Date of Patent: Feb. 2, 1999

[54] IMIDAZOPYRIDINE DERIVATIVES

[75] Inventors: Andrew Paul Ayscough; Christopher Mark Blackwell; Steven Launchbury; Mark Whittaker, all of Oxford, United Kingdom

[73] Assignee: British Biotech Pharmaceuticals Ltd., Oxford, United Kingdom

[21] Appl. No.: 849,980

[22] PCT Filed: Jul. 30, 1996

[86] PCT No.: PCT/GB96/01849

§ 371 Date: Jun. 20, 1997

§ 102(e) Date: Jun. 20, 1997

[87] PCT Pub. No.: WO97/06167

PCT Pub. Date: Feb. 20, 1997

[30] Foreign Application Priority Data

Apr. 5, 1995 [GB] United Kingdom .................... 9516115
Apr. 24, 1996 [GB] United Kingdom .................... 9608592

[51] Int. Cl.$^6$ .......................... C07D 471/04; A61K 31/44
[52] U.S. Cl. ............................................................ 514/303
[58] Field of Search ............................... 546/118; 514/303

[56] References Cited

U.S. PATENT DOCUMENTS 4,621,094 11/1986 Findley et al. .......................... 514/357
5,180,724 1/1993 Bowles et al. ........................... 514/248

FOREIGN PATENT DOCUMENTS 0085959 8/1983 European Pat. Off. ................. 213/55
92/14734 9/1992 WIPO ...................................... 471/4

*Primary Examiner*—Mukund J. Shah
*Assistant Examiner*—Ann M. Kessinger
*Attorney, Agent, or Firm*—Hale and Dorr LLP

[57] ABSTRACT

This invention relates to imidazopyridine derivatives with the general formula II:

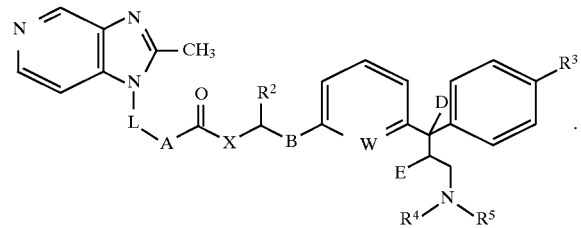

These compounds are useful as dual histamine ($H_1$) and platelet activating factor (PAF) receptor antagonists.

17 Claims, No Drawings

IMIDAZOPYRIDINE DERIVATIVES

This invention relates to compounds which are dual histamine ($H_1$) and platelet activating factor (PAF) receptor antagonists, to therapeutic compositions containing such compounds, and to methods for their preparation.

BACKGROUND TO THE INVENTION

Potent $H_1$ receptor antagonists of various structural types are known, and are useful in treating the symptoms of inflammatory conditions such as allergic rhinitis, and allergic conditions of the skin, which are mediated at least in part by the release of histamine. However, in such conditions, in which histamine release plays a causative role, there may be other mechanisms at work which are not inhibited by treatment with an $H_1$ receptor antagonist alone. For example PAF is released directly from cell membranes and mediates a range of potent and specific effects on target cells resulting in a wide variety of physiological responses, including hypotension, thrombocytopenia, bronchoconstriction, circulatory shock, increased vascular permeability (oedema/ erythema), and accumulation of inflammatory cells in the lower airways.

There is therefore a need for agents which have dual $H_1$ and PAF receptor antagonistic activity for the improved treatment of conditions mediated by histamine and PAF release. Such conditions include allergic rhinitis, sinusitis, asthma, dermatitis, psoriasis, urticaria, anaphylactic shock, conjunctivitis, pruritis, inflammatory bowel disease and colitis.

European patent specification EP-B-404797 (G. D. Searle) claims a series of PAF receptor antagonists of general formula (I)

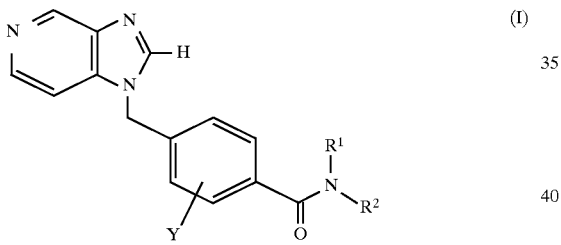

wherein Y, $R^1$ and $R^2$ are as defined in the publication itself.

International patent applications WO-A-92/03423 (British Biotechnology) and WO-A-9516687 and U.S. Pat. No. 5,180,724 (British Biotechnology) disclose series of compounds, incorporating a 2-methylimidazo[4,5-c] pyridine group which are potent antagonists of the PAF receptor.

U.S. Pat. No. 2,712,020 (Burroughs Wellcome) and European patent applications EP-A-085959 and EP-A-133534 (Wellcome Foundation) disclose compounds which are potent $H_1$ receptor antagonists.

International patent applications WO-A-92/14734 (Pfizer), WO-A-92/00293 (Schering), WO-A-89/10363 (Schering), WO-A-93/20080 (Schering), WO-93/20063 (Schering), WO-A-93/23400 (Schering), WO-A-93/02081 (Schering), WO-A-94/08581 (Toray), European patent applications EP-A-515158 (Schering), EP-A-463873 (Sankyo), EP-A-549364 (Sankyo), EP-A-577957 (Uriach) and Japanese patent application published under no 4-226993 (Yoshitomi) all disclose compounds which possess both histamine ($H_1$) and PAF receptor antagonist activity.

BRIEF DESCRIPTION OF THE INVENTION

The invention makes available a class of compounds with some of the structural features of the potent PAF receptor antagonists of WO-A-92/03423 and U.S. Pat. No. 5,180,724, and structural features of $H_1$ receptor antagonists of for example U.S. Pat. No. 2,712,020, united in a single molecule in such a way as to provide a desirable balance of $H_1$ and PAF receptor antagonist activity. Furthermore, it has been shown that, in such compounds the structural features of the histamine fragment are also important for providing high affinity for the PAF receptor.

DETAILED DESCRIPTION OF THE INVENTION

According to the present invention there is provided a compound of formula (II)

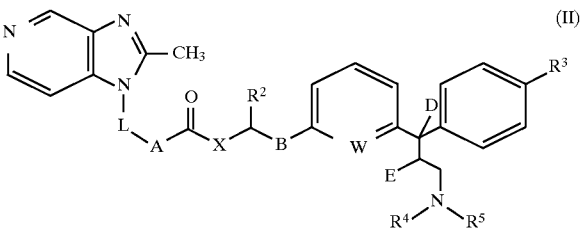

wherein:

L and A are such that (i) L represents an unbranched saturated or unsaturated divalent hydrocarbon chain having up to 6 carbon atoms and A represents a bond, or (ii) L represents a bond or —$CH_2$— and A represents a divalent 1,4-phenylene group which may be substituted by $C_1$–$C_6$ alkyl, $C_2$–$C_6$ alkenyl, cyano, halogen or $C_1$–$C_6$ alkoxy;

X represents (a) —O—; or (b) —N($R^1$)— wherein $R^1$ represents hydrogen, $C_1$–$C_6$ alkyl, $C_2$–$C_6$ alkenyl, $C_2$–$C_6$ alkynyl, $C_3$–$C_8$ cycloalkyl or non-aromatic 5 to 7 membered heterocyclyl, any of which which may be substituted with one or more $C_1$–$C_6$ alkyl, —(C=O) O($C_1$–$C_6$ alkyl), —COOH, or phenyl groups;

$R^2$ represents hydrogen, $C_1$–$C_6$ alkyl, $C_2$–$C_6$ alkenyl, $C_2$–$C_6$ alkynyl, $C_3$–$C_8$ cycloalkyl or non-aromatic 5 to 7 membered heterocyclyl which may be substituted with one or more $C_1$–$C_6$ alkyl, —(C=O)O($C_1$–$C_6$ alkyl), —COOH, or phenyl groups;

B represents a bond, or a straight or branched saturated or unsaturated divalent hydrocarbon chain of up to 3 carbon atoms;

$R^3$ represents hydrogen, $C_1$–$C_4$ alkyl, halogen, cyano, trifluoromethyl or $C_1$–$C_4$ alkoxy;

W represents —N= or —C=;

D represents hydrogen or a hydroxyl and E represents hydrogen, or D and E taken together represent —C=C—;

$R^4$ and $R^5$ are independently $C_1$–$C_6$ alkyl or together with the nitrogen atom to which they are attached form a non-aromatic 5–7 membered heterocyclic ring, which may contain one or more heteroatoms other than the nitrogen to which $R^3$ and $R^4$ are attached;

or a pharmaceutically or veterinarily acceptable acid addition salt, solvate or hydrate thereof.

Hereafter in this specification the term "compound" includes "salt", "solvate", or "hydrate" unless the context requires otherwise.

As used herein the term "halogen" or its abbreviation "halo" means fluoro, chloro, bromo or iodo.

As used herein the term "$C_1$–$C_6$ alkyl" or "saturated hydrocarbon chain having up to 6 carbon atoms" refers to a straight or branched chain alkyl moiety having from 1 to 6 carbon atoms, including for example, methyl, ethyl, propyl, isopropyl, butyl, isobutyl, sec-butyl, tert-butyl, pentyl, neopentyl and hexyl. A divalent saturated hydrocarbon chain having up to 6 carbon atoms is such an alkyl moiety having two unsatisfied valencies, including, for example, 1,2-ethylene, 1,3-propylene, 1,4-butylene, 1,5-pentylene, and 1,6-hexylene.

The term "$C_2$–$C_6$ alkenyl" refers to a straight or branched chain alkenyl moiety having from 2 to 6 carbon atoms and having in addition one double bond of either cis or trans stereochemistry where applicable. This term would include, for example, vinyl, 1-propenyl, 1- and 2-butenyl and 2-methyl-2-propenyl.

As used herein the term "$C_2$–$C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

The term "unsaturated hydrocarbon chain of up to 6 carbon atoms" refers to a straight or branched chain $C_2$–$C_6$ alkenyl or $C_2$–$C_6$ alkynyl moiety, and a divalent unsaturated hydrocarbon chain having up to 6 carbon atoms is a $C_2$–$C_6$ alkenyl or $C_2$–$C_6$ alkynyl moiety having two unsatisfied valencies, including, for example, 1,2-ethenylene, 1,3-prop-1-enylene, 1,3-prop-2-enylene, 1,2-ethynylene, 1,3-prop-1-ynylene, 1,3-prop-2-ynylene, As used herein, the term "$C_3$–$C_8$ cycloalkyl" refers to an alicyclic group having from 3 to 8 carbon atoms. Illustrative of such cycloalkyl groups are cyclopropyl, cyclobutyl, cyclopentyl and cyclohexyl.

As used herein, the term "non-aromatic 5 to 7 membered heterocyclyl" refers to a non-aromatic monocyclic heterocyclic group having from 5 to 7 ring atoms wherein the heteroatom(s) are selected from O, S and N. Illustrative of such are morpholinyl, thiomorpholinyl, tetrahydrofuranyl, dihydrofuranyl, tetrahydrothienyl, dihydrothienyl, piperidinyl, pyrrolidinyl, pyrrolinyl, dioxolanyl, oxathiolanyl, imidazolinyl, imidazolidinyl, pyrazolinyl, pyrazolidinyl, pyranyl, dioxanyl, dithianyl, oxathianyl, and piperazinyl.

As used herein, the term "divalent phenylene" group means a benzene ring in which two of the ring carbons have unsatisfied valencies.

Compounds of this invention may contain one or more asymmetric carbon atoms, giving rise to either a pair of enantiomers (in the case of one asymmetric carbon atom), or to diastereoisomers, each of which consists of two enantiomers (in the case of more than one asymmetric carbon atom), with the appropriate R or S stereochemistry at each chiral centre. The invention includes all such enantiomers and diastereoisomers, and mixtures thereof.

The term "pharmaceutically or veterinarily acceptable acid addition salt" refers to a salt prepared by contacting a compound of formula (I) with an acid whose anion is generally considered suitable for human or animal consumption.

Examples of pharmaceutically and/or veterinarily acceptable acid addition salts include the hydrochloride, sulphate, phosphate, acetate, propionate, lactate, maleate, succinate, citrate, mesylate, benzoate, tosylate and tartrate salts.

Compounds of formula (II) include those in which, independently or in any compatible combination:

L and A are such that (i) L represents a $C_1$–$C_6$ alkylene group and A represents a bond, or (ii) L represents a bond or —$CH_2$— and A represents a divalent 1,4-phenylene group which may be substituted by $C_1$–$C_6$ alkyl, halogen or $C_1$–$C_6$ alkoxy. An example of case (i) is where L is 1,2-ethylene or 1,3-propylene and A is a bond. Examples of case (ii) include those where L is a bond or, preferably, —$CH_2$—, and A is 1,4-phenylene, 3-fluoro-1,4-phenylene or 3-methoxy-1,4-phenylene.

X represents (a) —O—; or (b) —N($R^1$)— wherein $R^1$ represents hydrogen, cyclopropyl, cyclopentyl, cyclohexyl, 3,5-dimethylcyclohex-1-yl, methyl, ethyl, 3-methylbut-1-yl, n-butyl, iso-butyl, sec-butyl, tert-butyl, n-propyl, isopropyl, n-pentyl, n-nonyl, 2-ethylcarboxylate-3-methylbut-1-yl, benzyl, or tetrahydropyranyl. Preferably X is —N($R^1$)— where $R^1$ is cyclohexyl, methyl or ethyl.

$R^2$ represents hydrogen or $C_1$–$C_6$ alkyl, eg methyl. Preferably $R^2$ is hydrogen.

B represents a straight saturated or mono-unsaturated divalent hydrocarbon chain having 2 or 3 carbon atoms eg —$CH_2CH_2$—, —$CH_2CH_2CH_2$—, —CH=CH—, —$CH_2$CH=CH—, or —CH=CH$CH_2$—. In the case where B is a straight chain $C_2$ or $C_3$ divalent alkenyl group, the double bond preferrably has the trans stereoconfiguration. Preferred is —CH=CH— (trans).

$R^3$ represents hydrogen, $C_1$–$C_4$ alkyl eg methyl, or halogen eg chloro. Preferred is methyl.

W represents —N=;

D and E taken together represent —C=C—;

$R^4$ and $R^5$ are independently $C_1$–$C_6$ alkyl or together represent a group —($CH_2$)$_m$— wherein m is 5, 6 or, preferably, 4;

A compound of the present invention which is presently particularly preferred for its combination of PAF and $H_1$ receptor antagonistic activity and its activity following oral administration is N-cyclohexyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, and its salts hydrates and solvates.

Another preferred compound of the invention is N-ethyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, and its salts hydrates and solvates.

Additional specific compounds of the invention are:

4-(1H-2-Methylimidazo[4,5-c]pyridin-1-ylmethyl)benzoic acid 3-[6-(3-pyrrolidin-1-yl-1-{4-tolyl}-prop-1E-enyl)-pyridin-2-yl]prop-2E-enyl ester, 4-(1H-2-Methylimidazo[4,5-c]pyridin-1-ylmethyl)benzoic acid 3-[6-(3-pyrrolidin-1-yl-1-{4-tolyl}-prop-1E-enyl)-pyridin-2-yl]propyl ester, N-Methyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, 4-(1H-2-Methylimidazo[4,5-c]pyridin-1-ylmethyl)-N-{3-[6-(3-pyrrolidino-1-{4-tolyl}-prop-1E-enyl)-pyridin-2-yl]-prop-2E-enyl}-benzamide, N-(3-Methyl-but-1-yl)-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-iso-Butyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Cyclopentyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-(R,S) sec-Butyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-tert-Butyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-3,5-Dimethylcyclohexyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-iso-Propyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, (S)-4-Methyl-2-([4-(1H-2-methylimidazo[4,5-c]pyridin-1-ylmethyl)-benzoyl]-{3-[6-(3-pyrrolidin-1-yl-1-{4-tolyl}-prop-1E-enyl)-pyridin-2-yl]-prop-2E-enyl}-amino)-pentanoic acid ethyl ester, N-Benzyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Propyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Cyclohexyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-propyl}-benzamide, N-Cyclopropyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, (R,S)-4-(1H-2-Methylimidazo[4,5-c]pyridin-1-ylmethyl) benzoic acid 3-[6-(3-pyrrolidin-1-yl-1-{4-tolyl}-prop-1E-enyl)-pyridin-2-yl]but-3E-en-2-yl ester, N-Cyclohexyl-4-(1H-2-methylimidazo[4,5-c]pyridin-1-ylmethyl)-N-{3-[6-(3-pyrrolidin-1-yl-1-{4-p-chlorophenyl}-prop-1E-enyl)-pyridin-2-yl]-prop-2E-enyl}-benzamide, N-4-Tetrahydropyranyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Butyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Pentyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Nonyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Hexyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Methyl-4-(1H-2-methylimidazo[4,5-c]pyridin-1-yl)-N-{3-[6-(3-pyrrolidin-1-yl-1-{4-tolyl}-prop-1E-enyl)-pyridin-2-yl]-prop-2E-enyl)-benzamide, (R,S)-4-(1H-2-Methylimidazo[4,5-c]pyridin-1-ylmethyl) benzoic acid (E)-1-[6-( 3-pyrrolidin-1-yl-1-{4-tolyl}-prop-1E-enyl)-pyridin-2-yl]hex-1E-en-3-yl ester, N-Ethyl-N-{3-[6-(3-pyrrolidin-1-yl-1-{4-tolyl}-prop-1E-enyl)-pyridin-2-yl]-prop-2E-enyl}-3-(1H-2-methylimidazo[4,5-c]pyridin-1-yl)-propylamide, N-Cyclohexyl-N-{3-[6-(3-pyrrolidin-1-yl-1-{4-tolyl}-prop-1E-enyl)-pyridin-2-yl]-prop-2E-enyl}-4-(1H-2-methylimidazo[4,5-c]pyridin-1-yl)-butylamide N-Cyclohexyl-3-fluoro-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Cyclohexyl-3-methoxy-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, and their salts, hydrates and solvates.

Compounds of the invention of general formula (II) may be prepared by standard techniques of organic synthesis.

Route 1

Compounds of the invention in which X represents —O— may be prepared by esterification of an acid of formula (III) with an alcohol of formula (IV);

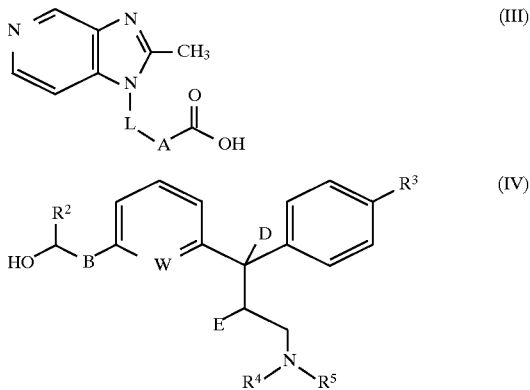

wherein L, A, $R^2$, B, W, D, E, $R^3$, $R^4$ and $R^5$ are as defined in formula (II). The esterification may be performed in the presence of a carbodiimide condensing agent such as (N)-3-dimethylaminopropyl-N'-ethyl-carbodiimide. Alternatively, an activated derivative of the acid (III) may be employed for the esterification, such as the acid chloride or pentafluorophenyl ester.

Route 2

Compounds of the invention in which X represents —N($R^1$)— may be prepared by amidation of an acid of formula (III) with an amine of formula (V);

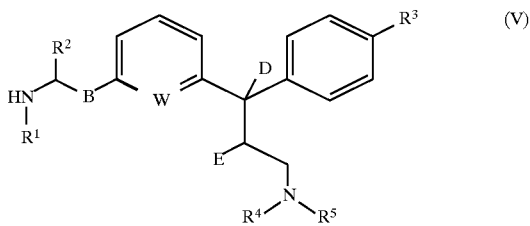

wherein $R^1$, $R^2$, B, W, D, E, $R^3$, $R^4$ and $R^5$ are as defined in formula (II). The amidation may be performed in the presence of a carbodiimide condensing agent such as (N)-3-dimethylaminopropyl-N'-ethyl-carbodiimide or using an activated derivative of the acid (III) as for the esterification. The reaction may be facilitated by the addition of for example 1-hydroxybenzotriazole or 1-hydroxy-7-azabenzotriazole.

Route 3

Compounds of the invention in which D and E taken together represent —C=C— may be prepared by the reaction between a ketone of formula (VI) and a Wittig reagent formed by the treatment of a phosphonium salt of formula (VII) with a strong base such as n-butyllithium;

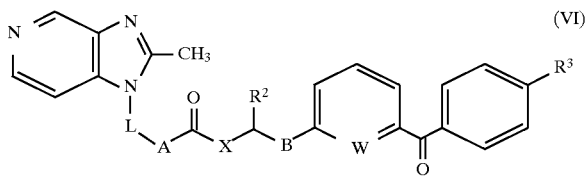

(VI)

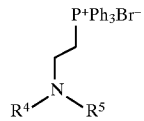

(VII)

wherein L, A, R², B, X, W, R³, R⁴ and R⁵ are as defined in formula (II). This reaction may be performed in the presence of a suitable solvent such as toluene.

Route 4

Compounds of the invention in which B represents an alkenyl or alkynyl group may be prepared by the palladium catalysed cross coupling reaction between a halide of formula (VIII) and an unsaturated compound of formula (IX);

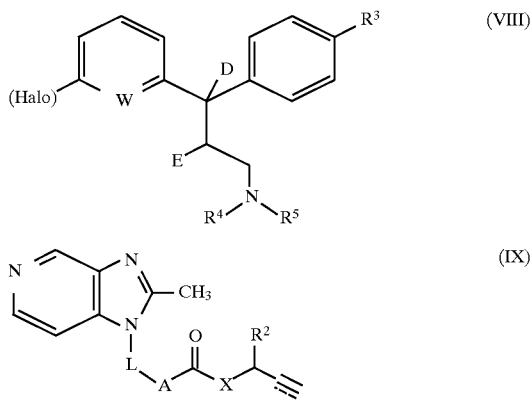

(VIII)

(IX)

wherein L, A, R², X, W, D, E, R³, R⁴ and R⁵ are as defined in formula (II) and "halo" is preferably iodo or bromo. Preferred catalysts are palladium(II) catalysts such as Pd(OAc)₂, Pd(OAc)₂/PPh₃ etc. The coupling reaction may be carried out in a suitable solvent such as DMF or dimethoxyethane and at elevated temperatures of about 80°–160° C.

Route 5

Compounds of the invention of formula (II) may also be prepared by a process comprising reaction of a diamino compound of formula (X), with acetic acid or a derivative thereof;

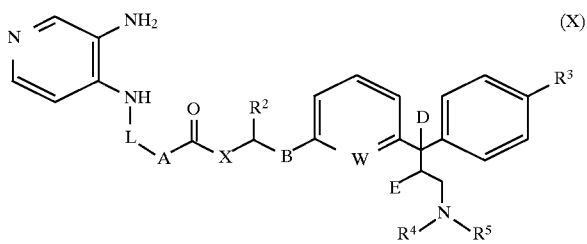

(X)

wherein L, A, X, R², B, W, D, E, R³, R⁴ and R⁵ are as described in formula (II). This reaction is analogous to that described previously in WO-A-92/03423.

The starting carboxylic acids of formula (III) may be prepared by either acid or base hydrolysis of the corresponding esters of formula (XI) to provide an acid or base salt respectively;

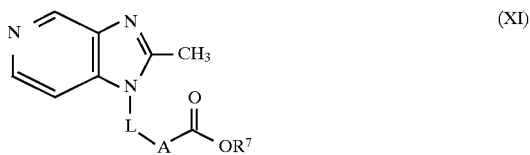

(XI)

wherein L and A are as defined in formula (II) and R⁷ is C₁–C₆ alkyl or benzyl. Esters of formula (XI) may be prepared as described in the literature eg WO-A-93/16075 (British Biotechnology), WO-A-90/11280 (Pfizer) and WO-A-92/14734 (Pfizer). The alcohols of formula (IV) may be prepared by the reduction of esters of formula (XII) in the presence of a reducing agent such as diisobutylaluminium hydride;

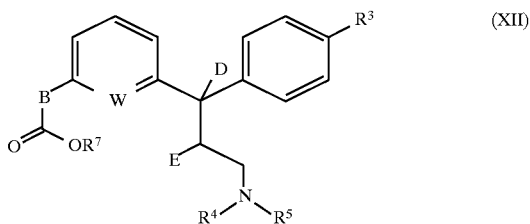

(XII)

wherein B, W, D, E, R³, R⁴ and R⁵ are as defined in formula (II) and R⁷ is as defined for formula (XI). Esters of formula (XII) may be prepared using routes analogous to those described in the literature eg EP-085959-A2 (Wellcome).

The amines of formula (V) may be prepared by the oxidation of alcohols of formula (IV) to aldehydes or ketones of formula (XIII) with an oxidizing agent, such as manganese dioxide, followed by reductive amination with an amine of formula (XIV);

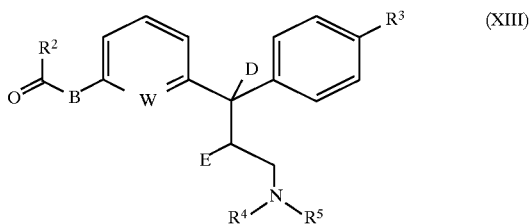

(XIII)

(XIV)

wherein R¹, R², B, W, D, E, R³, R⁴ and R⁵ are as defined for formula (II). The reductive amination may be facilitated by a reducing agent such as sodium borohydride in a suitable solvent, such as methanol or in the presence of a palladium catalyst under an atmosphere of hydrogen.

As mentioned above, the invention makes available a class of compounds having a desirable balance of H₁ and PAF antagonist activity.

Accordingly in another aspect, this invention concerns:

(i) a method of management (by which is meant treatment or prophylaxis) of diseases or conditions mediated by histamine and/or PAF in mammals, in particular in humans, which method comprises administering to the mammal an effective amount of a compound as defined with respect to formula (II) above, or a pharmaceutically acceptable salt thereof; and (ii) a compound as defined with respect to formula (II) for use in human or veterinary medicine, particularly in the management (by which is meant treatment or prophylaxis) of diseases or conditions mediated by histamine and/or PAF; and (iii) the use of a compound as defined with respect to formula (II) in the preparation of an agent for the management (by which is meant treatment or prophylaxis) of diseases or conditions mediated by histamine and/or PAF.

Diseases or conditions mediated by histamine and/or PAF, but which probably include contributions from both agents, include hypotension, thrombocytopenia, bronchoconstriction, circulatory shock, increased vascular permeability (oedema/erythema), allergic rhinitis, sinusitis, asthma, dermatitis, psoriasis, urticaria, anaphylactic shock, conjunctivitis, pruritis, inflammatory bowel disease and colitis.

According to a further aspect of the invention there is provided a pharmaceutical or veterinary formulation comprising a compound of general formula (II) and a pharmaceutically and/or veterinarily acceptable carrier. One or more compounds of general formula (II) may be present in association with one or more non-toxic pharmaceutically and/or veterinarily acceptable carriers and/or diluents and/or adjuvants and if desired other active ingredients. The pharmaceutical compositions containing compounds of general formula (II) may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occuring phosphatide, for example lecithin, or condensation products of an alkylene oxide with fatty acids for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical application to the skin compounds of the invention may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

For topical applications to the eye, compounds of the invention may be made up into a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine, and thickening agents such as hypromellose may also be included.

Compounds of the invention may be administered parenterally in a sterile medium. The drug depending on the vehicle and concentration used, can either be suspended or dissolved in the vehicle. Advantageously, adjuvants such as a local anaesthetic, preservative and buffering agents can be dissolved in the vehicle.

Compounds of the invention may be used for the treatment of the respiratory tract by nasal or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Dosage levels of the order of from about 0.1 mg to about 140 mg per kilogram of body weight per day are useful in the treatment of the above-indicated conditions (about 0.5 mg to about 7 g per patient per day). For example, inflammation may be effectively treated by the administration of from about 0.01 to 50 mg of the compound per kilogram of body weight per day (about 1.0 mg to about 3.5 g per patient per day). The dosage employed for the topical administration will, of course, depend on the size of the area being treated. For the eyes each dose will be typically in the range from 0.1 to 10 mg of the drug.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples illustrate the invention, but are not intended to limit the scope in any way. The following abbreviations have been used in the examples:

DCM—Dichloromethane
DMF—Dimethylformamide
HOAt—1-Hydroxy-7-azabenzotriazole
DIBAL—Diisobutylaluminium hydride
EDC—N-(3-dimethylaminopropyl)-N'-ethylcarbodiimide hydrochloride
DMAP—N,N-Dimethylaminopyridine
HCI—Hydrochloric acid Anhydrous magnesium sulphate and sodium sulphate were used as drying agents. Column chromatography was performed with flash grade silica gel. $^1$H-NMR and $^{13}$C-NMR were recorded either on a Bruker AC-250 spectrometer at 250 MHz and 62.5 MHz respectively or on a Bruker AMX-500 spectrometer at 500 MHz and 125.72 MHz respectively. CDCl$_3$ or d$_4$-methanol (MeOD) were used as a solvent and internal reference and spectra are reported as δ ppm from TMS.

EXAMPLE 1

4-(1H-2-Methylimidazo[4,5-c]pyridin-1-ylmethyl) benzoic acid 3-[6-(3-pyrrolidin-1-yl-1-{4-tolyl}-prop-1E-enyl)-pyridin-2-yl]prop-2E-enyl ester

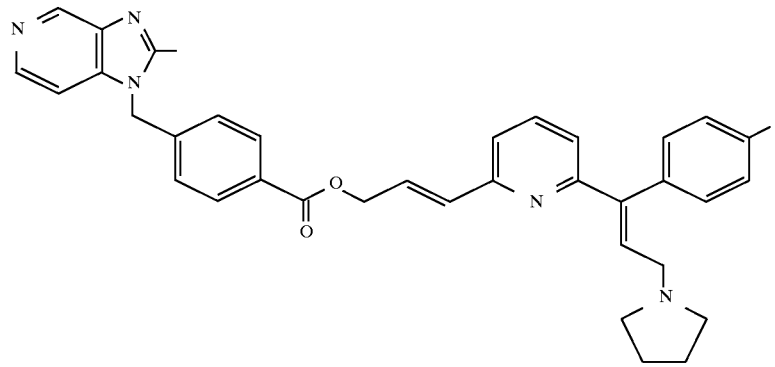

(a) Methyl-(E)-3-(6-[3-pyrrolidin-1-yl-{4-tolyl}-prop-1E-enyl]-pyridin-2-yl)-acrylate.

A solution of (E)-3-(6-[3-pyrrolidin-1-yl-{4-tolyl}-prop-1E-enyl]-pyridin-2-yl)-acrylic acid (2.04 g, 5.9 mmol) in methanol (50 ml) was treated with concentrated HCI (10 ml) and stirred at room temperature for 6 days. The reaction was neutralised with a saturated solution of sodium hydrogen carbonate and solvent removed under reduced pressure.

DCM was added to the residue and inorganic solids removed by filtration. Concentration of the filtrate under reduced pressure yielded methyl-(E)-3-(6-[3-pyrrolidin-1-yl-{4-tolyl}-prop-1E-enyl]-pyridin-2-yl)-acrylate as a pink foam (1.98 g, 93%). ¹H-NMR; δ (CDCl₃), 7.70 (1H, d, J=15.7 Hz), 7.57 (1H, t, J=7.7 Hz), 7.30 (1H, t, J=7.6 Hz), 7.25 (2H, d, J=8.3 Hz), 7.17 (1H, d, J=7.2 Hz), 7.10 (2H, dt, J=8.2, 1.8 Hz), 6.96 (1H, d, J=15.6 Hz), 6.93 (1H, d, J=7.9 Hz), 3.83 (3H, s), 3.65 (2H, bs), 2.85 (4H, bm), 2.41 (3H, s) and 2.04 (4H, bm).

(b) 3-(6-[3-Pyrrolidino-1-{4-tolyl}-prop-1E-enyl]-pyridin-2-yl)-prop-2E-en-1-ol.

A solution of methyl-(E)-3-(6-[3-pyrrolidin-1-yl-{4-tolyl}-prop-1E-enyl]-pyridin-2-yl)acrylate (1.98 g, 5.47 mmol) in dry THF (100 ml) was cooled to −78° C. and treated under an inert atmosphere with a solution of DIBAL (1M in toluene, 16.4 ml, 16.4 mmol). After stirring for 3 hours at −78° C. more DIBAL was added (11 ml, 11 mmol) and the reaction allowed to warm to room temperature. Following a total reaction time of 24 hours the reaction was quenched with water (0.5 ml). The reaction mixture was partitioned between DCM and water. The aqueous layer was separated, acidified (20 ml, 1M HCl) and extracted with DCM. The organic extracts were combined, dried over sodium sulphate, filtered and concentrated under reduced pressure to yield 3-(6-[3-pyrrolidino-1-{4-tolyl}-prop-1E-enyl]-pyridin-2-yl)-prop-2E-en-1-ol as an off white solid (1.69 g, 93%). ¹H-NMR; δ (CDCl₃), 7.40 (1 H, t, J=7.9 Hz), 7.19 (2H, d, J=7.8 Hz), 7.16 (1H, t, J=7.3 Hz), 7.08 (1H, d, J=7.7 Hz), 7.01 (2H, d, J=7.9 Hz), 6.96 (1H, dt, J=15.7, 5.0 Hz), 6.69 (1H, d, J=15.7 Hz), 6.66 (1H, d, J=7.8 Hz), 4.36 (2H, dd, J=5.0, 1.4 Hz), 3.58 (2H, d, J=7.2 Hz), 3.04 (4H, bs), 2.36 (3H, s) and 1.96 (4H, bs); ¹³C-NMR; δ (CDCl₃), 155.8, 154.7, 146.6, 137.9, 136.9, 134.8, 133.8, 129.5, 129.4, 129.3, 129.1, 121.1, 120.8, 62.6, 53.0, 52.8, 29.6, 23.4, 23.4 and 21.2.

(c) 4-(1H-2-Methylimidazo[4,5-c]pyridin-1-ylmethyl)benzoic acid 3-[6-(3-pyrrolidin-1-yl-1-{4-tolyl}-prop-1E-enyl)-pyridin-2-yl]prop-2E-enyl ester.

A solution of 4-(1H-2-methylimidazo[4,5-c]pyridin-1-ylmethyl)}benzoic acid sodium salt (310 mg, 1.08 mmol), 3-(6-[3-pyrrolidino-1-{4-tolyl}-prop-1E-enyl]-pyridin-2-yl)-prop-2E-en-1-ol (300 mg, 0.90 mmol) and EDC (275 mg, 1.44 mmol) in DCM (10 ml) was treated with DMAP (5 mg) and stirred at room temperature for 96 hours. The solution was concentrated under reduced pressure and purified by column chromatography on silica-gel. Product was eluted with 5% methanol/DCM. Product containing fractions were combined and solvent removed to yield 4-(1H-2-methylimidazo[4,5-c]pyridin-1-ylmethyl)benzoic acid 3-[6-(3-pyrrolidin-1-yl-1-{4-tolyl}-prop-1E-enyl)-pyridin-2-yl] prop-2E-enyl ester as a white foam (72 mg, 15%). ¹H-NMR; δ (CDCl₃), 9.03 (1H, s), 8.37 (1H, d, J=5.5 Hz), 8.08 (2H, d, J=8.4 Hz), 7.44 (1H, t, J=7.7 Hz), 7.21 (2H, d, J=7.9 Hz), 7.20 (1H, t, J=7.0 Hz), 7.15 (1H, d, J=5.8 Hz), 7.13 (2H, d, J=8.4 Hz), 7.10 (1H, d, J=9.0 Hz), 7.07 (2H, d, J=8.0 Hz), 7.01 (1H, dt, J=15.5, 6.0 Hz), 6.78 (1H, d, J=15.7 Hz), 6.71 (1H, d, J=7.7 Hz), 5.39 (2H, s), 5.03 (2H, d, J=1.4 Hz), 3.30 (2H, d, J=7.0 Hz), 2.67 (4H, br s), 2.60 (3H, s), 2.40 (3H, s) and 1.82 (4H, bs); ¹³C-NMR; δ (CDCl₃), 165.5, 157.1, 153.5, 153.4, 142.2, 142.0, 140.3, 139.9, 139.8, 137.2, 136.8, 135.0, 132.9, 130.7, 130.3, 129.6, 129.2, 127.8, 126.2, 121.3, 120.5, 104.8, 65.0, 54.4, 53.9, 47.1, 23.4, 21.3 and 14.0.

EXAMPLE 2

4-(1H-2-Methylimidazo[4,5-c]pyridin-1-ylmethyl)benzoic acid 3-[6-(3-pyrrolidin-1-yl-1-{4-tolyl}-prop-1E-enyl)-pyridin-2-yl]propyl ester

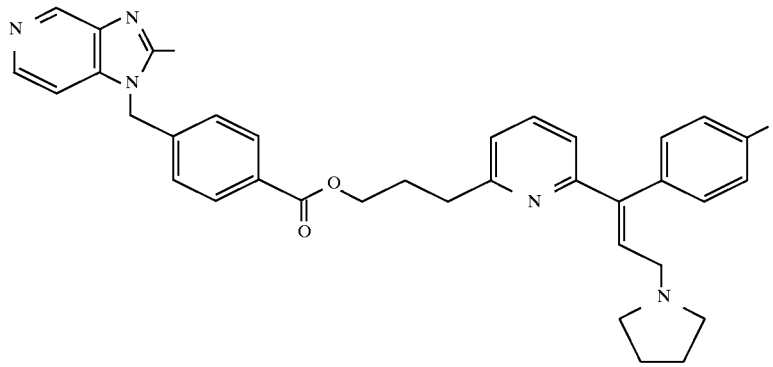

(a) Methyl-3-(6-[3-pyrrolidin-1-yl-{4-tolyl}-prop-1E-enyl]-pyridin-2-yl)-propanoate.

Sodium borohydride (629 mg, 16.56 mmol) and tellurium (898 mg, 7.04 mmol) were heated in degassed ethanol (30 ml) under an inert atmosphere at 80° C. for 1 hour. The resulting suspension was cooled to room temperature, treated with degassed ammonium chloride followed by a solution of methyl-(E)-3-(6-[3-pyrrolidin-1-yl-{4-tolyl}-prop-1E-enyl]-pyridin-2-yl)-acrylate (1.0 g, 2.76 mmol) in ethanol (10 ml). The reaction was stirred at room temperature for 18 hours under an inert atmosphere. The reaction was opened to the air, stirred for 2 hours and then filtered through a pad of kieselguhr. The filtrate was concentrated under reduced pressure to leave a pink solid. The solid was triturated with DCM (×3). The combined washings were filtered and solvent removed under reduced pressure to yield methyl-(E)-3-(6-[3-pyrrolidin-1-yl-{4-tolyl}-prop-1E-enyl]-pyridin-2-yl)-propanoate as a pink foam (1.084 g, contaminated with some ethyl ester). ¹H-NMR; δ (CDCl₃), 7.47 (1H, t, J=7.6 Hz), 7.26 (2H, d, J=6.9 Hz), 7.00 (4H, m), 6.72 (1H, d, J=7.2 Hz), 3.78 (2H, d, J=6.8 Hz), 3.70 (3H, s), 3.30 (4H, bm), 3.18 (2H, t, J=8.2 Hz), 2.88 (2H, t, J=7.2 Hz), 2.45 (3H, s) and 2.14 (4H, bm).

(b) (E)-3-(6-[3-Pyrrolidino-1-{4-tolyl}-prop-1-enyl]-pyridin-2-yl)-propanol.

A solution of methyl-(E)-3-(6-[3-pyrrolidin-1-yl-{4-tolyl}-prop-1-enyl]-pyridin-2-yl)-propanoate (206 mg, 0.55 mmol, mixture of methyl and ethyl esters) in THF (5 ml) was cooled to −78° C. and treated under an inert atmosphere with DIBAL (1.65 ml of 1.0M solution in toluene, 1.65 mmol). The reaction was stirred for 4 hours at −78° C. and allowed to warm to room temperature. The reaction was quenched with water (2 ml) and the product extracted into DCM (×3). The organic extracts were combined, dried over magnesium sulphate, filtered and concentrated under reduced pressure to yield (E)-3-(6-[3-pyrrolidino-1-{4-tolyl}-prop-1-enyl]-pyridin-2-yl)-propanol as a pale brown gum (137 mg, 74%). $^1$H-NMR; δ (CDCl$_3$), 7.42 (1H, t, J=8.3 Hz), 7.20 (2H, d, J=7.8 Hz), 7.09 (2H, d, J=9.6 Hz), 6.98 (2H, m), 6.73 (1H, d, J=7.6 Hz), 3.70 (2H, t, J=7.3 Hz), 3.18 (2H, d, J=6.9 Hz), 2.97 (2H, t, J=7.3 Hz), 2.52 (4H, bm), 2.39 (3H, s), 2.00 (2H, m) and 1.77 (4H, bm).

(c) 4-(1H-2-Methylimidazo[4,5-c]pyridin-1-ylmethyl) benzoic acid 3-[6-(3-pyrrolidin-1-yl-1-{4-tolyl}-prop-1E-enyl)-pyridin-2-yl]propyl ester.

A solution of 4-(1H-2-methylimidazo[4,5-c]pyridin-1-ylmethyl)}benzoic acid sodium salt (551 mg, 1.52 mmol), (E)-3-(6-[3-pyrrolidino-1-{4-tolyl}-prop-1E-enyl]-pyridin-2-yl)-propanol (341 mg, 1.02 mmol) and N-(3-dimethylaminopropyl)-N'-ethylcarbodiimide hydrochloride (311 mg, 1.62 mmol) in DCM (10 ml) was treated with dimethylaminopyridine (5 mg) and stirred at room temperature for 96 hours. The reaction mixture was partitioned between DCM and saturated sodium bicarbonate solution. The organic layer was washed with brine, dried over magnesium sulphate, filtered and concentrated under reduced pressure. The product was purified by column chromatography on silica-gel eluting with 10% methanol/DCM. Product containing fractions were combined and solvent removed to yield 4-(1H-2-methylimidazo[4,5-c]pyridin-1-ylmethyl)benzoic acid 3-[6-(3-pyrrolidin-1-yl-1-{4-tolyl}-prop-1E-enyl)-pyridin-2-yl]propyl ester as a white foam (138 mg, 23%). $^1$H-NMR; δ (CDCl$_3$), 9.00 (1H, s), 8.33 (1H, d, J=5.5 Hz), 7.96 (2H, d, J=8.3 Hz), 7.35 (1H, t, J=7.7 Hz), 7.18 (2H, d, J=7.8 Hz), 7.10 (6H, m), 6.95 (1H, d, J=7.6 Hz), 6.64 (1H, d, J=7.7 Hz), 5.37 (2H, s), 4.36 (2H, t, J=6.5 Hz), 3.27 (2H, d, J=7.0 Hz), 2.90 (2H, t, J=7.3 Hz), 2.65 (4H, m), 2.57 (3H, s), 2.36 (3H, s), 2.25 (2H, m) and 1.78 (4H, m); $^{13}$C-NMR; δ (CDCl$_3$), 165.8, 160.0, 156.9, 153.5, 142.1, 141.9, 140.3, 139.8, 139.7, 137.1, 136.5, 135.1, 130.5, 130.5, 130.4, 129.6, 129.2, 126.1, 121.2, 119.8, 104.8, 64.8, 54.4, 53.8, 47.1, 34.6, 31.2, 28.0, 23.4, 21.2 and 14.0.

EXAMPLE 3

N-Methyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide

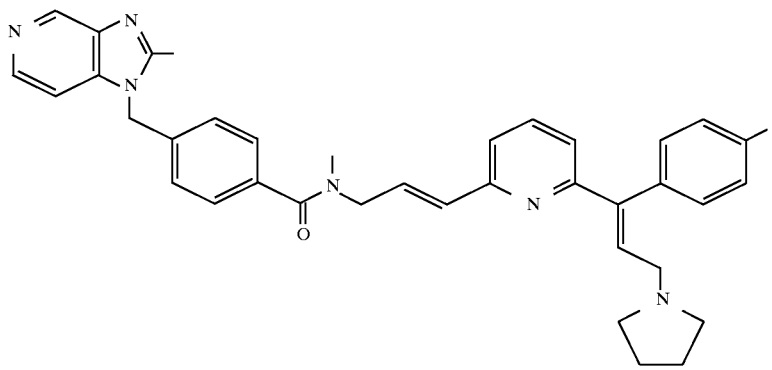

(a) 3-(6-[3-Pyrrolidino-1-{4-tolyl}-prop-1E-enyl]-pyridin-2-yl)-prop-2E-enal.

A solution of 3-(6-[3-pyrrolidino-1-{4-tolyl}-prop-1E-enyl]-pyridin-2-yl)-prop-2E-en-1-ol (1.00 g, 2.99 mmol) in DCM (20 ml) was treated portionwise with manganese dioxide (4 g, 46 mmol). The reaction mixture was stirred vigorously for 3 hours before filtration through a glass fiber pad. The filtrate was concentrated under reduced pressure to yield 3-(6-[3-pyrrolidino-1-{4-tolyl}-prop-1E-enyl]-pyridin-2-yl)-prop-2E-enal as a brown solid (0.924 g, 93%). $^1$H-NMR; δ (CDCl$_3$), 9.87 (1H, d, J=9.5 Hz), 7.55 (1H, t, J=7.5 Hz), 7.50 (1H, d, J=15.5 Hz), 7.33 (1H, d, J=8.0 Hz), 7.21 (2H, d, J=8.5 Hz), 7.18–7.13 (2H, m), 7.08 (2H, d, J=8.5 Hz), 6.92 (1H, d, J=9.5 Hz), 3.27 (2H, d, J=9.5 Hz), 2.62–2.27 (4H, m), 2.39 (3H, s) and 1.81–1.77 (4H, m).

(b) Methyl-{3-(6-[3-pyrrolidino-1-{4-tolyl}-prop-1E-enyl]-pyridin-2-yl)-prop-2E-enyl}-amine.

A solution of 3-(6-[3-pyrrolidino-1-{4-tolyl}-prop-1E-enyl]-pyridin-2-yl)-prop-2E-enal (230 mg, 0.69 mmol) in DCM (10 ml) was treated with magnesium sulphate (1.25 g) and methylamine (380 μl of a 2M solution in THF, 0.76 mmol). The reaction was stirred in the absence of light for 18 hours, filtered and concentrated under reduced pressure to provide the imine as a brown oil. The residue was resuspended in dry methanol (10 ml), cooled in an ice-salt bath and treated under an inert atmosphere with sodium borohydride (30.6 mg, 0.81 mmol). The reaction was stirred for 2 hours and solvent removed under reduced pressure. The residue was taken up in DCM (10 ml) and washed with brine. The organics were dried over magnesium sulphate, filtered and concentrated to yield methyl-{3-(6-[3-pyrrolidino-1-{4-tolyl}-prop-1E-enyl]-pyridin-2-yl)-prop-2E-enyl}-amine as a brown oil (208 mg, 87%). $^1$H-NMR; δ (CDCl$_3$), 7.38 (1H, t, J=8.5 Hz), 7.17–7.16 (3H, m), 7.09–7.04 (3H, m), 6.90 (1H, dt, J=16.0, 6.5 Hz), 6.66 (1H, d, J=7.5 Hz), 6.61 (1H, d, J=15.0 Hz), 3.43 (2H, d, J=5.5 Hz), 3.18 (2H, d, J=7.5 Hz), 2.54–2.49 (4H, m), 2.47 (3H, s), 2.38 (3H, s) and 1.77–1.73 (4H, m).

(c) N-Methyl-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide.

A solution of methyl-{3-(6-[3-pyrrolidino-1-{4-tolyl}-prop-1E-enyl]-pyridin-2-yl)-prop-2E-enyl}-amine (208 mg, 0.60 mmol), 4-(1H-2-methylimidazo[4,5-c]pyridin-1-ylmethyl)}benzoic acid dihydrochloride salt (204 mg, 0.60 mmol), EDC (172 mg, 0.90 mmol), HOAt (10 mg, 0.07 mmol) and N-methylmorpholine (132 μl, 1.20 mmol) in DMF (5 ml) was stirred at room temperature for 96 hours. Solvent was removed under reduced pressure and the residue partitioned between DCM and brine. The organics were dried over magnesium sulphate, filtered and solvent removed under reduced pressure to leave a brown foam. The product was purified by column chromatography on silica-gel eluting with 10–20% methanol in DCM. Product containing fractions were combined and solvent removed to yield N-methyl-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide as a brown foam (222 mg, 62%). $^{1}$H-NMR; δ (CDCl$_{3}$), 9.02 (1H, s), 8.37 (1H, d, J=5.5 Hz), 7.44 (2H, d, J=8.1 Hz), 7.42 (1H, t, J=7.7 Hz), 7.20 (2H, d, J=7.8 Hz), 7.17 (2H, d, J=5.5 Hz), 7.08 (2H, d, J=7.9 Hz), 7.08–7.00 (3H, m), 6.80–6.52 (3H, m), 5.34 (2H, s), 4.35 and 4.03 (2H, 2×bs), 3.18 (2H, d, J=7.0 Hz), 3.12 and 2.95 (3H, 2×bs), 2.59 (3H, s), 2.51 (4H, bs), 2.39 (3H, s) and 1.75 (4H, bs); $^{13}$C-NMR; δ (CDCl$_{3}$), 157.6, 153.4, 153.1, 142.1, 142.0, 141.4, 140.3, 139.8, 131.7, 129.7, 129.1, 127.7, 126.2, 121.2, 120.4, 104.8, 54.9, 54.2, 53.2, 47.0, 33.5, 23.5, 21.2 and 14.0.

EXAMPLE 4

N-Cyclohexyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide

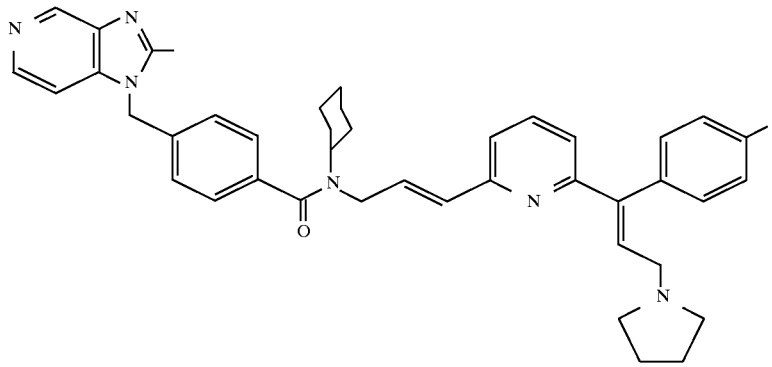

(a) Cyclohexyl-{3-(6-[3-pyrrolidino-1-{4-tolyl}-prop-1E-enyl]-pyridin-2-yl)-prop-2E-enyl}-amine.

A solution of 3-(6-[3-pyrrolidino-1-{4-tolyl}-prop-1E-enyl]-pyridin-2-yl)-prop-2E-enal (463 mg, 1.34 mmol) in DCM (20 ml) was treated with activated powdered 3 Å molecular sieves (3 g) and cyclohexylamine (175 μl, 1.53 mmol). The reaction was stirred for 18 hours, filtered and concentrated under reduced pressure to provide the imine as a brown oil. The residue was resuspended in dry methanol (20 ml), cooled in an ice-salt bath and treated under an inert atmosphere with sodium borohydride (62 mg, 1.64 mmol). The reaction was stirred for 2.5 hours and solvent removed under reduced pressure. The residue was taken up in DCM (10 ml) and washed with brine. The organics were dried over magnesium sulphate, filtered and concentrated to yield cyclohexyl-{3-(6-[3-pyrrolidino-1-{4-tolyl}-prop-1E-enyl]-pyridin-2-yl)-prop-2E-enyl}-amine as a brown oil (530 mg, 92%). $^{1}$H-NMR; δ (CDCl$_{3}$), 7.40 (1H, t, J=8.0 Hz), 7.22–7.17 (3H, m), 7.12–7.07 (3H, m), 6.92 (1H, dt, J=15.0, 6.0 Hz), 6.68 (1H, d, J=8.0 Hz), 6.62 (1H, d, J=16.0 Hz), 3.49 (2H, dd, J=6.5, 0.5 Hz), 3.18 (2H, d, J=8.0 Hz), 2.56–2.50 (5H, m), 2.40 (3H, s), 1.94 (2H, bd, J=13.0 Hz), 1.79–1.71 (6H, m), 1.66–1.60 (1H, m) and 1.33–1.06 (5H, m).

(b) N-Cyclohexyl-4-(1H-2-methylimidazo[4,5-c]pyridin-1-ylmethyl)-N-{3-(6-[3-Pyrrolidino-1-{4-tolyl}-prop-1E-enyl]-pyridin-2-yl)-prop-2E-enyl}-benzamide.

A solution of cyclohexyl-{3-(6-[3-pyrrolidino-1-{4-tolyl}-prop-1E-enyl]-pyridin-2-yl)-prop-2E-enyl}-amine (500 mg, 1.20 mmol), 4-(1H-2-methylimidazo[4,5-c]pyridin-1-ylmethyl)}benzoic acid sodium salt (348 mg, 1.20 mmol), EDC (246 mg, 1.81 mmol) and HOAt (15 mg) in DMF (15 ml) was stirred at room temperature for 96 hours. Solvent was removed under reduced pressure and the residue partitioned between DCM and brine. The organics were dried over magnesium sulphate, filtered and solvent removed under reduced pressure to leave a brown foam. The product was purified by column chromatography on silica-gel eluting with 10–20% methanol in DCM. Product containing fractions were combined and solvent removed to yield N-cyclohexyl-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide as a brown foam (555 mg, 69%). $^{1}$H-NMR; δ (CDCl$_{3}$), 9.03 (1H, s), 8.36 (1H, d, J=5.3 Hz), 7.40 (1H, t, J=7.7 Hz), 7.37 (2H, d, J=7.9 Hz), 7.19 (2H, d, J=7.9 Hz), 7.16–7.10 (2H, m), 7.08 (2H, d, J=7.9 Hz), 7.10–6.85 (3H, m), 6.85–6.20 (3H, bm), 5.33 (2H, s), 4.45–3.40 (3H, bm), 3.22 (2H, d, J=6.9 Hz), 2.58 (7H, bs), 2.38 (3H, s), 1.90–1.70 (8H, bm), 1.66–1.53 (3H, m) and 1.50–0.95 (3H, bm); $^{13}$C-NMR; δ (CDCl$_{3}$), 157.4, 154.6, 153.5, 142.0, 141.4, 140.3, 139.8, 136.5, 133.7, 130.7, 130.4, 129.7, 129.0, 127.2, 126.4, 120.4, 119.5, 104.9, 54.8, 54.1, 47.1, 23.5, 21.2 and 14.0.

EXAMPLE 5

4-(1H-2-Methylimidazo[4,5-c]pyridin-1-ylmethyl)-N-{3-[6-(3-pyrrolidino-1-{4-tolyl}-prop-1E-enyl)-pyridin-2-yl]-prop-2E-enyl}-benzamide

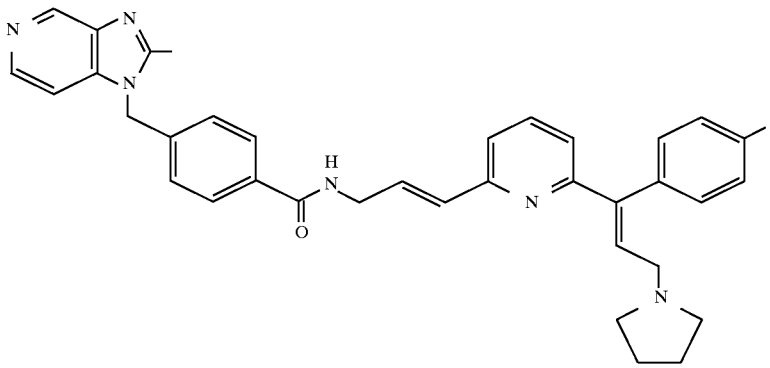

(a) 3-(6-[3-Pyrrolidino-1-{4-tolyl}-prop-1E-enyl]-pyridin-2-yl)-prop-2E-en-1-yl acetate.

Pyridine (110 μl, 1.36 mmol) was added to a solution of 3-(6-[3-pyrrolidino-1-{4-tolyl}-prop-1E-enyl]-pyridin-2-yl)-prop-2E-en-1-ol (227 mg, 0.68 mmol) in DCM (3 ml) under an inert atmosphere. Acetyl chloride (72 μl, 1.02 mmol) was added and the reaction stirred for 18 hours at room temperature. The reaction mixture was partitioned between DCM and brine. The organic layer was separated, dried over sodium sulphate, filtered and concentrated under vacuum to leave a brown oil. The product was purified by column chromatography on silica gel eluting with 5% methanol/DCM. Product containing fractions were combined and solvent removed to yield 3-(6-[3-pyrrolidino-1-{4-tolyl}-prop-1E-enyl]-pyridin-2-yl)-prop-2E-en-1-yl acetate as a brown gum (184 mg, 73%). $^1$H-NMR; δ (CDCl$_3$), 7.49 (1H, t, J=7.8 Hz), 7.24 (2H, d, J=7.9 Hz), 7.18–7.11 (2H, m), 7.06 (2H, d, J=7.9 Hz), 6.91–6.66 (3H, m), 4.79 (2H, dd, J=5.4, 0.7 Hz), 3.72 (2H, m), 3.20 (4H, bm), 2.40 (3H, s), 2.12 (3H, s) and 2.11–2.02 (4H, m).

(b) {3-(6-[3-Pyrrolidino-1-{4-tolyl}-prop-1E-enyl]-pyridin-2-yl)-prop-2E-enyl}-azide.

A solution of 3-(6-[3-pyrrolidino-1-{4-tolyl}-prop-1E-enyl]-pyridin-2-yl)-prop-2E-en-1-yl acetate (136 mg, 0.365 mmol) in a mixture of THF/water (5:1, 5 ml) was treated with sodium azide (28 mg, 0.44 mmol) and tetrakis(triphenylphosphine) palladium(0) (17 mg, 0.015 mmol). The reaction was stirred at room temperature for 18 hours. Solvent was removed under reduced pressure to leave a dark brown residue. The product was purified by column chromatography on silica-gel eluting with 5% methanol/DCM. Product containing fractions were combined and solvent removed under reduced pressure to yield {3-(6-[3-pyrrolidino-1-{4-tolyl}-prop-1E-enyl]-pyridin-2-yl)-prop-2E-enyl}-azide as a brown gum (110 mg, 85%). $^1$H-NMR; δ (CDCl$_3$), 7.67 (1H, m), 7.56 (1H, m), 7.40 (2H, m), 7.24 (2H, d, J=8.2 Hz), 7.19 (1H, t, J=6.8 Hz), 7.10 (2H, m), 6.91 (1H, dt, J=15.8, 6.6 Hz), 6.73 (2H, m), 4.02 (2H, d, J=8.8 Hz), 3.35 (2H, m), 2.70 (2H, m), 2.41 (3H, s) and 1.82 (4H, m).

(c) {3-(6-[3-Pyrrolidino-1-{4-tolyl}-prop-1E-enyl]-pyridin-2-yl)-prop-2E-enyl}-amine.

A solution of {3-(6-[3-pyrrolidino-1-{4-tolyl}-prop-1E-enyl]-pyridin-2-yl)-prop-2E-enyl}-azide (154 mg, 0.43 mmol) in methanol (10 ml) was treated with tin (II) chloride (163 mg, 0.86 mmol). The reaction showed a slight exotherm and darkened in colour. After 1 hour solvent was removed under reduced pressure to leave a green gum. The residue was treated with sodium hydroxide solution (5M) and the product extracted (×4) with diethyl ether. The combined organic extracts were combined, dried over magnesium sulphate, filtered and solvent removed to yield {3-(6-[3-pyrrolidino-1-{4-tolyl}-prop-1E-enyl]-pyridin-2-yl)-prop-2E-enyl}-amine as a brown gum (77.5 mg, 54%). $^1$H-NMR; δ (CDCl$_3$), 7.43 (1H, t, J=8.1 Hz), 7.21 (3H, m), 7.09 (3H, m), 6.99 (1H, dt, J=16.3, 6.3 Hz), 6.69 (1H, d, J=8.0 Hz), 6.61 (1H, dt, J=15.6, 1.4 Hz), 3.56 (2H, dd, J=5.8, 1.3 Hz), 3.21 (2H, d, J=9.6 Hz), 2.56 (4H, m), 2.40 (3H, s), 1.79 (4H, s) and 1.71 (2H, bs).

(d) 4-(1H-2-Methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide.

DMF (3 ml) was added to a mixture of {3-(6-[3-pyrrolidino-1-{4-tolyl}-prop-1E-enyl]-pyridin-2-yl)-prop-2E-enyl}-amine (77.5 mg, 0.23 mmol), 4-(1H-2-methyl-imidazo[4,5-c]pyridin-1-ylmethyl)}benzoic acid sodium salt (101 mg, 0.28 mmol), EDC (54 mg, 0.28 mmol) and HOAt (38 mg, 0.28 mmol). N-Methylmorpholine (102 μl, 0.93 mmol) was added and the suspension stirred at room temperature for 96 hours. Solvent was removed under reduced pressure and the residue partitioned between DCM and saturated sodium bicarbonate solution. The organic layer was separated, washed with brine, dried over magnesium sulphate, filtered and concentrated under reduced pressure to a brown gum. The product was purified by column chromatography on silica-gel eluting with 5–20% methanol/DCM. Product containing fractions were combined and solvent removed to yield 4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide as a pale brown glass (33.6 mg, 24%). $^1$H-NMR; δ (MeOD), 8.84 (1H, s), 8.29 (1H, d, J=5.7 Hz), 7.86 (2H, d, J=8.3 Hz), 7.52 (1H, d, J=5.7 Hz), 7.51 (1H, t, J=7.8 Hz), 7.22 (5H, m), 7.04 (2H, d, J=8.0 Hz), 6.98 (1 H, t, J=7.0 Hz), 6.84 (1H, dt, J=15.8, 5.6 Hz), 6.72 (1H, d, J=8.0 Hz), 6.66 (1H, d, J=15.8 Hz), 5.60 (2H, s), 4.20 (2H, dd, J=5.7, 1.2 Hz), 3.24 (2H, d, J=7.0 Hz), 2.63 (3H, s), 2.57 (4H, m), 2.37 (3H, s) and 1.76 (4H, m); $^{13}$C-NMR; δ (MeOD), 167.8, 157.2, 155.4, 154.5, 142.9, 141.0, 140.8, 139.7, 139.2, 139.1, 137.2, 136.8, 134.9, 134.0, 130.6, 130.6, 129.3, 129.3, 128.8, 128.8, 127.8, 127.7, 126.5, 120.7, 119.7, 106.0, 54.0, 53.5, 53.3, 46.5, 41.0, 22.7, 19.9, 19.8 and 12.4.

EXAMPLE 6

N-(3-Methyl-but-1-yl)-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide

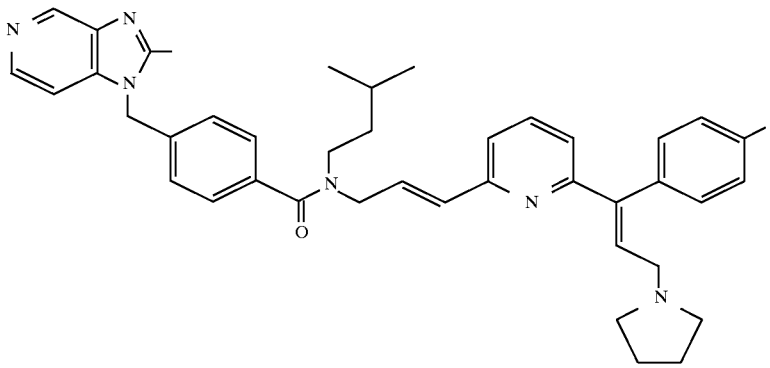

(a) (3-Methyl-but-1-yl)-{3-(6-[3-pyrrolidino-1-{4-tolyl}-prop-1E-enyl]-pyridin-2-yl)-prop-2E-enyl}-amine.

A solution of (E)-3-(6-[3-pyrrolidino-1-{4-tolyl}-prop-1E-enyl]-pyridin-2-yl)-prop-2-enal (345 mg, 1.04 mmol) in DCM (20 ml) was treated with activated powdered 3 Å molecular sieves (2 g) and isoamylamine (133 µl, 1.14 mmol). The reaction was stirred for 18 hours, filtered and concentrated under reduced pressure to provide the imine as a brown oil. The residue was resuspended in dry methanol (20 ml), cooled in an ice-salt bath and treated under an inert atmosphere with sodium borohydride (39 mg, 1.04 mmol). The reaction was stirred for 2 hours and solvent removed under reduced pressure. The residue was taken up in DCM and washed with saturated sodium bicarbonate solution. The organics were dried over anhydrous sodium sulphate, filtered and concentrated to yield (3-methyl-but-1-yl)-{3-(6-[3-pyrrolidino-1-{4-tolyl}-prop-1E-enyl]-pyridin-2-yl)-prop-2E-enyl}-amine as an orange oil (388 mg, 92%). $^1$H-NMR; δ (CDCl$_3$), 7.42 (1H, t, J=7.9 Hz), 7.20 (3H, m), 7.10 (3H, m), 6.93 (1H, dt, J=6.0, 3.3 Hz), 6.68 (1H, d, J=8.1 Hz), 6.63 (1H, d, J=15.8 Hz), 3.48 (2H, dd, J=6,2, 1.3 Hz), 3.18 (2H, d, J=7.0 Hz), 2.69 (2H, t, J=7.3 Hz), 2.53 (4H, m), 2.40 (3H, s), 1.77 (5H, m), 1.65 (2H, q, J=6.8 Hz) and 0.92 (6H, d, J=6.8 Hz).

(b) N-(3-Methyl-but-1-yl)-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide.

A solution of (3-methyl-but-1-yl)-{3-(6-[3-pyrrolidino-1-(4-tolyl}-prop-1E-enyl]-pyridin-2-yl)-prop-2E-enyl}-amine (383 mg, 0.95 mmol), 4-(1H-2-methylimidazo[4,5-c]pyridin-1-ylmethyl)}benzoic acid dihydrochloride salt (323 mg, 0.95 mmol), EDC (274 mg, 1.43 mmol), N-methylmorpholine (209 µl, 1.90 mmol) and HOAt (20 mg) in DMF (10 ml) was stirred at room temperature for 96 hours. Solvent was removed under reduced pressure and the residue partitioned between DCM and brine. The organics were dried over sodium sulphate, filtered and solvent removed under reduced pressure to leave a brown foam. The product was purified by column chromatography on silica-gel eluting with 10–15% methanol in DCM. Product containing fractions were combined and solvent removed to yield N-(3-methyl-but-1-yl)-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide as a pale brown foam (313 mg, 51%). $^1$H-NMR; δ (CDCl$_3$), 9.01 (1H, s), 8.35 (1H, d, J=5.7 Hz), 7.51–7.42 (3H, m), 7.27–7.05 (10H, m), 6.82–6.73 (2H, m), 5.37 (2H, s), 4.34 (1H, m), 4.05 (1H, bs), 3.55 (2H, d, J=5.9 Hz), 3.25 (1H, m), 3.00 (4H, m), 2.60 (3H, s), 2.40 (3H, s), 1.97 (4H, bs), 1.57–1.40 (4H, bm) 0.95 (4H, d, J=5.5 Hz) and 0.70 (2H, m); $^{13}$C-NMR; δ (CDCl$_3$), 170.8, 156.1, 154.2, 153.5, 142.0, 141.8, 140.3, 139.8, 137.8, 137.0, 136.8, 136.5, 136.3, 136.0, 133.9, 132.3, 131.0, 130.0, 129.4, 129.3, 127.5, 127.4, 126.2, 121.4, 121.3, 121.0, 120.4, 104.9, 77.4, 53.7, 53.2, 53.0, 50.5, 47.0, 46.9, 46.2, 43.7, 37.3, 35.8, 26.2, 25.5, 23.4, 23.3, 22.5, 22.2, 21.2 and 14.0.

EXAMPLE 7

N-iso-Butyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide

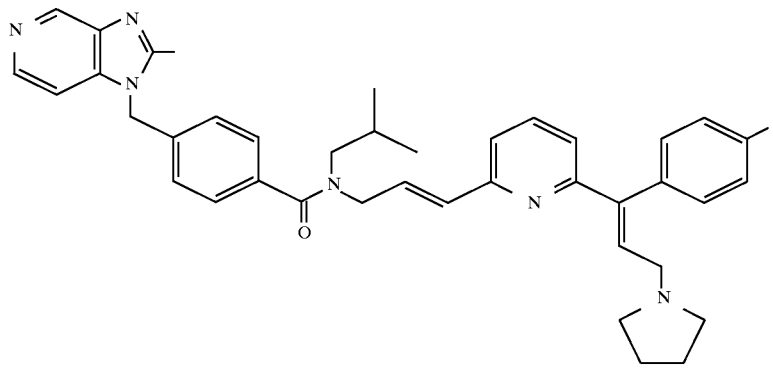

(a)iso-Butyl-{3-(6-[3-pyrrolidino-1-{4-tolyl}-prop-1E-enyl]-pyridin-2-yl)-prop-2E-enyl}-amine.

A solution of 3-(6-[3-pyrrolidino-1-{4-tolyl}-prop-1E-enyl]-pyridin-2-yl)-prop-2E-enal (369 mg, 1.11 mmol) in DCM (20 ml) was treated with activated powdered 3 Å molecular sieves (2 g) and iso-butylamine (120 μl, 1.22 mmol). The reaction was stirred for 18 hours, filtered and concentrated under reduced pressure to provide the imine as a brown oil. The residue was resuspended in dry methanol (20ml), cooled in an ice-salt bath and treated under an inert atmosphere with sodium borohydride (40 mg, 1.00 mmol). The reaction was stirred for 2 hours and solvent removed under reduced pressure. The residue was taken up in DCM (10 ml) and washed with brine. The organics were dried over anhydrous magnesium sulphate, filtered and concentrated to yield iso-butyl-{3-(6-[3-pyrrolidino-1-{4-tolyl}-prop-1E-enyl]-pyridin-2-yl)-prop-2E-enyl}-amine as an orange oil (300 mg, 80%). $^1$H-NMR; δ (CDCl$_3$), 7.38 (1H, t, J=8.0 Hz), 7.20–7.17 (3H, m), 7.10–7.05 (3H, m), 6.91 (1H, dt, J=16.0, 6.5 Hz), 6.67 (1H, d, J=8.0 Hz), 6.62 (1H, d, J=14.0 Hz), 3.45 (2H, d, J=4.0 Hz), 3.19 (2H, d, J=7.5 Hz), 2.57–2.52 (4H, m), 2.48 (2H, d, J=6.0 Hz), 2.38 (3H, s), 1.81–1.74 (5H, m), 1.23 (1H, s) and 0.92 (6H, d, J=7.5 Hz).

(b) N-(iso-Butyl)-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide.

A solution of iso-butyl-{3-(6-[3-pyrrolidino-1-{4-tolyl}-prop-1E-enyl]-pyridin-2-yl)-prop-2E-enyl}-amine (300 mg, 0.77 mmol), 4-(1H-2-methylimidazo[4,5-c]pyridin-1-ylmethyl)}benzoic acid dihydrochloride salt (262 mg, 0.77 mmol), EDC (221 mg, 1.16 mmol), N-methylmorpholine (270 μl, 1.54 mmol) and HOAt (15 mg) in DMF (10 ml) was stirred at room temperature for 96 hours. Solvent was removed under reduced pressure and the residue partitioned between DCM and brine. The organics were dried over magnesium sulphate, filtered and solvent removed under reduced pressure to leave a brown foam. The product was purified by column chromatography on silica-gel eluting with 10–20% methanol in DCM. Product containing fractions were combined and solvent removed to yield N-(iso-butyl)-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide as a pale brown foam (264 mg, 54%). $^1$H-NMR; δ (CDCl$_3$), 9.03 (1H, s), 8.38 (1H, d, J=5.5 Hz), 7.44 (1H, t, J=7.8 Hz), 7.41 (2H, d, J=8.1 Hz), 7.22–6.98 (9H, m), 6.87–6.40 (3H, m), 5.35 (2H, s), 4.37 (0.64H, d, J=5.2 Hz), 4.05 (1.36H, d, J=4.1 Hz), 3.41 (1.32H, d, J=7.5 Hz), 3.19 (2H, d, J=6.6 Hz), 3.11 (0.68H, d, J=7.0 Hz), 2.60 (3H, s), 2.53 (4H, bs), 2.39 (3H, s), 2.20–1.85 (1H, m), 1.77 (4H, bs), 0.97 (4H, d, J=6.6 Hz) and 0.94 (2H, d, J=6.8 Hz); $^{13}$C-NMR; δ (CDCl$_3$), 171.3 157.5, 153.3, 142.1, 142.0, 140.3, 139.8, 137.0, 136.9, 136.6, 136.1, 135.2, 133.0, 131.5, 129.7, 129.3, 129.1, 128.9, 128.0, 127.4, 126.2, 121.1, 120.4, 104.8, 55.7, 54.7, 54.1, 51.8, 51.2, 47.0, 46.1, 26.6, 23.4, 21.2, 20.1, 19.8 and 14.0.

EXAMPLE 8

N-Cyclopentyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide

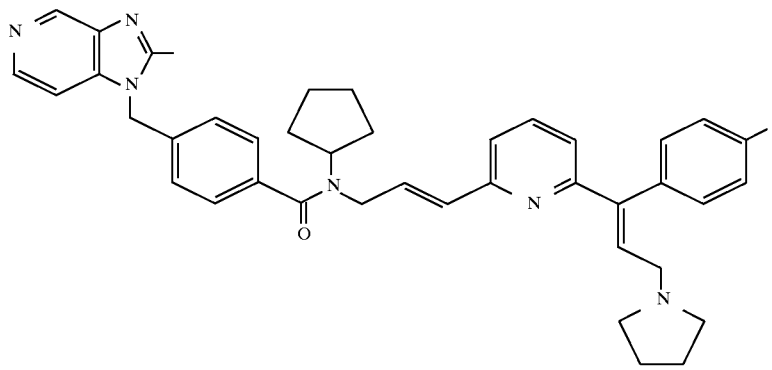

(a) Cyclopentyl-{3-(6-[3-pyrrolidino-1-{4-tolyl}-prop-1E-enyl]-pyridin-2-yl)-prop-2E-enyl}-amine.

A solution of 3-(6-[3-pyrrolidino-1-{4-tolyl}-prop-1E-enyl]-pyridin-2-yl)-prop-2E-enal (340 mg, 1.02 mmol) in DCM (20 ml) was treated with activated powdered 3 Å molecular sieves (2 g) and cyclopentylamine (111 μl, 1.12 mmol). The reaction was stirred for 18 hours, filtered and concentrated under reduced pressure to provide the imine as a brown oil. The residue was resuspended in dry methanol (20 ml), cooled in an ice-salt bath and treated under an inert atmosphere with sodium borohydride (37 mg, 0.98 mmol). The reaction was stirred for 2 hours and solvent removed under reduced pressure. The residue was taken up in DCM and washed with saturated sodium bicarbonate solution. The organic phase was dried over anhydrous sodium sulphate, filtered and concentrated to yield cyclopentyl-{3-(6-[3-pyrrolidino-1-{4-tolyl}-prop-1E-enyl]-pyridin-2-yl)-prop-2E-enyl}-amine as a brown oil (374 mg, 95%). $^1$H-NMR; δ (CDCl$_3$), 7.42 (1H, t, J=7.8 Hz), 7.20 (3H, m), 7.09 (3H, m), 6.93 (1H, m), 6.68 (1H, d, J=7.8 Hz), 6.63 (1H, d, J=15.5 Hz), 3.46 (2H, dd, J=6.1, 1.3 Hz), 3.18 (3H, m), 2.53 (4H, m), 2.40 (3H, s), 1.89 (2H, m), 1.77 (4H, m), 1.71 (2H, m), 1.56 (2H, m) and 1.37 (2H, m).

(b) N-Cyclopentyl-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide.

A solution of cyclopentyl-{3-(6-[3-pyrrolidino-1-{4-tolyl}-prop-1E-enyl]-pyridin-2-yl)-prop-2E-enyl}-amine (370 mg, 0.92 mmol), 4-(1H-2-methylimidazo[4,5-c]pyridin-1-ylmethyl)}benzoic acid dihydrogen chloride salt (314 mg, 0.92 mmol), EDC (265 mg, 1.38 mmol) N-methylmorpholine (202 μl, 1.82 mmol) and HOAt (20 mg) in DMF (10 ml) was stirred at room temperature for 96 hours. Solvent was removed under reduced pressure and the residue partitioned between DCM and saturated sodium bicarbonate solution. The organics were dried over sodium sulphate, filtered and solvent removed under reduced pressure to leave a brown foam. The product was purified by column chromatography on silica-gel eluting with 10–15% methanol in DCM. Product containing fractions were combined and solvent removed to yield N-cyclopentyl-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide as a brown foam (74 mg, 12%). $^1$H-NMR; δ (CDCl$_3$), 9.03 (1H, s), 8.38 (1H, d, J=5.4 Hz), 7.42 (3H, m), 7.19–7.07 (9H, m), 6.74 (3H, m), 5.35 (2H, s), 4.16 (2H, bs), 3.18 (2H, d, J=7.0 Hz), 2.60 (3H, s), 2.52 (4H, m), 2.39 (3H, s), 2.23 (1H, m) and 1.75–1.50 (12H, bm); $^{13}$C-NMR; δ (CDCl$_3$), 157.4, 153.5, 142.0, 141.9, 141.4, 140.3, 139.8, 137.4, 136.5, 136.4, 136.0, 135.4, 131.4, 130.6, 129.7, 129.0, 127.4, 126.3, 120.7, 119.6, 104.8, 60.6, 54.8, 54.1, 47.0, 30.1, 29.6, 24.0 23,4, 23.2, 21.2 and 14.0.

EXAMPLE 9

N-(R,S) sec-Butyl-4-(1H-2-methylimidazo[4,5-c]pyridin-1-ylmethyl)-N-(E)-{3-[6-(3-pyrrolidin-1-yl-1-{4-tolyl}-prop-1E-enyl)-pyridin-2-yl]-prop-2-enyl}-benzamide

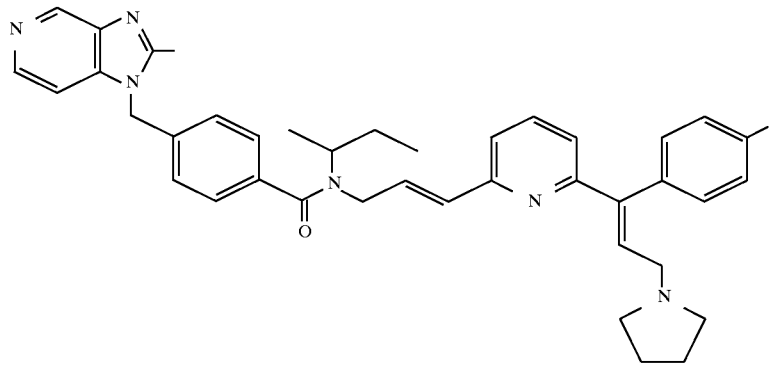

(a) (R,S)-sec-Butyl-{3-(6-[3-pyrrolidino-1-{4-tolyl}-prop-1E-enyl]-pyridin-2-yl)-prop-2E-enyl}-amine.

A solution of 3-(6-[3-pyrrolidino-1-{4-tolyl}-prop-1E-enyl]-pyridin-2-yl)-prop-2E-enal (217 mg, 0.653 mmol) in DCM (10 ml) was treated with activated powdered 3 Å molecular sieves (1 g) and (R,S)-sec-butylamine (225 μl, 2.16 mmol). The reaction was stirred for 36 hours, filtered and concentrated under reduced pressure to provide the imine as a brown oil. The residue was resuspended in dry methanol (20 ml), cooled in an ice-salt bath and treated under an inert atmosphere with sodium borohydride (62 mg, 1.64 mmol). The reaction was stirred for 2.5 hours and solvent removed under reduced pressure. The residue was taken up in DCM (10 ml) and washed with brine. The organics were dried over magnesium sulphate, filtered and concentrated to yield (R,S)-sec-butyl-{3-(6-[3-pyrrolidino-1-{4-tolyl}-prop-1E-enyl]-pyridin-2-yl)-prop-2E-enyl}-amine as an orange oil (530 mg, 92%). $^1$H-NMR; δ (CDCl$_3$), 7.42 (1H, t, J=7.8 Hz), 7.26–7.19 (3H, m), 7.15–7.08 (3H, m), 6.93 (1H, dt, J=15.7, 6.1 Hz), 6.68 (1H, d, J=8.2 Hz), 6.64 (1H, dt, J=15.9, 1.4 Hz), 3.58–3.41 (2H, m), 3.19 (2H, d, J=6.9 Hz), 2.77–2.64 (1H, m), 2.57–2.52 (4H, m), 2.41 (3H, s), 1.82–1.76 (4H, m), 1.64–1.49 (1H, m), 1.47–1.33 (1H, m), 1.28 (1H, s), 1.09 (3H, d, J=6.3 Hz) and 0.93 (3H, t, J=7.4 Hz).

(b) N-(R,S)-sec-Butyl-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide.

A solution of (R,S)-sec-butyl-{3-(6-[3-pyrrolidino-1-{4-tolyl}-prop-1E-enyl]-pyridin-2-yl)-prop-2E-enyl}-amine (225 mg, 0.578 mmol), 4-(1H-2-methylimidazo[4,5-c]pyridin-1-ylmethyl)}benzoic acid sodium salt (167 mg, 0.578 mmol), EDC (166 mg, 0.867 mmol) and HOAt (10 mg) in DMF (10 ml) was stirred at room temperature for 96 hours. Solvent was removed under reduced pressure and the residue partitioned between DCM and brine. The organics were dried over magnesium sulphate, filtered and solvent removed under reduced pressure to leave a brown foam. The product was purified by column chromatography on silica-gel eluting with 10–50% methanol in DCM. Product containing fractions were combined and solvent removed to yield N-(R,S)-sec-butyl-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide as a brown oil (218 mg, 59%). $^1$H-NMR; δ (CDCl$_3$), 9.01 (1H, bs), 8.34 (1H, bs), 7.39 (1H, t, J=7.8 Hz), 7.37–7.34 (2H, m), 7.20–6.29 (12H, bm), 5.32 (2H, s), 4.54–3.60 (3H, bm), 3.16 (2H, d, J=6.9 Hz), 2.57 (3H, bs), 2.50 (4H, bm), 2.36 (3H, s), 1.73 (4H, bm) and 1.70–0.68 (8H, bm); $^{13}$C-NMR; δ (CDCl$_3$), 171.2, 170.9, 157.1, 154.0, 153.2, 152.9, 141.5, 141.3, 141.1, 139.9, 139.4, 137.7, 137.0, 136.4, 136.1, 135.7, 135.1, 131.6, 130.6, 130.3, 129.9, 129.3, 128.6, 127.0, 126.0, 120.3, 119.4, 119.1, 104.6, 56.2, 54.3, 53.7, 52.2, 47.2, 46.6, 41.8, 27.6, 26.9, 23.1, 20.8, 19.5, 18.0, 13.6 and 10.7.

EXAMPLE 10

N-tert-Butyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide

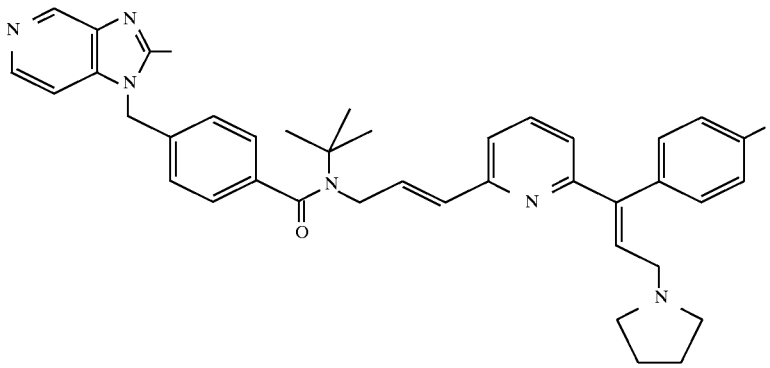

(a) tert-Butyl-{3-(6-[3-pyrrolidino-1-{4-tolyl}-prop-1E-enyl]-pyridin-2-yl)-prop-2E-enyl}-amine.

A solution of 3-(6-[3-pyrrolidino-1-{4-tolyl}-prop-1E-enyl]-pyridin-2-yl)-prop-2E-enal (323 mg, 0.927 mmol) in DCM (20 ml) was treated with activated powdered 3 Å molecular sieves (2 g) and tertbutylamine (350 μl, 3.21 mmol). The reaction was stirred for 1 week, filtered and concentrated under reduced pressure to provide the imine as a brown oil. The residue was resuspended in dry methanol (20 ml), cooled in an ice-salt bath and treated under an inert atmosphere with sodium borohydride (35 mg, 0.93 mmol). The reaction was stirred for 2 hours and solvent removed under reduced pressure. The residue was taken up in DCM (10 ml) and washed with brine. The organics were dried over anhydrous magnesium sulphate, filtered and concentrated to yield tert-butyl-{3-(6-[3-pyrrolidino-1-{4-tolyl}-prop-1E-enyl]-pyridin-2-yl)-prop-2E-enyl}-amine as an orange oil (439 mg, crude). $^1$H-NMR; δ (CDCl$_3$), 7.40 (1H, t, J=7.5 Hz), 7.24–7.16 (3H, m), 7.13–7.06 (3H, m), 6.94 (1H, dt, J=7.5, 6.6 Hz), 6.70–6.60 (2H, m), 3.43 (2H, dd, J=5.5, 1.0 Hz), 3.19 (2H, d, J=7.0 Hz), 2.57–2.50 (4H, m), 2.39 (3H, s), 1.80–1.73 (4H, m) and 1.16 (9H, s).

(b) N-tert-Butyl-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide.

A solution of tert-butyl-{3-(6-[3-pyrrolidino-1-{4-tolyl}-prop-1E-enyl]-pyridin-2-yl)-prop-2E-enyl}-amine (439 mg, 1.13 mmol), 4-(1H-2-methylimidazo[4,5-c]pyridin-1-ylmethyl)}benzoic acid sodium salt (326 mg, 1.13 mmol), EDC (324 mg, 1.69 mmol) and HOAt (15 mg) in DMF (10 ml) was stirred at room temperature for 96 hours. Solvent was removed under reduced pressure and the residue partitioned between DCM and brine. The organics were dried over magnesium sulphate, filtered and solvent removed under reduced pressure to leave a brown foam. The product was purified by column chromatography on silica-gel eluting with 10–25% methanol in DCM. Product containing fractions were combined and solvent removed to yield N-tert-butyl-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide as a brown oil (75 mg, 11%). $^1$H-NMR; δ (CDCl$_3$), 9.01 (1H, d, J=0.7 Hz), 8.35 (1H, d, J=5.5 Hz), 7.46 (1H, t, J=7.8 Hz), 7.35 (2H, d, J=8.2 Hz), 7.24–7.15 (4H, m), 7.07 (2H, d, J=8.0 Hz), 7.03–6.99 (3H, m), 6.78–6.67 (2H, m), 6.43 (1H, bd, J=15.8 Hz), 5.34 (2H, s), 4.10 (2H, d, J=3.6 Hz), 3.48 (2H, d, J=6.7 Hz), 2.90 (4H, bs), 2.58 (3H, s), 2.40 (3H, s), 1.92 (4H, bm) and 1.58 (9H, s); $^{13}$C-NMR; δ (CDCl$_3$), 172.7, 156.4, 153.7, 153.6, 142.0, 141.8, 140.3, 139.8, 139.3, 137.7, 137.0, 135.7, 133.3, 130.7, 129.4, 129.3, 126.9, 126.1, 121.2, 120.5, 104.9, 57.8, 53.9, 53.4, 49.2, 47.0, 28.7, 23.4, 21.2 and 14.0.

EXAMPLE 11

N-3,5-Dimethylcyclohexyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl)-benzamide

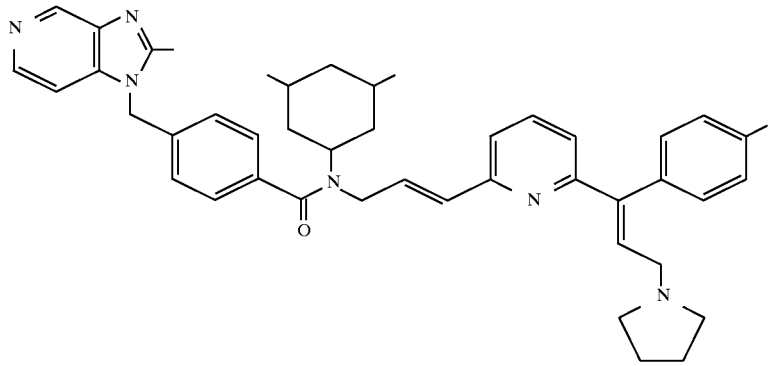

(a) 3,5-Dimethylcyclohexyl-{3-(6-[3-pyrrolidino-1-{4-tolyl}-prop-1E-enyl]-pyridin-2-yl)-prop-2E-enyl}-amine.

A solution of 3-(6-[3-pyrrolidino-1-{4-tolyl}-prop-1E-enyl]-pyridin-2-yl)-prop-2E-enal (206 mg, 0.62 mmol) in DCM (10 ml) was treated with activated powdered 3 Å molecular sieves (1 g) and 3,5-dimethylcyclohexylamine (169 mg, 1.36 mmol). The reaction was stirred for 36 hours, filtered and concentrated under reduced pressure to provide the imine as a brown oil. The residue was resuspended in dry methanol (10 ml), cooled in an ice-salt bath and treated under an inert atmosphere with sodium borohydride (30 mg, 0.79 mmol). The reaction was stirred for 2 hours and solvent removed under reduced pressure. The residue was taken up in DCM (10 ml) and washed with brine. The organics were dried over anhydrous magnesium sulphate, filtered and concentrated under reduced pressure. The product was purified by column chromatography on silica-gel, eluting with 10–20% methanol/DCM. Product containing fractions were combined and solvent removed under reduced pressure to yield 3,5-dimethylcyclohexyl-{3-(6-[3-pyrrolidino-1-{4-tolyl}-prop-1E-enyl]-pyridin-2-yl)-prop-2E-enyl}-amine as a brown oil (50 mg). $^1$H-NMR; δ (CDCl$_3$), 7.44 (1H, t, J=8.0 Hz), 7.26–7.19 (3H, m), 7.16–7.08 (3H, m), 6.94 (1H, dt, J=16.0, 6.5 Hz), 6.71–6.62 (2H, m), 3.47 (2H, dd, J=6.5, 1.0 Hz), 3.20 (2H, d, J=7.0 Hz), 3.06–3.01 (1H, m), 2.59–2.51 (4H, m), 2.42 (3H, s), 1.84–1.61 (10H, m), 1.02 (2H, dt, J=13.5, 2.5 Hz), 0.90 (6H, d, J=6.0 Hz) and 0.64–0.49 (1H, m).
(b) N-3,5-Dimethylcyclohexyl-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide.

A solution of 3,5-dimethylcyclohexyl-(E)-{3-(6-[3-pyrrolidino-1-{4-tolyl}-prop-1E-enyl]-pyridin-2-yl)-prop-2-enyl}-amine (50 mg, 0.11 mmol), 4-(1H-2-methylimidazo[4,5-c]pyridin-1-ylmethyl)}benzoic acid sodium salt (60 mg, 0.20 mmol), EDC (33 mg, 0.17 mmol) and HOAt (5 mg) in DMF (10 ml) was stirred at room temperature for 12 days. Solvent was removed under reduced pressure and the residue partitioned between DCM and brine. The organics were dried over magnesium sulphate, filtered and solvent removed under reduced pressure to leave a brown oil. The product was purified by column chromatography on silica-gel eluting with 10–25% methanol in DCM. Product containing fractions were combined and solvent removed to yield N-3,5-dimethylcyclohexyl-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide as a yellow oil (43 mg, 54%). $^1$H-NMR; δ (CDCl$_3$), 9.02 (1H, s), 8.35 (1H, bd, J=4.5 Hz), 7.41 (1H, t, J=7.8 Hz), 7.38 (2H, d, J=8.1 Hz), 7.22–6.99 (9H, m), 6.78 (1H, dt, J=15.6, 5.0 Hz), 6.69 (1H, d, J=7.8 Hz), 6.56–6.33 (1H, m), 5.34 (2H, s), 4.50–4.10 (1H, bm), 4.25 (2H, bd, J=3.6 Hz), 3.19 (2H, d, J=6.9 Hz), 2.58 (3H, s), 2.53 (4H, bs), 2.39 (3H, s), 2.10–1.60 (5H, bm), 1.76 (4H, bm), 1.34–1.21 (2H, m), 0.95–0.66 (1H, m) and 0.84 (6H, bd, J=6.3 Hz); $^{13}$C-NMR; δ (CDCl$_3$), 157.4, 153.5, 142.1, 142.0, 141.6, 140.3, 139.8, 137.9, 136.9, 136.7, 135.9, 135.3, 129.7, 129.1, 127.4, 126.2, 120.8, 119.9, 104.9, 54.8, 54.1, 47.0, 36.9, 28.3, 23.5, 22.5, 21.3 and 14.0.

EXAMPLE 12

N-iso-Propyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl)-benzamide

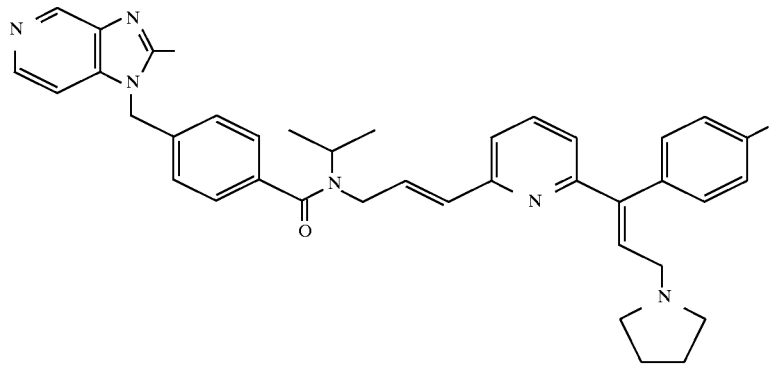

(a) iso-Propyl-{3-(6-[3-pyrrolidino-1-{4-tolyl}-prop-1E-enyl]-pyridin-2-yl)-prop-2E-enyl}-amine.

A solution of 3-(6-[3-pyrrolidino-1-{4-tolyl}-prop-1E-enyl]-pyridin-2-yl)-prop-2E-enal (415 mg, 1.25 mmol) in DCM (20 ml) was treated with activated powdered 3 Å molecular sieves (2 g) and isopropylamine (427 μl, 5.00 mmol). The reaction was stirred for 96 hours, filtered and concentrated under reduced pressure to provide the imine as a brown oil. The residue was resuspended in dry methanol (10 ml), cooled in an ice-salt bath and treated under an inert atmosphere with sodium borohydride (45 mg, 1.18 mmol). The reaction was stirred for 2 hours and solvent removed under reduced pressure. The residue was taken up in DCM (10 ml) and washed with saturated sodium bicarbonate. The organics were dried over sodium sulphate, filtered and concentrated under reduced pressure to yield isopropyl-{3-(6-[3-pyrrolidino-1-{4-tolyl}-prop-1E-enyl]-pyridin-2-yl)-prop-2E-enyl}-amine as a brown oil (413 mg, 93%). $^1$H-NMR; δ (CDCl$_3$), 7.42 (1H, t, J=7.7 Hz), 7.23–6.88 (7H, bm), 6.65 (2H, m), 3.47 (2H, d, J=4.9 Hz), 3.19 (2H, J=6.9 Hz), 2.92 (1H, m), 2.53 (4H, m), 2.41 (3H, s), 1.77 (4H, m) and 1.12 (6H, d, J=6.3 Hz).

(b) N-iso-Propyl-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide.

A solution of iso-propyl-{3-(6-[3-pyrrolidino-1-{4-tolyl}-prop-1E-enyl]-pyridin-2-yl)-prop-2E-enyl}-amine (405 mg, 1.08 mmol), 4-(1H-2-methylimidazo[4,5-c]pyridin-1-ylmethyl)benzoic acid dihydrochloride salt (367 mg, 1.08 mmol), EDC (311 mg, 1.62 mmol), N-methylmorpholine (238 μl, 2.16 mmol) and HOAt (20 mg) in DMF (10 ml) was stirred at room temperature for 8 days. Solvent was removed under reduced pressure and the residue partitioned between DCM and saturated sodium bicarbonate solution. The organics were dried over sodium sulphate, filtered and solvent removed under reduced pressure to leave a brown oil. The product was purified by column chromatography on silica-gel eluting with 10–15% methanol in DCM. Product containing fractions were combined and solvent removed to yield N-iso-propyl-4-(1H-2- methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide as a pale brown foam (180 mg, 27%). $^1$H-NMR; δ (MeOD), 8.74 (1H, s), 8.19 (1H, d, J=5.0 Hz),7.46 (2H, t, J=7.8 Hz), 7.32–6.58 (13H, bm), 5.49 (2H, s), 4.15–3.94 (3H, bm), 3.49 (2H, d, J=6.5 Hz), 2.87 (4H, bs), 2.54 (3H, s), 2.27 (3H, s), 1.79 (4H, m) and 1.21–1.11 (6H, m); $^{13}$C-NMR; δ (MeOD), 173.1, 157.9, 156.8, 156.1, 147.0, 142.4, 142.2, 141.1, 140.5, 139.2, 138.6, 138.4, 137.9, 135.5, 133.0, 132.7, 132.3, 130.7, 130.5, 128.2, 128.1, 124.7, 122.4, 121.7, 107.5, 54.9, 54.8, 52.5, 47.9, 43.2, 24.0, 21.3, 20.5 and 13.9.

EXAMPLE 13

N-Ethyl-4-(1H-2-methylimidazo[4,5-c]pyridin-1-ylmethyl)-N-{3-[6-(3-pyrrolidin-1-yl1-{4-tolyl}-prop-1E-enyl)-pyridin-2-yl]-prop-2E-enyl}-benzamide

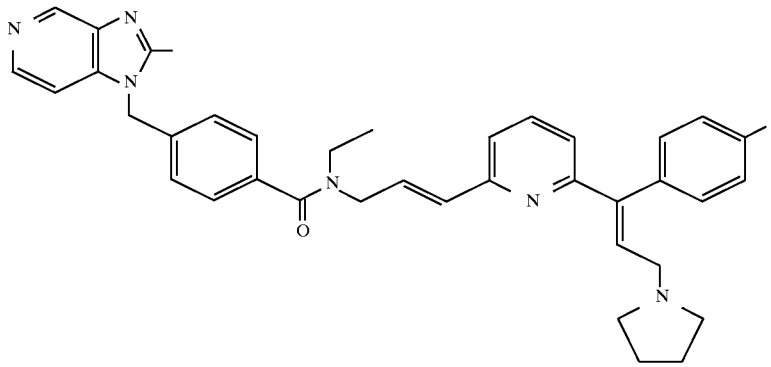

(a) Ethyl)-{3-(6-[3-pyrrolidin-1-yl-1-{4-tolyl}-prop-1E-enyl]-pyridin-2-yl)-prop-2E-enyl}-amine.

A solution of 3-(6-[3-pyrrolidino-1-{4-tolyl}-prop-1E-enyl]-pyridin-2-yl)-prop-2E-enal (449 mg, 1.35mmol) in DCM (20 ml) was treated with magnesium sulphate (2 g) and ethylamine (745 μl of a 2.0M solution in THF, 1.49 mmol). The reaction was stirred for 18 hours, filtered and concentrated under reduced pressure to provide the imine as a brown oil. The residue was resuspended in dry methanol (15 ml), cooled in an ice-salt bath and treated under an inert atmosphere with sodium borohydride (50 mg, 1.32 mmol). The reaction was stirred for 2 hours and solvent removed under reduced pressure. The residue was taken up in DCM and washed with saturated sodium bicarbonate. The organics were dried over anhydrous sodium sulphate, filtered and concentrated under reduced pressure to yield ethyl-[3-(6-[3-pyrrolidin-1-yl-1-{4-tolyl}-prop-1E-enyl]-pyridin-2-yl)-prop-2E-enyl}-amine as a brown oil (469 mg, 98%). $^1$H-NMR; δ (CDCl$_3$), 7.42 (1H, t, J=7.8 Hz), 7.20 (3H, m), 7.09 (3H, m), 6.94 (1H, dt, J=15.8, 6.0 Hz), 6.66 (2H, m), 3.49 (2H, dd, J=6.1, 1.4 Hz), 3.19 (2H, d, J=7.0 Hz), 2.74 (2H, q, J=7.1 Hz), 2.53 (4H, bs), 2.40 (3H, s), 1.77 (4H, m) and 1.16 (3H, t, J=7.1 Hz).

(b) N-Ethyl-4-(1H-2-methylimidazo[4,5-c]pyridin-1-ylmethyl)-N-{3-(6-[3-pyrrolidin- 1-yl-1-{4-tolyl}-prop-1E-enyl]-pyridin-2-yl)-prop-2E-enyl}-benzamide.

A solution of ethyl-{3-(6-[3-pyrrolidin-1-yl-1-{4-tolyl}-prop-1E-enyl]-pyridin-2-yl)-prop-2E-enyl}-amine (460 mg, 1.27 mmol), 4-(1H-2-methylimidazo[4,5-c]pyridin-1-ylmethyl)}benzoic acid sodium salt (368 mg, 1.27 mmol), EDC (360 mg, 1.91 mmol), N-methylmorpholine (279 μl, 2.54 mmol) and HOAt (20 mg) in DMF (15 ml) was stirred at room temperature for 96 hours. Solvent was removed under reduced pressure and the residue partitioned between DCM and saturated sodium bicarbonate solution. The organics were separated, dried over sodium sulphate, filtered and solvent removed under reduced pressure to leave a brown oil. The product was purified by column chromatography on silica-gel eluting with 5–10% methanol in DCM. Product containing fractions were combined and solvent removed to yield N-ethyl-4-(1H-2-methylimidazo[4,5-c]pyridin-1-ylmethyl)-N-{3-(6-[3-pyrrolidin-1-yl-1-{4-tolyl}prop-1E-enyl]-pyridin-2-yl)-prop-2E-enyl}-benzamide as a brown gum (365 mg, 47%). $^1$H-NMR; δ (CDCl$_3$), 9.02 (1H, s), 8.37 (1H, d, J=5.6 Hz), 7.45 (3H, m), 7.24–7.17 (4H, m), 7.07 (5H, m), 6.75–6.49 (3H, bm), 5.35 (2H, s), 4.36 (1H, bs), 4.04 (1H, bs), 3.58 (2H, m). 3.34 (2H, d, J=6.7 Hz), 2.72 (4H, bs), 2.60 (3H, s), 2.40 (3H, s), 1.84 (4H, bs) and 1.25–1.13 (3H, bm); $^{13}$C-NMR; δ 170.8, 153.6, 142.1, 142.0, 139.9, 137.5, 137.0, 136.4, 134.8, 129.6, 129.4, 127.6, 121.3, 104.9, 77.3, 54.4, 53.8, 50.8, 47.1, 23.5, 21.3 and 14.1.

EXAMPLE 14

(S)-4-Methyl-2-([4-(1H-2-methylimidazo[4,5-c] pyridin-1-ylmethyl)-benzoyl]-{3-[6-(3-pyrrolidin-1-yl-1-{4-tolyl}-prop-1E-enyl)-pyridin-2-yl]-prop-2E-enyl}-amino)-pentanoic acid ethyl ester

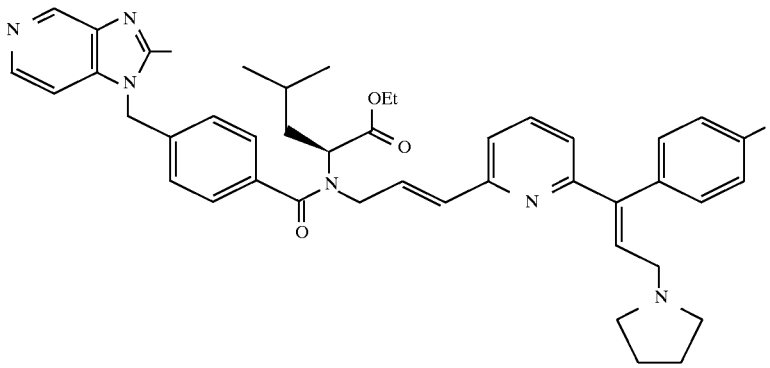

(a) (S)-4-Methyl-1-{3-(6-[3-pyrrolidin-1-yl-1-{4-tolyl}-prop-1E-enyl]-pyridin-2-yl)-prop-2E-enyl}-aminopentanoic acid ethyl ester.

A solution of 3-(6-[3-pyrrolidin-1-yl-1-{4-tolyl}-prop-1E-enyl]-pyridin-2-yl)-prop-2E-enal (420 mg, 1.26 mmol) in DCM (20 ml) was treated with powdered 3 Å molecular sieves (2 g) and L-leucine ethyl ester (221 mg, 1.39 mmol). The reaction was stirred for 120 hours, filtered and concentrated under reduced pressure to provide the imine as a brown oil. The residue was resuspended in dry methanol (15 ml), cooled in an ice-salt bath and treated under an inert atmosphere with sodium borohydride (50 mg, 1.31 mmol). The reaction was stirred for 2 hours and solvent removed under reduced pressure. The residue was taken up in DCM and washed with saturated sodium bicarbonate. The organics were dried over anhydrous sodium sulphate, filtered and concentrated under reduced pressure to yield (S)-4-methyl-1-{3-(6-[3-pyrrolidin-1-yl-1-{4-tolyl}-prop-1E-enyl]-pyridin-2-yl)-prop-2E-enyl}-aminopentanoic acid ethyl ester as a brown oil (585 mg, 94%). $^1$H-NMR; δ (CDCl$_3$), 7.42 (1H, t, J=7.8 Hz), 7.23–7.06 (6H, bm), 6.83–6.61 (3H, m), 4.20 (3H, m), 3.47–3.22 (2H, m), 3.18 (2H, d, J=6.9 Hz), 2.52 (4H, m), 2.41 (3H, s), 1.77 (4H, m), 1.51 (1H, t, J=7.2 Hz), 1.27 (5H, m) and 0.97–0.90 (6H, m).

(b) (S)-4-Methyl-2-([4-(1H-2-methylimidazo[4,5-c]pyridin-1-ylmethyl)-benzoyl]-{3-[6-(3-pyrrolidin-1-yl-1-{4-tolyl}-prop-1E-enyl)-pyridin-2-yl]-prop-2E-enyl}-amino)-pentanoic acid ethyl ester.

A solution of (S)-4-methyl-1-{3-(6-[3-pyrrolidin-1-yl-1-{4-tolyl}-prop-1E-enyl]-pyridin-2-yl)-prop-2E-enyl}-aminopentanoic acid ethyl ester (570 mg, 1.20 mmol), 4-(1H-2-methylimidazo[4,5-c]pyridin-1-ylmethyl)}benzoic acid dihydrochloride salt (408 mg, 1.20 mmol), EDC (345 mg, 1.80 mmol), N-methylmorpholine (264 μl, 2.40 mmol) and HOAt (20 mg) in DMF (10 ml) was stirred at room temperature for 8 days. Solvent was removed under reduced pressure and the residue partitioned between DCM and saturated sodium bicarbonate solution. The organics were dried over sodium sulphate, filtered and solvent removed under reduced pressure to leave a brown oil. The product was purified by column chromatography on silica-gel eluting with 5–12% methanol in DCM. Product containing fractions were combined and solvent removed to yield (S)-4-methyl-2-([4-(1H-2-methylimidazo[4,5-c]pyridin-1-ylmethyl)-benzoyl]-{3-[6-(3-pyrrolidin-1-yl-1-{4-tolyl}-prop-1E-enyl)-pyridin-2-yl]-prop-2E-enyl}-amino)-pentanoic acid ethyl ester as a brown oil (58 mg, 8%). $^1$H-NMR; δ (MeOD), 8.65 (1H, s), 8.08 (1H, d, J=5.6 Hz), 7.39 (1H, t, J=7.7 Hz), 7.33 (1H, d, J=5.6 Hz), 7.29 (1H, d, J=7.7 Hz), 7.25 (1H, d, J=7.8 Hz), 7.10–7.03 (4H, m), 6.96 (1H, d, J=7.9 Hz), 6.90 (1H, m), 6.82–6.74 (1H, m), 6.70 (1H, d, J=7.8 Hz), 6.61 (1H, d, J=7.6 Hz), 6.52 and 6.48 (1H, 2×s), 6.28 (1H, d, J=15.6 Hz), 5.42 and 5.39 (2H, 2×s), 4.47 and 4.16 (1H, 2×m), 3.96–3.91 (4H, m), 3.95 (1H, d, J=7.0 Hz), 3.93 (1H, d, J=7.0 Hz), 2.92 (2H, bs), 2.87 (2H, bs), 2.44 and 2.43 (3H, 2×s), 2.19 and 2.17 (3H, 2×s), 1.82–1.70 (4H, m), 1.61–1.53 (2H, m), 1.08–1.00 (4H, m), 0.76 and 0.74 (4H, 2×d, J=6.5 Hz), 0.52 (1H, d, J=6.3 Hz) and 0.39 (1H, d, J=6.2 Hz); $^{13}$C-NMR; δ (MeOD), 174.0, 172.6, 172.1, 158.0, 157.8, 156.8, 155.9, 155.2, 147.7, 147.5, 142.4, 141.1, 140.5, 139.3, 139.2, 139.1, 138.5, 127.2, 137.0, 135.4, 135.2, 133.8, 133.1, 131.4, 131.3, 130.6, 130.5, 128.6, 128.5, 128.3, 128.2, 124.2, 123.5, 122.6, 121.9, 107.5, 62.9, 62.4, 61.6, 58.2, 54.7, 52.4, 48.0, 46.4, 39.2, 39.1, 26.3, 25.4, 24.0, 23.4, 22.9, 22.4, 22.0, 21.3, 14.6, 14.4 and 13.9.

EXAMPLE 15

N-Benzyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide

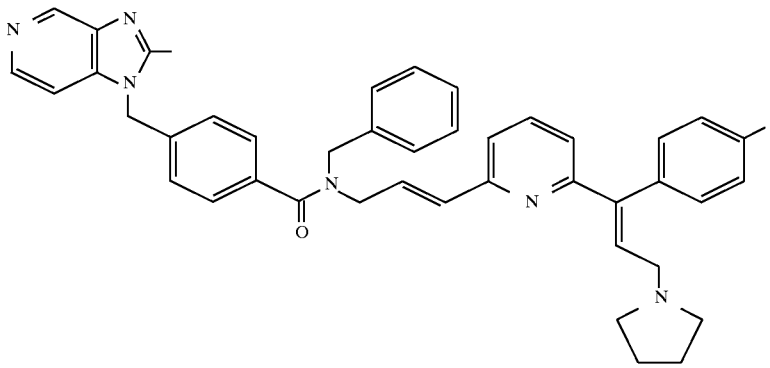

(a) Benzyl-{3-(6-[3-pyrrolidin-1-yl-1-{4-tolyl}-prop-1E-enyl]-pyridin-2-yl)-prop-2E-enyl}-amine.

A solution of 3-(6-[3-pyrrolidin-1-yl-1-{4-tolyl}-prop-1E-enyl]-pyridin-2-yl)-prop-2E-enal (500 mg, 1.50 mmol) in DCM (20 ml) was treated with powdered 3 Å molecular sieves (2.0 g) and benzylamine (181 μl, 1.65 mmol). The reaction was stirred for 18 hours, filtered and concentrated under reduced pressure to provide the imine as an oil. The residue was resuspended in dry methanol (15 ml), cooled in an ice-salt bath and treated under an inert atmosphere with sodium borohydride (57 mg, 1.49 mmol). The reaction was stirred for 2 hours and solvent removed under reduced pressure. The residue was taken up in DCM and washed with saturated sodium bicarbonate. The organics were dried over anhydrous sodium sulphate, filtered and concentrated under reduced pressure to yield benzyl-{3-(6-[3-pyrrolidin-1-yl-1-{4-tolyl}-prop-1E-enyl]-pyridin-2-yl)-prop-2E-enyl}-amine as a brown oil (658 mg, ~100%). $^1$H-NMR; δ (CDCl$_3$), 7.46–7.20 (14H, m), 6.99–6.91 (1H, m), 3.88 (2H, s), 3.52 (2H, dd, J=5.6 and 1.3 Hz), 3.20 (2H, d, J=7.0 Hz), 2.54 (4H, bs), 2.41 (2H, s) and 1.78 (4H, bs).

(b) N-Benzyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide.

A solution of benzyl-(E)-{3-(6-[3-pyrrolidin-1-yl-1-{4-tolyl}-prop-1E-enyl]-pyridin-2-yl-prop-2-enyl}-amine (645 mg, 1.52 mmol), 4-(1H-2-methylimidazo[4,5-c]pyridin-1-ylmethyl)}benzoic acid sodium salt (440 mg, 1.52 mmol), N-(3-dimethylaminopropyl)-N'-ethylcarbodiimide hydrochloride (437 mg, 2.28 mmol) and HOAt (20 mg) in DMF (20 ml) was stirred at room temperature for 48 hours. Solvent was removed under reduced pressure and the residue partitioned between DCM and brine. The organics were dried over sodium sulphate, filtered and solvent removed under reduced pressure to leave a brown foam. The product was purified by column chromatography on silica-gel eluting with 5–10% methanol in DCM. Product containing fractions were combined and solvent removed to yield N-benzyl-4-(1H-2-methylimidazo[4,5-c]pyridin-1-ylmethyl)-N-{3-(6-[3-pyrrolidin-1-yl-1-{4-tolyl}-prop-1E-enyl]-pyridin-2-yl)-prop-2E-enyl}-benzamide as an orange gum (245 mg, 24%). $^1$H-NMR; δ (CDCl$_3$), 9.02 (1H, s), 8.37 (1H, d, J=5.6 Hz), 7.49 (3H, m), 7.36 (4H, m), 7.22 (5H, m), 7.09 (5H, m), 6.74–6.49 (3H, m), 5.37 (2H, bs), 4.83 (1H, m), 4.59 (1H, m), 4.31 (1H, m), 3.98 (1H, m), 3.39 (2H, m), 2.77 (4H, m), 2.60 (3H, s), 2.41 (3H, s) and 1.87 (4H, m); $^{13}$C-NMR; δ (CDCl$_3$), 171.3, 156.8, 156.6, 154.1, 153.5, 153.3, 142.0, 141.8, 140.3, 139.7, 137.0, 136.8, 136.5, 136.3, 136.1, 134.5, 133.0, 131.8, 129.5, 129.3, 129.1, 128.9, 128.7, 128.3, 127.8, 127.6, 126.7, 126.3, 121.4, 121.2, 120.7, 120.2, 104.8, 54.2, 54.0, 53.6, 53.5, 51.9, 49.7, 47.6, 46.9, 46.4, 46.0, 29.6, 23.3, 21.2 and 14.0.

EXAMPLE 16

N-Propyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide

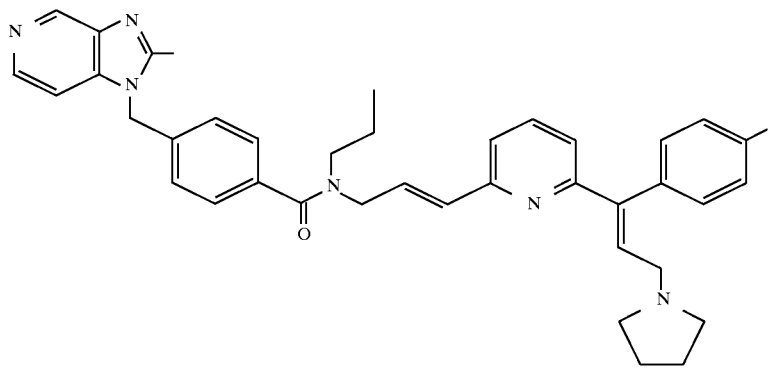

(a) Propyl)-{3-(6-[3-pyrrolidin-1-yl-1-{4-tolyl}-prop-1E-enyl]-pyridin-2-yl)-prop-2E-enyl}-amine.

A solution of 3-(6-[3-pyrrolidin-1-yl-1-{4-tolyl}-prop-1E-enyl]-pyridin-2-yl)-prop-2E-enal (500 mg, 1.50 mmol) in DCM (20 ml) was treated with anhydrous magnesium sulphate (2 g) and propylamine (136 μl, 1.65 mmol). The reaction was stirred for 18 hours, filtered and concentrated under reduced pressure to provide the imine as a brown oil. The residue was resuspended in dry methanol (15 ml), cooled in an ice-salt bath and treated under an inert atmosphere with sodium borohydride (55 mg, 1.45 mmol). The reaction was stirred for 2 hours and solvent removed under reduced pressure. The residue was taken up in DCM and washed with saturated sodium bicarbonate. The organics were dried over anhydrous sodium sulphate, filtered and concentrated under reduced pressure to yield propyl-{3-(6-[3-pyrrolidin-1-yl-1-{4-tolyl}-prop-1E-enyl]-pyridin-2-yl)-prop-2E-enyl}-amine as a brown oil (542 mg, 96%). $^{1}$H-NMR; δ (CDCl$_{3}$), 7.42 (1H, t, J=7.8 Hz), 7.23–7.07 (6H, m), 7.06–6.90 (1H, m), 6.69 (2H, m), 3.48 (2H, dd, J=6.1 and 1.3 Hz), 3.19 (2H, d, J=7.0 Hz), 2.66 (2H, t, J=7.2 Hz), 2.54 (4H, bs), 2.41 (3H, s), 1.80–1.75 (4H, m), 1.63–1.49 (2H, m), 0.96 (3H, t, J=7.4 Hz).

(b) N-Propyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide.

A solution of propyl-{3-(6-[3-pyrrolidin-1-yl-1-{4-tolyl}-prop-1E-enyl]-pyridin-2-yl-prop-2E-enyl}-amine (530 mg, 1.41 mmol), 4-(1H-2-methylimidazo[4,5-c]pyridin-1-ylmethyl)}benzoic acid sodium salt (408 mg, 1.41 mmol), EDC (406 mg, 2.12 mmol) and HOAt (20 mg) in DMF (20 ml) was stirred at room temperature for 48 hours. Solvent was removed under reduced pressure and the residue partitioned between DCM and brine. The organics were dried over sodium sulphate, filtered and solvent removed under reduced pressure to leave a brown foam. The product was purified by column chromatography on silica-gel eluting with 5–10% methanol in DCM. Product containing fractions were combined and solvent removed to yield N-propyl-4-(1H-2-methylimidazo[4,5-c]pyridin-1-ylmethyl)-N-{3-(6-[3-pyrrolidin-1-yl-1-{4-tolyl}-prop-1E-enyl]-pyridin-2-yl)-prop-2E-enyl}-benzamide as an orange foam (308 mg, 35%). $^{1}$H-NMR; δ (CDCl$_{3}$), 9.02 (1H, s), 8.38 (1H, d, J=5.4 Hz), 7.45 (3H, m), 7.24–7.06 (9H, bm), 6.75–6.48 (3H, bm), 5.36 (2H, s), 4.36 (1H, m), 4.05 (1H, m), 3.52 (1H, m), 3.38 (2H, d, J=6.6 Hz), 3.23 (1H, m), 2.77 (4H, bs), 2.60 (3H, s), 2.40 (3H, s), 1.87 (4H, bs), 1.69 (2H, m), and 0.97–0.75 (3H, m); $^{13}$C-NMR; δ (CDCl$_{3}$), 171.0, 156.9, 153.6, 142.0, 141.9, 140.3, 139.8, 137.4, 137.0, 136.8, 136.3, 134.6, 132.7, 131.4, 129.7, 129.5, 129.3, 127.7, 127.5, 126.3, 121.3, 121.2, 120.7, 120.1, 104.9, 54.3, 54.1, 53.7, 50.7, 50.3, 47.0, 46.9, 46.1, 23.4, 21.7, 21.2, 20.4, 14.0, 11.3 and 11.0.

EXAMPLE 17

N-Cyclohexyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-propyl}-benzamide A solution of N-cyclohexyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide (300 mg, 0.45 mmol) in methanol (15 ml) was stirred vigorously in the presence of a palladium catalyst (30 mg, 10% on charcoal) under an atmosphere of hydrogen gas for 18 hours. The catalyst was removed by filtration and solvent removed under reduced pressure. The product was purified by preparative HPLC using C-18 silica and eluting with 85% methanol, 15% 0.01M di-ammonium hydrogen phosphate buffer. Product containing fractions were combined and solvent removed. The residue was taken up in DCM and washed with saturated sodium bicarbonate solution and water. The organic layer was dried over magnesium sulphate, filtered and concentrated under reduced pressure to provide N-cyclohexyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-propyl}-benzamide as an off-white foam (58 mg, 19%). $^{1}$H-NMR; δ (CDCl$_{3}$), 9.03 (1H, s), 8.37 (1H, bs), 7.44–7.38 (4H, m), 7.34–7.02 (8H, m), 6.66 (1H, d, J=7.8 Hz), 5.35 (2H, s), 3.48–3.28 (2H, bm), 3.18 (2H, d, J=7.0 Hz), 2.93–2.83 (1H, bm), 2.63–0.88 (14H, m), 2.60 (3H, s), 2.58–2.52 (4H, bm), 2.39 (3H, s) and 1.80–1.74 (4H, bm); $^{13}$C-NMR; δ (CDCl$_{3}$), 147.0, 135.6, 133.7, 130.3, 129.9, 129.1, 123.2, 122.9, 122.5, 120.6, 119.9, 114.4, 113.1, 98.4, 52.5, 48.2, 47.6, 40.6, 35.2, 29.6, 25.2, 22.4, 19.2, 18.5, 17.0, 14.8 and 7.6.

EXAMPLE 18

N-Cyclopropyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide

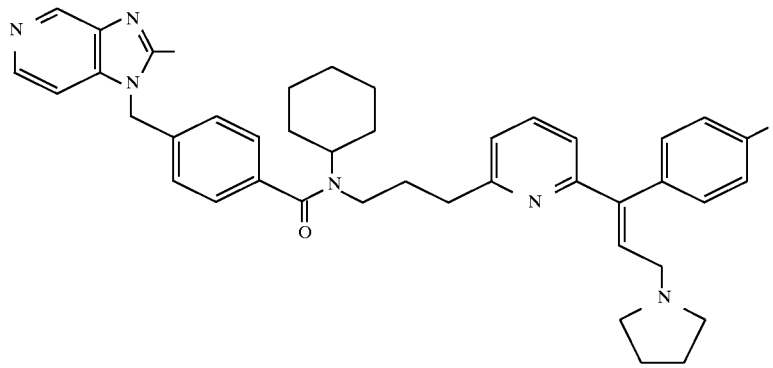

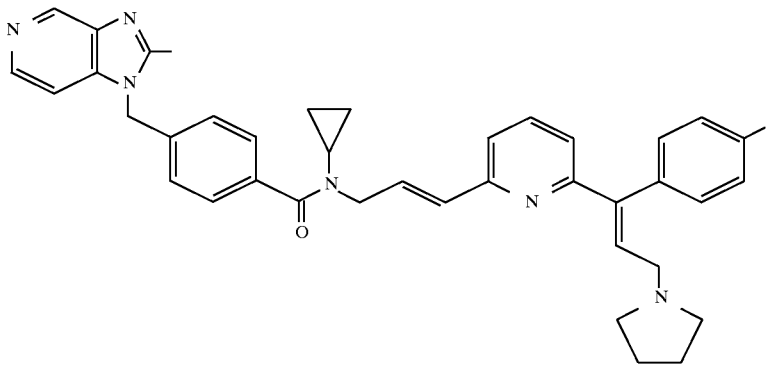

(a) Cyclopropyl-{3-(6-[3-pyrrolidin-1-yl-1-{4-tolyl}-prop-1E-enyl]-pyridin-2-yl)-prop-2E-enyl}-amine.

A solution of 3-(6-[3-pyrrolidin-1-yl-1-{4-tolyl}-prop-1E-enyl]-pyridin-2-yl)-prop-2E-enal (241 mg, 0.73 mmol) in DCM (15 ml) was treated with powdered 3 Å molecular sieves (2 g) and cyclopropylamine (100 μl, 1.44 mmol). The reaction was stirred for 18 hours, filtered and concentrated under reduced pressure to provide the imine as a brown oil. The residue was resuspended in dry methanol (10 ml), cooled in an ice-salt bath and treated under an inert atmosphere with sodium borohydride (30 mg, 0.73 mmol). The reaction was stirred for 2 hours and solvent removed under reduced pressure. The residue was taken up in DCM and washed with saturated sodium bicarbonate. The organics were dried over magnesium sulphate, filtered and concentrated under reduced pressure to yield cyclopropyl-{3-(6-[3-pyrrolidin-1-yl-1-{4-tolyl}-prop-1E-enyl]-pyridin-2-yl)-prop-2E-enyl}-amine as a pale brown oil (228 mg, 84%). $^1$H-NMR; δ (CDCl$_3$), 7.39 (1H, t, J=7.7 Hz), 7.22–7.17 (3H, m), 7.10–7.03 (3H, m), 6.93 (1H, dt, J=15.6, 6.2 Hz), 6.66 (1H, d, J=15.6 Hz), 6.60 (1H, d, J=15.6 Hz), 3.52 (2H, d, J=5.8 Hz), 3.17 (2H, d, J=6.9 Hz), 2.56–2.47 (4H, m), 2.38 (3H, s), 2.28–2.20 (1H, m), 1.78–1.71 (4H, m), 0.50–0.36 (4H, m).

(b) N-Cyclopropyl-4-(1H-2-methylimidazo[4,5-c]pyridin-1-ylmethyl)-N-{3-(6-[3-pyrrolidin-1-yl-1-{4-tolyl}-prop-1E-enyl]-pyridin-2-yl)-prop-2E-enyl}-benzamide.

A solution of cyclopropyl-{3-(6-[3-pyrrolidin-1-yl-1-{4-tolyl}-prop-1E-enyl]-pyridin-2-yl)-prop-2E-enyl}-amine (228 mg, 0.61 mmol), 4-(1H-2-methylimidazo[4,5-c]pyridin-1-ylmethyl)benzoic acid sodium salt (212 mg, 0.73 mmol), EDC (175 mg, 0.92 mmol) and HOAt (10 mg) in DMF (15 ml) was stirred at room temperature for 120 hours. Solvent was removed under reduced pressure and the residue partitioned between DCM and brine. The organics were dried over magnesium sulphate, filtered and solvent removed under reduced pressure to leave a brown foam. The product was purified by column chromatography on silica-gel eluting with 10–25% methanol in DCM. Product containing fractions were combined and solvent removed to yield N-cyclopropyl-4-(1H-2-methylimidazo[4,5-c]pyridin-1-ylmethyl)-N-{3-(6-[3-pyrrolidin-1-yl-1-{4-tolyl}-prop-1E-enyl]-pyridin-2-yl)-prop-2E-enyl}-benzamide as a brown foam (174 mg, 46%). $^1$H-NMR; δ (CDCl$_3$), 9.00 (1H, s), 8.34 (1H, d, J=5.5 Hz), 7.54 (2H, d, J=7.8 Hz), 7.44 (1H, t, J=7.8 Hz), 7.30–7.13 (5H, m), 7.08 (2H, d, J=7.8 Hz), 7.05 (2H, d, J=7.8 Hz), 6.98–6.85 (1H, m), 6.70 (1H, d, J=7.8 Hz), 6.70–6.62 (1H, m), 5.3 (2H, s), 4.33 (2H, bs), 3.51 (2H, d, J=7.2 Hz), 3.00–2.88 (5H, bm), 2.57 (3H, s), 2.38 (3H, s), 1.97–1.90 (4H, m) and 0.70–0.45 (4H, bm); $^{13}$C-NMR; δ (CDCl$_3$), 155.9, 154.1, 153.3, 145.2, 141.8, 141.6, 140.1, 139.6, 137.5, 137.1, 136.1, 133.9, 131.7, 130.0, 129.2, 129.1, 128.0, 125.8, 123.4, 121.0, 120.4, 105.7, 53.0, 46.9, 23.2, 21.0, 13.9 and 9.8.

EXAMPLE 19

(R,S)-4-(1H-2-Methylimidazo[4,5-c]pyridin-1-ylmethyl)benzoic acid 3-[6-(3-pyrrolidin-1-yl-1-{4-tolyl}-prop-1E-enyl)-pyridin-2-yl]but-3E-en-2-yl ester

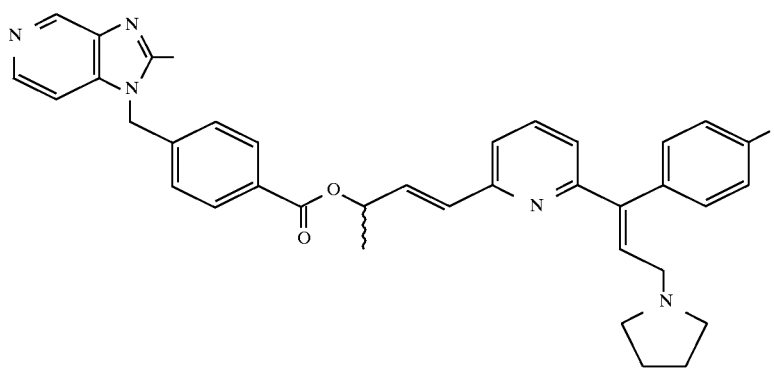

(a) 4-(6-[3-Pyrrolidin-1-yl-1-{4-tolyl}-prop-1E-enyl]-pyridin-2-yl)-but-3E-en-2ol.

A stirred solution of 3-(6-[3-pyrrolidin-1-yl-1-{4-tolyl}-prop-1E-enyl]-pyridin-2-yl)-prop-2E-enal (1.41 g, 4.24 mmol) in anhydrous THF (50 ml) at −78° C. was treated dropwise with a solution of methyl magnesium bromide (1.56 ml, 3.0M in diethylether, 4.67 mmol). The reaction mixture was allowed to warm slowly to room temperature (~2 hours). The reaction was quenched with water (3 ml) and THF removed under reduced pressure. The residue was taken up in 1M HCl and then basified with solid sodium bicarbonate to pH 8. The product was extracted with ethyl acetate (×3). The organics were combined, dried over sodium sulphate, filtered and concentrated under reduced pressure. The product was purified by column chromatography eluting with 5% methanol in DCM. Product containing fractions were combined and solvent removed to provide 4-(6-[3-pyrrolidin-1-yl-1-{4-tolyl}-prop-1E-enyl]-pyridin-2-yl)-but-3E-en-2-ol as a pale brown foam (544 mg, 37%). $^1$H-NMR; δ (CDCl$_3$), 7.43 (1H, t, J=7.8 Hz), 7.24–7.18 (3H, m), 7.11–7.06 (3H, m), 6.94 (1H, dd, J=15.6 and 5.8 Hz), 6.71–6.64 (2H, m), 4.60–4.55 (1H, m), 3.23 (2H, d, J=7.0 Hz), 2.58 (4H, bs), 2.41 (3H, s), 1.82–1.77 (4H, m), 1.41 (3H, d, J=6.5 Hz).

(b) (R,S)-4-(1H-2-Methylimidazo[4,5-c]pyridin-1-ylmethyl)benzoic acid 4-[6-( 3-pyrrolidin-1-yl-1-{4-tolyl}-prop-1E-enyl)-pyridin-2-yl]but-3E-en-2-yl ester.

A solution of 4-(6-[3-pyrrolidin-1-yl-1-{4-tolyl}-prop-1E-enyl]-pyridin-2-yl)-but-3-en-2E-ol (510 mg, 1.46 mmol) in DCM (15 ml) was treated with 4-(1H-2-methylimidazo[4,5-c]pyridin-1-ylmethyl)benzoic acid sodium salt (466 mg, 1.61 mmol), EDC (420 mg, 2.19mmol) and DMAP (20 mg). The reaction mixture was stirred for 96 hours at room temperature. The reaction mixture was partitioned between DCM and saturated sodium bicarbonate solution. The organic layer was separated, dried over magnesium sulphate, filtered and concentrated under reduced pressure. The product was purified by column chromatography eluting with 4% methanol/DCM. Product containing fractions were combined and solvent removed to yield (R,S)-4-(1H-2-methylimidazo[4,5-c]pyridin-1-ylmethyl)benzoic acid 4-[6-(3-pyrrolidin-1-yl-1-{4-tolyl}-prop-1E-enyl)-pyridin-2-yl]but-3E-en-2-yl ester as an off-white foam (93 mg, 11%). $^1$H-NMR; δ (CDCl$_3$), 9.04 (1H, s), 8.38 (1H, d, J=5.6 Hz), 8.08 (2H, d, J=8.3 Hz), 7.43 (1H, t, J=7.8 Hz), 7.25–7.06 (9H, m), 6.96 (1H, dd, J=6.2, 15.6 Hz), 6.71 (2H, m), 5.83 (1H, m), 5.40 (2H, s), 3.27 (2H, d, J=7.1 Hz), 2.64 (4H, bs), 2.60 (3H, s), 2.40 (3H, s), 1.81 (4H, bs) and 1.56 (3H, d, J=6.6 Hz); $^{13}$C-NMR; δ (CDCl$_3$), 159.8, 151.9, 148.4, 148.3, 137.2, 136.8, 136.6, 135.1, 134.6, 131.9, 131.5, 129.8, 127.9, 125.8, 125.4, 124.4, 124.0, 123.5, 121.0, 116.0, 115.4, 99.6, 66.2, 49.3, 48.7, 41.9, 18.2, 16.0, 15.2 and 6.8.

EXAMPLE 20

N-Cyclohexyl-4-(1H-2-methylimidazo[4,5-c]pyridin-1-ylmethyl)-N-{3-[6-(3-pyrrolidin-1-yl-1-{4-chlorophenyl}-prop-1E-enyl)-pyridin-2-yl]-prop-2E-enyl}-benzamide

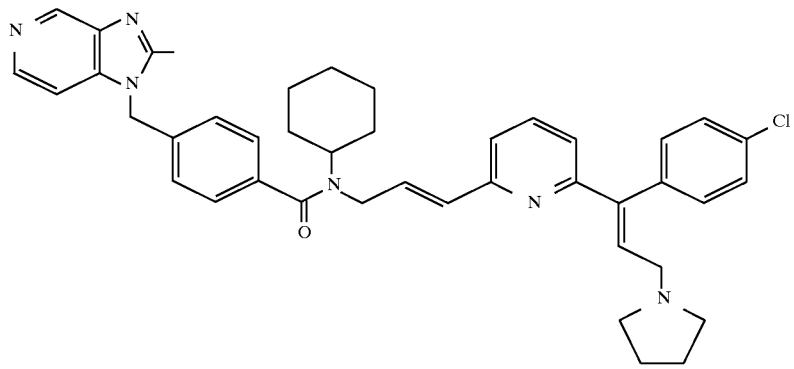

(a) 3-(6-[3-Pyrrolidin-1-yl-1-{4-chlorophenyl}-prop-1E-enyl]-pyridin-2-yl)-prop-2E-enal.

(3-(6-[3-Pyrrolidin-1-yl-1-{4-chlorophenyl}-prop-1E-enyl]-pyridin-2-yl)-prop-2E-enal was prepared using chemistry similar to that used to prepare 3-(6-[3-pyrrolidino-1-{4-tolyl}-prop-1E-enyl]-pyridin-2-yl)-prop-2E-enal (example 3a). $^1$H-NMR; δ (CDCl$_3$), 9.79 (1H, dd, J=7.8, 2.0 Hz), 7.75 (1H, t, J=7.7 Hz), 7.70–7.34 (4H, m), 7.25–7.09 (4H, m), 6.94 (1H, d, J=7.8 Hz), 3.17 (2H, d, J=7.0 Hz), 2.52 (4H, bs), 1.83–1.72 (4H, m).

(b) Cyclohexyl-{3-(6-[3-pyrrolidino-1-{4-chlorophenyl}-prop-1E-enyl]-pyridin-2-yl)-prop-2E-enyl}-amine.

A solution of 3-(6-[3-pyrrolidin-1-yl-1-{4-chlorophenyl}-prop -1E-enyl]-pyridin-2-yl)-prop-2E-enal (252 mg, 0.69 mmol) in DCM (15 ml) was treated with activated powdered 3 Å molecular sieves (2 g) and cyclohexylamine (75 mg, 0.76 mmol). The reaction was stirred for 18 hours, filtered and concentrated under reduced pressure to provide the imine as a brown oil. The residue was resuspended in dry methanol (10 ml), cooled in an ice-salt bath and treated under an inert atmosphere with sodium borohydride (25 mg, 6.55 mmol). The reaction was stirred for 2.5 hours and solvent removed under reduced pressure. The residue was taken up in DCM (10 ml) and washed with brine. The organics were dried over magnesium sulphate, filtered and concentrated to yield cyclohexyl-{3-(6-[3-pyrrolidin-1-yl-1-{4-chlorophenyl}-prop-1E-enyl]-pyridin-2-yl)-prop-2E-enyl}-amine as a yellow oil (280 mg, 96%). $^1$H-NMR; δ (CDCl$_3$), 7.70–7.34 (3H, m), 7.22–7.09 (4H, m), 6.99–6.84 (1H, m), 6.70–6.59)2H, m), 3.52 (2H, dd, J=6.0 and 1.0 Hz), 3.25 (1H, m), 3.16 (2H, d, J=7.0 Hz), 2.54 (4H, bs), 1.97–1.93 (2H, m), 1.80–1.75 (5H, m), 1.74–1.72 (1H, m), 1.30–1.18 (6H, m).

(c) N-Cyclohexyl-4-(1H-2-methylimidazo[4,5-c]pyridin-1-ylmethyl)-N-{3-[6-(3-pyrrolidin-1-yl-1-{4-chlorophenyl}-prop-1E-enyl)-pyridin-2-yl]-prop-2E-enyl}-benzamide.

A solution of cyclohexyl-{3-(6-[3-pyrrolidin-1-yl-1-{4-p-chlorophenyl}-prop-1E-enyl]-pyridin-2-yl)-prop-2E-enyl}-amine (280 mg, 0.66 mmol), 4-(1H-2-methylimidazo[4,5-c]pyridin-1-ylmethyl)benzoic acid sodium salt (231 mg, 0.80 mmol), EDC (153 mg, 0.80 mmol) and HOAt (20 mg) in DMF (15 ml) was stirred at room temperature for 96 hours. Solvent was removed under reduced pressure and the residue partitioned between DCM and brine. The organics were dried over magnesium sulphate, filtered and solvent removed under reduced pressure to leave a brown foam. The product was purified by column chromatography on silica-gel eluting with 5–20% methanol in DCM. Product containing fractions were combined and solvent removed to yield N-cyclohexyl-4-(1H-2-methylimidazo[4,5-c]pyridin-1-ylmethyl)-N-{3-(6-[3-pyrrolidin-1-yl-1-{4-chlorophenyl}-prop-1E-enyl]-pyridin-2-yl)-prop-2E-enyl}-benzamide as a white foam (190 mg, 42%). $^1$H-NMR; δ (CDCl$_3$), 8.97 (1H, s), 8.31 (1H, d, J=5.2 Hz), 7.42 (1H, t, J=7.8 Hz), 7.37–7.32 (4H, m), 7.15–7.04 (6H, m) 6.72–6.30 (3H, m), 5.25 (2H, s), 4.34–4.19 (2H, m), 2.84–2.55 (3H, m), 3.41–3.38 (3H, m), 2.84 (4H, bs), 2.55 (3H, s) 1.86–1.50 (10H, m) and 0.99 (2H, m); $^{13}$C-NMR; δ (CDCl$_3$), 153.6, 142.1, 140.4, 139.9, 136.9, 136.0, 135.8, 134.0, 132.4, 131.8, 131.2, 131.0, 129.0, 127.3, 126.5, 126.2, 120.8, 120.4, 104.9, 59.1, 54.8, 53.5, 47.1, 43.2, 31.9, 30.8, 25.9, 25.7, 25.0, 23.4 and 14.1.

EXAMPLE 21

N-4-Tetrahydropyranyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide

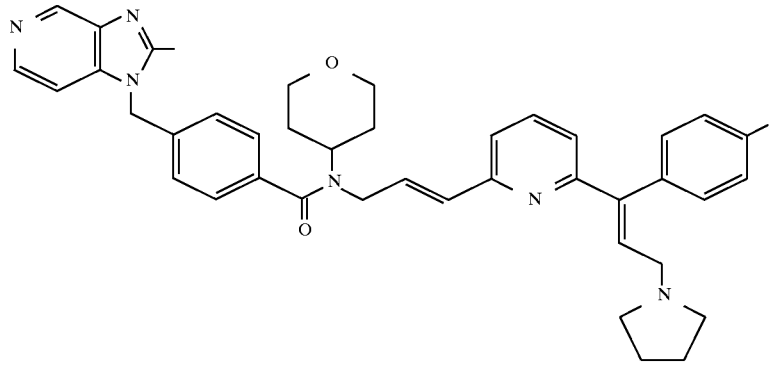

(a) 4-Amino-tetrahydropyran

A mixture of tetrahydropyranone (1.0 g, 10.0 mmol), ammonium acetate (7.69 g, 100.0 mmol), 3 Å molecular sieve powder (2.5 g) and sodium cyanoborohydride (1.25 g, 20.0 mmol) suspended in dry methanol (50 ml) under a blanket of argon was refluxed for 2 hours and allowed to cool to room temperature. The suspension was filtered and concentrated under reduced pressure. The residue was partitioned between DCM and water. The organic layer was extracted with 1M HCl (×2). The combined extracts were basified with 5M sodium hydroxide solution and extracted with DCM. The combined organics were dried over magnesium sulphate, filtered and concentrated under reduced pressure to yield 4-amino-tetrahydropyran as a colourless oil (120 mg, 12%). $^1$H-NMR; δ (CDCl$_3$), 3.95–3.86 (2H, m), 3.38–3.27 (2H, m), 2.85–2.73 (1H, m), 1.79–1.67 (2H, m), 1.40–1.24 (2H, m).

(b) 4-Tetrahydropyranyl-{3-(6-[3-pyrrolidin-1-yl-1-{4-tolyl}-prop-1E-enyl]-pyridin-2-yl)-prop-2E-enyl}-amine.

A solution of 3-(6-[3-pyrrolidin-1-yl-1-{4-tolyl}-prop-1E-enyl]-pyridin-2-yl)-prop-2E-enal (400 mg, 1.20 mmol) in DCM (20 ml) was treated with powdered 3 Å molecular sieves (3 g) and 4-amino-tetrahydropyran (200 mg, 2.0 mmol). The reaction was stirred for 18 hours, filtered and concentrated under reduced pressure to provide the imine as a brown oil. The residue was resuspended in dry methanol (15 ml), cooled in an ice-salt bath and treated under an inert atmosphere with sodium borohydride (45 mg, 1.19 mmol). The reaction was stirred for 2 hours and solvent removed under reduced pressure. The residue was taken up in DCM and washed with saturated sodium bicarbonate. The organics were dried over anhydrous sodium sulphate, filtered and concentrated under reduced pressure to yield an impure mixture containing 4-tetrahydropyranyl)-{3-(6-[3-pyrrolidin-1-yl-1-{4-tolyl}-prop-1E-enyl]-pyridin-2-yl)-prop-2E-enyl}-amine as a brown oil which was used without purification in the coupling step 21(c).

(c) N-4-Tetrahydropyranyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide.

A solution of 4-tetrahydropyranyl)-{3-(6-[3-pyrrolidin-1-yl-1-{4-tolyl}-prop-1E-enyl]-pyridin-2-yl)-prop-2E-enyl}-amine (crude), 4-(1H-2-methylimidazo[4,5-c]pyridin-1-ylmethyl)}benzoic acid sodium salt (382 mg, 1.32 mmol), EDC (345 mg, 1.80 mmol) and HOAt (8 mg) in DMF (10 ml) was stirred at room temperature for 96 hours. Solvent was removed under reduced pressure and the residue partitioned between DCM and brine. The organics were dried over sodium sulphate, filtered and solvent removed under reduced pressure to leave a brown foam. The product was purified by column chromatography on silica-gel eluting with 10–25% methanol in DCM. Product containing fractions were combined and solvent removed to yield N-4-tetrahydropyranyl-4-(1H-2-methylimidazo[4,5-c]pyridin-1-ylmethyl)-N-(3-[6-(3-pyrrolidin-1-yl-1-{4-tolyl}-prop-1E-enyl)-pyridin-2-yl]-prop-2E-enyl}-benzamide as a brown foam (145 mg, 16%). $^1$H-NMR; δ (CDCl$_3$), 9.02 (1H, s), 8.37 (1H, s), 7.43 (1H, t, J=7.8 Hz), 7.40 (2H, bs), 7.22–6.39 (8H, bm), 7.21 (2H, d, J=7.9 Hz), 7.07 (2H, d, J=7.9 Hz), 5.36 (2H, bs), 4.70–3.14 (9H, bm), 2.66 (4H, bs), 2.59 (3H, bs), 2.39 (3H, s), 2.00–1.88 (2H, m), 1.82 (4H, bs) and 1.81–1.59 (2H, m); $^{13}$C-NMR; δ (CDCl$_3$), 153.5, 148.1, 142.1, 142.0, 140.3, 139.8, 137.2, 136.8, 136.2, 134.9, 131.4, 129.6, 129.2, 127.3, 126.3, 121.1, 120.1, 104.8, 67.5, 54.5, 53.9, 47.0, 23.4, 21.2 and 14.0.

EXAMPLE 22

N-Butyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide

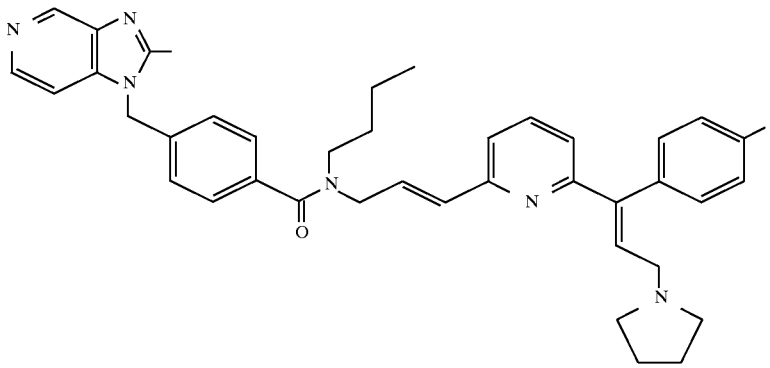

(a) Butyl-{3-(6-[3-pyrrolidin-1-yl-1-{4-tolyl}-prop-1E-enyl]-pyridin-2-yl)-prop-2E-enyl}-amine.

A solution of (E)-3-(6-[3-pyrrolidino-1-{4-tolyl}-prop-1E-enyl]-pyridin-2-yl)-prop-2E-enal (458 mg, 1.38 mmol) in DCM (20 ml) was treated with anhydrous magnesium sulphate (2 g) and butylamine (150 µl, 1.52 mmol). The reaction was stirred for 18 hours, filtered and concentrated under reduced pressure to provide the imine as a brown oil. The residue was resuspended in dry methanol (15 ml), cooled in an ice-salt bath and treated under an inert atmosphere with sodium borohydride (53 mg, 1.39 mmol). The reaction was stirred for 2 hours and solvent removed under reduced pressure. The residue was taken up in DCM and washed with saturated sodium bicarbonate. The organics were dried over anhydrous sodium sulphate, filtered and concentrated under reduced pressure to yield butyl-{3-(6-[3-pyrrolidin-1-yl-1-{4-tolyl}-prop-1E-enyl]-pyridin-2-yl)-prop-2E-enyl}-amine as a brown oil (517 mg, 96%). $^1$H-NMR; δ (CDCl$_3$), 7.42 (1H, t, J=7.8 Hz), 7.23–7.17 (6H, m), 6.98–6.87 (1H, m), 6.70–6.60 (2H, m), 3.48 (2H, dd, J=6.0 and 1.2 Hz), 3.19 (2H, d, J=7.0 Hz), 2.69 (2H, t, J=7.0 Hz), 2.54 (4H, bs), 2.41 (3H, s), 1.80–1.75 (4H, m), 1.59–1.45 (2H, m), 1.42–1.26 (2H, m), 0.94 (3H, t, J=7.2 Hz).

(b) N-Butyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide.

A solution of butyl-{3-(6-[3-pyrrolidino-1-{4-tolyl}-prop-1E-enyl]-pyridin-2-yl)-prop-2E-enyl}-amine (502 mg, 1.29 mmol), 4-(1H-2-methylimidazo[4,5-c]pyridin-1-ylmethyl)benzoic acid sodium salt (411 mg, 1.42 mmol), EDC (372 mg, 1.94 mmol) and HOAt (20 mg) in DMF (15 ml) was stirred at room temperature for 48 hours. Solvent was removed under reduced pressure and the residue partitioned between DCM and brine. The organics were dried over sodium sulphate, filtered and solvent removed under reduced pressure to leave a brown foam. The product was purified by column chromatography on silica-gel eluting with 5–10% methanol in DCM. Product containing fractions were combined and solvent removed to yield N-butyl-4-(1H-2-methylimidazo[4,5-c]pyridin-1-ylmethyl)-N-{3-(6-[3-pyrrolidin-1-yl-1-{4-tolyl}-prop-1E-enyl]-pyridin-2-yl)-prop-2E-enyl}-benzamide as an orange foam (413 mg, 50%). $^1$H-NMR; δ (CDCl$_3$), 9.03 (1H, s), 8.38 (1H, d, J=5.6 Hz), 7.45 (3H, m), 7.24–7.04 (9H, m), 6.74 (3H, bm), 5.36 (2H, s), 4.35 (0.8H, bs), 4.04 (1.2H, s), 3.56 (2H, m), 3.28 (2H, d, J=7.0 Hz), 2.62 (7H, m), 2.40 (3H, s), 1.82 (4H, bs) and 1.66–0.76 (7H, bm); $^{13}$C-NMR; δ (CDCl$_3$), 170.9, 157.1, 153.5, 153.3, 142.7, 142.0, 141.9, 140.3, 139.8, 137.2, 136.9, 136.3, 134.9, 132.8, 131.5, 129.6, 129.2, 127.5, 126.3, 121.2, 120.5, 120.0, 104.9, 54.5, 53.9, 50.7, 48.4, 47.0, 46.1, 45.0, 30.5, 29.3, 23.4, 21.3, 20.2, 19.7, 14.0, 13.9 and 13.6.

EXAMPLE 23

N-Pentyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide

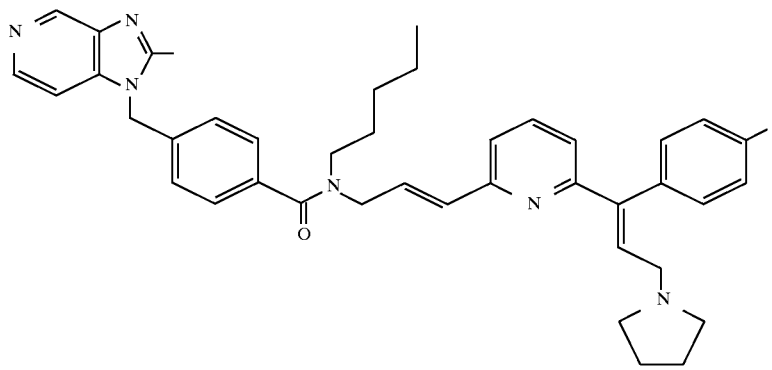

(a) Pentyl-{3-(6-[3-pyrrolidin-1-yl-1-{4-tolyl}-prop-1E-enyl]-pyridin-2-yl)-prop-2E-enyl}-amine.

A solution of 3-(6-[3-pyrrolidin-1-yl-1-{4-tolyl}-prop-1E-enyl]-pyridin-2-yl)-prop-2E-enal (1.11 g, 3.34 mmol) in DCM (50 ml) was treated with anhydrous magnesium sulphate (5 g) and pentylamine (465 µl, 4.01 mmol). The reaction was stirred for 18 hours, filtered and concentrated under reduced pressure to provide the imine as a brown oil. The residue was resuspended in dry methanol (15 ml), cooled in an ice-salt bath and treated under an inert atmosphere with sodium borohydride (133 mg, 3.51 mmol). The reaction was stirred for 2 hours and solvent removed under reduced pressure. The residue was taken up in DCM and washed with saturated sodium bicarbonate. The organics were dried over sodium sulphate, filtered and concentrated under reduced pressure to yield pentyl-{3-(6-[3-pyrrolidin-1-yl-1-{4-tolyl}-prop-1E-enyl]-pyridin-2-yl)-prop-2E-enyl}-amine as a brown oil (1.38 g, 94%). The amine was used directly in the coupling reaction 23(b).

(b) N-Pentyl-4-(1H-2-methylimidazo[4,5-c]pyridin-1-ylmethyl)-N-{3-(6-[3-pyrrolidin-1-yl-1-{4-tolyl}-prop-1E-enyl]-pyridin-2-yl)-prop-2E-enyl}-benzamide.

A solution of pentyl-{3-(6-[3-pyrrolidin-1-yl-1-{4-tolyl}-prop-1E-enyl]-pyridin-2-yl)-prop-2E-enyl}-amine (1.28 g, 3.17 mmol), 4-(1H-2-methylimidazo[4,5-c]pyridin-1-ylmethyl)benzoic acid sodium salt (1.26 g, 3.45 mmol), EDC (911 mg, 4.76 mmol) and HOAt (10 mg) in DMF (15 ml) was stirred at room temperature for 120 hours. Solvent was removed under reduced pressure and the residue partitioned between DCM and brine. The organics were dried over magnesium sulphate, filtered and solvent removed under reduced pressure to leave a brown gum. The product was purified by column chromatography on silica-gel eluting with 10% methanol in DCM. Product containing fractions were combined and solvent removed to yield N-pentyl-4-(1H-2-methylimidazo[4,5-c]pyridin-1-ylmethyl)-N-{3-(6-[3-pyrrolidin-1-yl-1-{4-tolyl}-prop-1E-enyl]-pyridin-2-yl)-prop-2E-enyl}-benzamide as a brown foam (589 mg, 28%). $^1$H-NMR; δ (MeOD), 9.00 (1H, s), 8.35 (1H, d, J=5.5 Hz), 7.45 (3H, m), 7.11 (9H, m), 6.56 (3H, m), 5.33 (2H, s), 4.33 (0.8H, m), 4.02 (1.2H, m), 3.51 (0.8H, m), 6.23 (3.2H, m), 2.57 (7H, s), 2.37 (3H, s), 1.77 (4H, m) and 1.20 (9H, m); $^{13}$C-NMR; δ (MeOD), 169.3, 154.8, 152.8, 150.8, 140.5, 138.4, 138.2, 137.2, 136.6, 134.7, 134.4, 133.7, 132.3, 129.5, 126.8, 126.3, 125.2, 124.7, 124.5, 124.2, 117.5, 117.4, 116.3, 103.5, 51.5, 50.9, 48.3, 46.4, 42.8, 26.3, 25.7, 25.2, 24.0, 20.2, 19.5, 19.0, 17.4, 10.4 and 9.9.

EXAMPLE 24

N-Nonyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide (a) Nonyl-{3-(6-[3-pyrrolidin-1-yl-1-{4-tolyl}-prop-1E-enyl]-pyridin-2-yl)-prop-2E-enyl}-amine.

A solution of 3-(6-[3-pyrrolidin-1-yl-1-{4-tolyl}-prop-1E-enyl]-pyridin-2-yl)-prop-2E-enal (319 mg, 0.96 mmol) in DCM (15 ml) was treated with powdered 3 Å molecular sieves (1.5 g) and nonylamine (211 μl, 1.15 mmol). The reaction was stirred for 18 hours, filtered and concentrated under reduced pressure to provide the imine as a yellow oil. The residue was resuspended in dry methanol (15 ml), cooled in an ice-salt bath and treated under an inert atmosphere with sodium borohydride (36 mg, 0.95 mmol). The reaction was stirred for 2 hours and solvent removed under reduced pressure. The residue was taken up in DCM and washed with saturated sodium bicarbonate. The organics were dried over anhydrous sodium sulphate, filtered and concentrated under reduced pressure to yield nonyl-{3-(6-[3-pyrrolidin-1-yl-1-{4-tolyl}-prop-1E-enyl]-pyridin-2-yl)-prop-2E-enyl}-amine as a brown oil (462 mg, contaminated with excess nonylamine). $^1$H-NMR; δ (CDCl$_3$), 7.42 (1H, t, J=7.7 Hz), 7.23–7.17 (3H, m), 7.13–7.06 (3H, m), 6.93 (1H, dt, J=15.8, 6.1 Hz), 6.68 (1H, d, J=7.9 Hz), 6.63 (1H, d, J=15.8 Hz), 3.48 (2H, dd, J=6.1, 1.4 Hz), 3.19 (2H, d, J=7.1 Hz), 2.68 (2H, t, J=7.2 Hz), 2.57–2.49 (4H, m), 2.41 (3H, m), 1.81–1.75 (4H, m), 1.58–1.46 (2H, m), 1.36–1.22 (13H, m) and 0.89 (3H, t, J=6.9 Hz).

(b) N-Nonyl-4-(1H-2-methylimidazo[4,5-c]pyridin-1-ylmethyl)-N-{3-(6-[3-pyrrolidin-1-yl-1-{4-tolyl}-prop-1E-enyl]-pyridin-2-yl)-prop-2E-enyl}-benzamide.

A solution of nonyl-{3-(6-[3-pyrrolidin-1-yl-1-{4-tolyl}-prop-1E-enyl]-pyridin-2-yl)-prop-2E-enyl}-amine (462 mg, 1.0 mmol), 4-(1H-2-methylimidazo[4,5-c]pyridin-1-ylmethyl)benzoic acid sodium salt (349 mg, 1.2 mmol), EDC (288 mg, 1.5 mmol) and HOAt (10 mg) in DMF (10 ml) was stirred at room temperature for 96 hours. Solvent was removed under reduced pressure and the residue partitioned between DCM and brine. The organics were dried over magnesium sulphate, filtered and solvent removed under reduced pressure to leave a brown foam. The product was purified by column chromatography on silica-gel eluting with 15–25% methanol in DCM. Product containing fractions were combined and solvent removed to yield N-nonyl- 4-(1H-2-methylimidazo[4,5-c]pyridin-1-ylmethyl)-N-{3-(6-[3-pyrrolidin-1-yl-1-{4-tolyl}-prop-1E-enyl]-pyridin-2-yl)-prop-2E-enyl}-benzamide as a brown foam (386 mg, 54%). $^1$H-NMR; δ (CDCl$_3$), 9.02 (1H, s), 8.36 (1H, d, J=5.5 Hz), 7.47–7.40 (3H, m), 7.25–6.97 (9H, m), 6.88–6.44 (3H, m), 5.35 (2H, s), 4.40–4.26 (0.8H, m), 4.08–3.99 (1.2H, m), 3.67–3.48 (1.2H, m), 3.31 (2H, d, J=7.0 Hz), 3.30–3.18 (0.8H, m), 2.76–2.60 (4H, bm), 2.58 (3H, s), 2.39 (3H, s), 1.89–1.76 (4H, bm), 1.72–1.04 (14H, m) and 0.85 (3H, t, J=6.6 Hz); $^{13}$C-NMR; δ (CDCl$_3$), 170.8, 157.0, 153.4, 142.9, 142.0, 141.9, 140.3, 139.8, 137.2, 136.9, 136.7, 136.2, 134.9, 132.7, 131.4, 129.6, 129.2, 127.5, 126.2, 121.2, 120.5, 119.9, 104.8, 54.4, 53.8, 50.6,

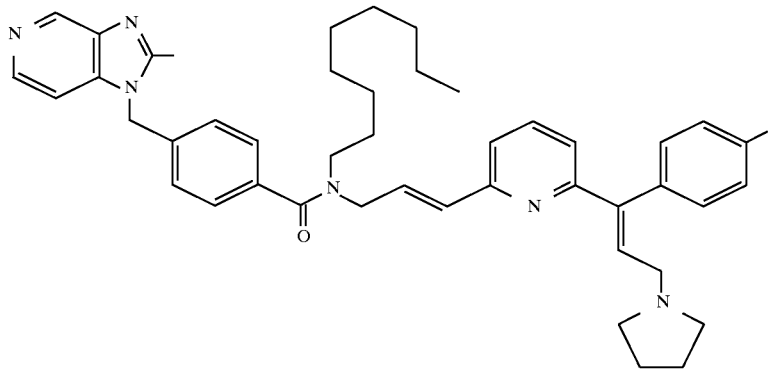

48.6, 47.0, 46.0, 45.2, 31.7, 29.3, 29.1, 28.4, 27.1, 26.9, 26.4, 23.4, 22.6, 21.2 and 14.0.

EXAMPLE 25

N-Hexyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide

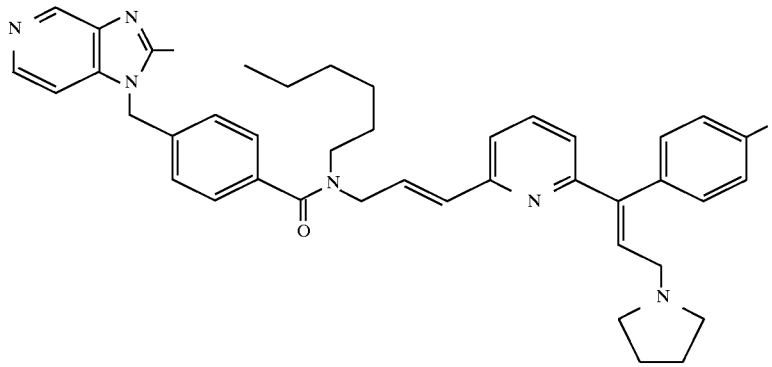

(a) Hexyl-{3-(6-[3-pyrrolidin-1-yl-1-{4-tolyl}-prop-1E-enyl]-pyridin-2-yl)-prop-2E-enyl}-amine.

A solution of 3-(6-[3-pyrrolidin-1-yl-1-{4-tolyl}-prop-1E-enyl]-pyridin-2-yl)-prop-2E-enal (1.11 g, 3.34 mmol) in DCM (50 ml) was treated with magnesium sulphate (5 g) and hexylamine (465 μl, 4.01 mmol). The reaction was stirred for 18 hours, filtered and concentrated under reduced pressure to provide the imine as a green oil. The residue was resuspended in dry methanol (15 ml), cooled in an ice-salt bath and treated under an inert atmosphere with sodium borohydride (131 mg, 3.47 mmol). The reaction was stirred for 2 hours and solvent removed under reduced pressure. The residue was taken up in DCM and washed with saturated sodium bicarbonate. The organics were dried over anhydrous sodium sulphate, filtered and concentrated under reduced pressure to yield hexyl-{3-(6-[3-pyrrolidin-1-yl-1-{4-tolyl}-prop-1E-enyl]-pyridin-2-yl)-prop-2E-enyl}-amine as a brown oil (1.37 g, ~100%). The amine was used directly in the coupling reaction 25(b).

(b) N-Hexyl-4-(1H-2-methylimidazo[4,5-c]pyridin-1-ylmethyl)-N-{3-(6-[3-pyrrolidin-1-yl-1-{4-tolyl}-prop-1E-enyl]-pyridin-2-yl)-prop-2E-enyl}-benzamide.

A solution of hexyl-{3-(6-[3-pyrrolidin-1-yl-1-{4-tolyl}-prop-1E-enyl]-pyridin-2-yl)-prop-2E-enyl}-amine (1.37 g, 3.30 mmol), 4-(1H-2-methylimidazo[4,5-c]pyridin-1-ylmethyl)benzoic acid sodium salt (1.31 g, 3.63 mmol), EDC (949 mg, 4.95 mmol) and HOAt (10 mg) in DMF (15 ml) was stirred at room temperature for 168 hours. Solvent was removed under reduced pressure and the residue partitioned between DCM and brine. The organics were dried over magnesium sulphate, filtered and solvent removed under reduced pressure to leave a brown foam. The product was purified by column chromatography on silica-gel eluting with 20% methanol in DCM. Product containing fractions were combined and solvent removed to yield N-hexyl-4-(1H-2-methylimidazo[4,5-c]pyridin-1-ylmethyl)-N-{3-(6-[3-pyrrolidin-1-yl-1-{4-tolyl}-prop-1E-enyl]-pyridin-2-yl)-prop-2E-enyl}-benzamide as a brown foam (699 mg, 32%). $^1$H-NMR; δ (CDCl$_3$), 9.02 (1H, s), 8.36 (1H, d, J=5.3 Hz), 7.41 (3H, m), 7.19 (4H, m), 7.06 (5H, m), 6.75 (2.5H, m), 6.70 (0.5H, d, J=8.0 Hz), 5.34 (2H, bs), 4.34 (0.8H, bd, J=4.7 Hz), 4.01 (1.2H, bd, J=2.7 Hz), 3.52 (0.8H, bt, J=7.3 Hz), 3.21 (1.2H, m), 3.17 (2H, d, J=6.9 Hz), 2.58 (3H, s), 2.51 (4H, m), 2.38 (3H, s), 1.75 (4H, m), 1.65 (1.2H, m), 1.51 (0.8H, m), 1.20 (6H, m) and 0.85 (3H, m); $^{13}$C-NMR; δ (CDCl$_3$), 170.8, 157.5, 153.5, 153.2, 142.1, 142.0, 141.4, 140.3, 139.8, 136.9, 136.9, 136.6, 136.2, 135.4, 135.3, 133.0, 131.6, 130.7, 129.7, 129.3, 129.1, 127.6, 127.5, 126.2, 121.1, 120.9, 120.3, 119.7, 54.8, 54.2, 50.2, 48.5, 47.0, 46.0, 45.0, 31.6, 31.1, 28.3, 27.1, 26.6, 26.1, 23.5, 22.6, 22.4, 21.3 and 14.0.

EXAMPLE 26

N-Methyl-4-(1H-2-methylimidazo[4,5-c]pyridin-1-yl)-N-{3-[6-(3-pyrrolidin-1-yl-1-{4-tolyl}-prop-1E-enyl)-pyridin-2-yl]-prop-2E-enyl}-benzamide

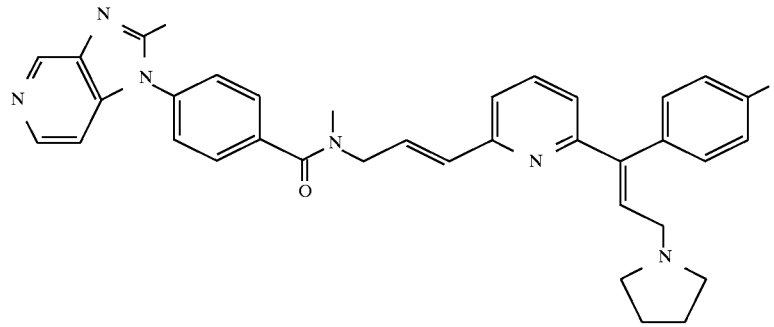

A suspension of 4-(1H-2-methylimidazo[4,5-c]pyridin-1-yl)benzoic acid (WO 9214734, 500 mg, 1.98 mmol) in DCM (15 ml) was treated with EDC (380 mg, 1.98 mmol) and HOBt (270 mg, 1.98 mmol). The reaction was stirred at room temperature for 3 hours. The reaction mixture was partitioned between DCM and brine. The organic layer was separated, dried over magnesium sulphate, filtered and concentrated under vacuum to a colorless oil. The oil was taken up in DMF (10 ml), treated with a solution of methyl-{3-(6-[3-pyrrolidin-1-yl-1-{4-tolyl}-prop-1E-enyl]-pyridin-2-yl)-prop-2E-enyl}-amine (250 mg, 0.72 mmol) also in DMF (2 ml) and stirred at 40° C. for 18 hours. Solvent was removed under reduced pressure and the residue partitioned between DCM and brine. The organics were separated, washed with brine, dried over magnesium sulphate, filtered and solvent removed under reduced pressure to leave a brown oil. The product was purified by column chromatography on silica-gel eluting with 10–14% methanol in DCM. Product containing fractions were combined and solvent removed to yield N-methyl-4-(1H-2-methylimidazo[4,5-c]pyridin-1-yl)-N-{3-[6-(3-pyrrolidin-1-yl-1-{4-tolyl}-prop-1E-enyl)-pyridin-2-yl]-prop-2E-enyl}-benzamide as a white solid (45 mg, 11%). $^1$H-NMR; δ (CDCl$_3$), 9.02 (1H, bs), 8.36 (1H, bs), 7.77 (2H, d, J=6.7 Hz), 7.46–7.37 (3H, m), 7.24–7.21 (3H, m), 7.10–6.90 (5H, m), 6.74–6.59 (2H, m), 4.43 (1H, bs), 4.20 (1H, bs), 3.60 (2H, bs), 3.16 and 3.14 (3H, 2×s), 3.04 (4H, bs), 2.55 (3H, s), 2.39 (3H, s) and 1.98 (4H, bs); $^{13}$H-NMR; δ (CDCl$_3$),170.6, 155.8, 154.1, 152.9, 142.4, 141.7, 140.8, 139.7, 138.0, 137.1, 136.9, 136.0, 133.6, 132.7, 131.3, 129.5, 129.2, 128.7, 126.7, 121.6, 121.3, 120.7, 105.2, 53.7, 53.4, 53.1, 49.1, 37.4, 33.4, 23.2, 21.1 and 14.4.

EXAMPLE 27

(R,S)-4-(1H-2-Methylimidazo[4,5-c]pyridin-1-ylmethyl)benzoic acid (E)-1-[6-(3-pyrrolidin-1-yl-1-{4-tolyl}-prop-1E-enyl)-pyridin-2-yl]hex-1-en-3-yl ester (a) 1-(6-[3-Pyrrolidin-1-yl-1-{4-tolyl}-prop-1E-enyl]-pyridin-2-yl)-hex-1E-en-3-ol.

A stirred solution of 3-(6-[3-pyrrolidin-1-yl-1-{4-tolyl}-prop-1E-enyl]-pyridin-2-yl)-prop-2E-enal (925 mg, 2.78 mmol) in anhydrous THF (30 ml) at −78° C. was treated dropwise with a solution of n-propyl magnesium chloride (1.53 ml, 2.0 M in diethylether, 3.06 mmol). The reaction mixture was allowed to warm slowly to room temperature (~2 hours). The reaction was quenched with water (3 ml) and THF removed under reduced pressure. The residue was taken up in 1M HCl and then basified with solid sodium bicarbonate to pH 8. The product was extracted with ethyl acetate (×3). The organics were combined, dried over sodium sulphate, filtered and concentrated under reduced pressure. The product was purified by column chromatography eluting with 5–8% methanol in DCM. Product containing fractions were combined and solvent removed to provide 1-(6-[3-pyrrolidin-1-yl-1-{4-tolyl}-prop-1E-enyl]-pyridin-2-yl)-hex-1E-en-3-ol as a pale pink foam (593 mg, 57%). $^1$H-NMR; δ (CDCl$_3$), 7.44 (1H, t, J=7.7 Hz), 7.24–7.18 (3H, m), 7.12–7.07 (3H, m), 6.89 (1H, dd, J=15.7, 6.2 Hz), 6.68 (2H, m), 4.38 (1H, m), 3.35 (2H, d, J=7.1 Hz), 2.41 (4H, bs), 1.86 (3H, s), 1.71–1.61 (2H, m), 1.58–1.42 (2H, m), 1.47 (3H, t, J=7.0 Hz).

(b) (R,S)-4-(1H-2-Methylimidazo[4,5-c]pyridin-1-ylmethyl)benzoic acid 1-[6-(3-pyrrolidin-1-yl-1-{4-tolyl}-prop-1E-enyl)-pyridin-2-yl]hex-1E-en-3-yl ester.

A solution of 3-(6-[3-pyrrolidin-1-yl-1-{4-tolyl}-prop-1E-enyl]-pyridin-2-yl)-hex-5E-en-4-ol (300 mg, 0.80 mmol) in DCM (10 ml) was treated with 4-(1H-2-methylimidazo[4,5-c]pyridin-1-ylmethyl)benzoic acid sodium salt (255 mg, 0.88 mmol), EDC (230 mg, 1.20 mmol) and DMAP (20 mg). The reaction mixture was stirred for 96 hours at room temperature. The reaction mixture was partitioned between DCM and saturated sodium bicarbonate solution. The organic layer was separated, dried over magnesium sulphate, filtered and concentrated under reduced pressure. The product was purified by column chromatography eluting with 5–15% methanol/DCM. Product containing fractions were combined and solvent removed to yield (R,S)-4-(1H-2-methylimidazo[4,5-c]pyridin-1-ylmethyl)benzoic acid 1-[6-(3-pyrrolidin-1-yl-1-{4-tolyl}-prop-1E-enyl)-pyridin-2-yl]hex-1E-en-3-yl ester as a brown foam (93 mg, 19%). $^1$H-NMR; δ (CDCl$_3$), 9.04 (1H, s), 8.37 (1H, d, J=5.6 Hz), 8.07 (2H, d, J=8.3 Hz), 7.40 (1H, t, J=7.8 Hz), 7.27–7.02 (9H, bm), 6.91 (1H, dd, J=6.7, 15.6 Hz), 6.68 (2H, m), 5.72 (1H, m), 5.39 (2H, s), 3.18 (2H, d, J=7.1 Hz), 2.59 (3H, s), 2.52 (4H, bs), 2.39 (3H, s), 1.87 (2H, m), 1.76 (4H, bs), 1.47 (2H, m) and 0.96 (3H, t, J=7.3 Hz); $^{13}$C-NMR; δ (CDCl$_3$), 165.1, 157.3, 153.6, 153.4, 142.1, 142.0, 141.6, 140.3, 139.8, 139.7, 136.9, 136.6, 135.4, 132.0, 131.8, 130.7, 130.6, 130.2, 129.7, 129.1, 126.1, 121.1, 120.5, 104.7, 75.0, 54.8, 54.1, 47.1, 36.6, 23.4, 21.2, 18.5, 14.0 and 13.8.

EXAMPLE 28

N-Ethyl-N-{3-[6-(3-pyrrolidin-1-yl-1-{4-tolyl}-prop-1E-enyl)-pyridin-2-yl]-prop-2E-enyl}-3-(1H-2-methylimidazo[4,5-c]pyridin-1-yl)-propylamide

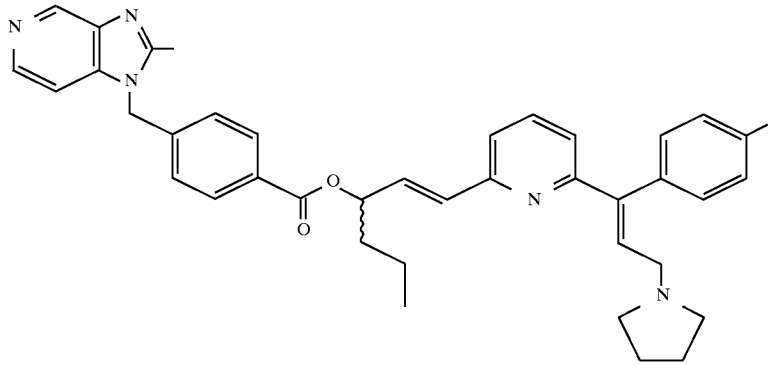

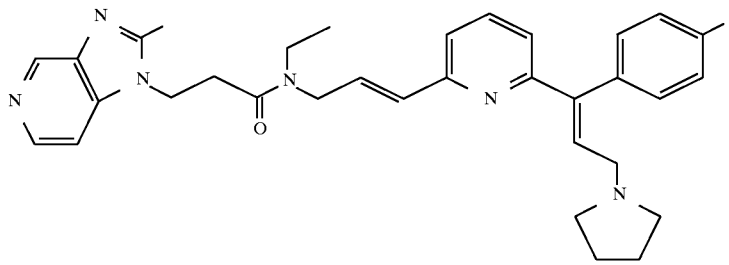

(a) tert-Butyl-3-(1H-2-methylimidazo[4,5-c]pyridin-1-yl)-propanoate.

A solution of 4-chloro-3-nitropyridine (2.94 g, 18.54 mmol) and β-alanine-tert-butyl ester hydrochloride (5.05 g, 27.8 mmol) in DMF (30 ml) was treated with triethylamine (6.5 ml, 46.4 mmol) and stirred at room temperature for 50 hours. The solvent was removed under reduced pressure and residue partitioned between DCM and water. The organic layer was separated, dried over magnesium sulphate, filtered and concentrated under reduced pressure to a dark oil. The residue was dissolved in methanol (50 ml), treated with palladium catalyst (500 mg, 10% on charcoal) and stirred under an atmosphere of hydrogen gas for 24 hours. The catalyst was removed by filtration and solvent removed under reduced pressure. The residue was dissolved in a mixture of acetic acid (50 ml) and acetic anhydride (50 ml). The resulting solution was heated at 140° C. for 28 hours, cooled and concentrated under reduced pressure. The product was purified by column chromatography eluting with 7% methanol in DCM. Product containing fractions were combined and solvent removed to yield tert-butyl-3-(1H-2-methylimidazo[4,5-c]pyridin-1-yl)-propanoate as a pale yellow oil (1.54 g, 32%). $^1$H-NMR; δ (CDCl$_3$), 8.98 (1H, s), 8.42 (1H, d, J=6.9 Hz), 7.38 (1H, d, J=6.7 Hz), 4.41 (2H, t, J=6.8 Hz), 2.73 (2H, t, J=6.7 Hz), 2.70 (3H, s), 1.35 (9H, s).

(b) 3-(1H-2-Methylimidazo[4,5-c]pyridin-1-yl)-propanoic acid.

A solution of tert-butyl-3-(1H-2-methylimidazo[4,5-c]pyridin-1-yl)-propanoate (1.54 g, 5.9 mmol) in trifluoroacetic acid (50 ml) was allowed to stand at room temperature overnight. The reaction mixture was concentrated under reduced pressure to a brown gum. Addition of ethyl acetate gave 3-(1H-2-methylimidazo[4,5-c]pyridin-1-yl)-propanoic acid as a brown solid which was collected by filtration (1.08 g, 89%). $^1$H-NMR; δ (MeOD), 9.15 (1H, s), 8.56 (1H, d, J=6.8 Hz), 8.27 (1H, d, J=6.9 Hz), 4.70 (2H, t, J=7.2 Hz), 2.98 (2H, t, J=7.3 Hz), 2.84 (3H, s).

(c) N-Ethyl-N-{3-[6-(3-pyrrolidin-1-yl-1-{4-tolyl}-prop-1E-enyl]-pyridin-2-yl]-prop-2E-enyl}-3-(1H-2-methylimidazo[4,5-c]pyridin-1-yl)-propylamide.

A solution of ethyl-{3-(6-[3-pyrrolidin-1-yl-1-{4-tolyl}-prop-1E-enyl]-pyridin-2-yl)-prop-2E-enyl}-amine (380 mg, 1.05 mmol), 4-(1H-2-methylimidazo[4,5-c]pyridin-1-yl) propanoic acid (180 mg, 0.86 mmol), EDC (247 mg, 1.29 mmol) and HOAt (10 mg) in DMF (15 ml) was stirred at room temperature for 96 hours. Solvent was removed under reduced pressure and the residue partitioned between DCM and brine. The organics were dried over magnesium sulphate, filtered and solvent removed under reduced pressure to leave a brown foam. The product was purified by column chromatography on silica-gel eluting with 10% methanol and 1% triethylamine in DCM. Product containing fractions were combined and solvent removed to yield N-ethyl-N-{3-[6-(3-pyrrolidin-1-yl-1-{4-tolyl}-prop-1E-enyl)-pyridin-2-yl]-prop-2E-enyl}- 3-(1H-2-methylimidazo [4,5-c]pyridin-1-yl)-propylamide (91 mg, 17%). $^1$H-NMR; δ (MeOD), 8.68 (0.5H, s), 8.56 (0.5H, s), 8.20 (0.5H, d, J=5.9 Hz), 7.98 (0.5H, d, J=5.5 Hz), 7.61 (0.5H, d, J=5.9 Hz), 7.45 (1.5H, m), 7.17 (2H, d, J=8.0 Hz), 7.07 (0.5H, d, J=7.2 Hz), 7.00 (2H, m), 6.90 (1.5H, m), 6.73 (1H, t, J=6.1 Hz), 6.51 (1H, m), 6.36 (0.4H, d, J=15.9 Hz), 6.12 (0.6H, d, J=15.8 Hz), 4.48 (2H, m), 4.02 (2H, m), 3.52 (2H, m), 3.24 (2H, m), 2.93 (6H, m), 2.64 (1.1H, s), 2.60 (1.9H, s), 2.28 (3H, s), 1.82 (4H, m) and 0.95 (3H, m); $^{13}$C-NMR; δ (MeOD), 171.8, 171.5, 158.1, 157.9, 157.0, 157.0, 155.1, 147.1, 147.0, 142.0, 141.8, 141.5, 140.8, 140.7, 139.1, 138.4, 135.6, 132.8, 131.7, 131.2, 130.9, 130.7, 130.5, 124.8, 124.6, 122.6, 122.5, 121.7, 107.7, 54.8, 54.8, 54.6, 50.1, 48.0, 43.6, 42.8, 41.6, 41.5, 33.2, 33.0, 30.7, 24.1, 21.3, 14.2, 13.8 and 13.1.

EXAMPLE 29

N-Cyclohexyl-N-{3-[6-(3-pyrrolidin-1-yl-1-{4-tolyl}-prop-1E-enyl)-pyridin-2-yl]-prop-2E-enyl}-4-(1H-2-methylimidazo[4,5-c]pyridin-1-yl)-butylamide

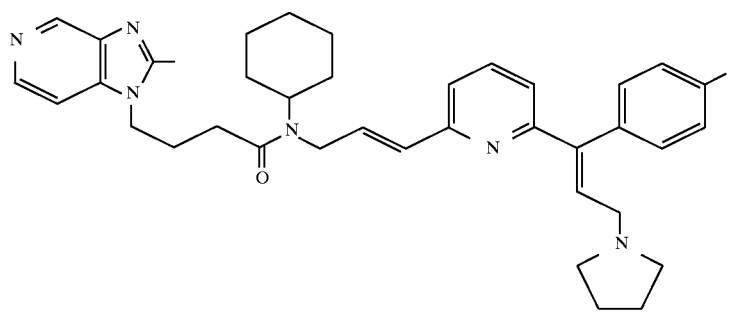

(a) Ethyl-4-(1H-2-methylimidazo[4,5-c]pyridin-1-yl)-butanoate.

Using procedures similar to those described in example 28(a) ethyl-4-aminobutyrate (3.0 g, 17.9 mmol) was used to prepare ethyl-4-(1H-2-methylimidazo[4,5-c]pyridin-1-yl)-butanoate (688 mg, 75%). $^1$H-NMR; δ (CDCl$_3$), 8.98 (1H, s), 8.39 (1H, d, J=5.5Hz), 7.28 (1H, d, J=5.6 Hz), 4.15 (4H, m), 2.65 (3H, s), 2.37 (2H, t, J=6.9 Hz), 2.11 (2H, m), 1.25 (3H, t, J=7.3 Hz).

(b) 4-(1H-2-Methylimidazo[4,5-c]pyridin-1-yl)-butanoic acid sodium salt.

A solution of ethyl-4-(1H-2-methylimidazo[4,5-c]pyridin-1-yl)-butanoate (688 mg, 2.93 mmol) in a mixture of THF and water (4:1, 10 ml) was treated with an aqueous solution of sodium hydroxide (3.04 ml of a 1.01M solution, 3.07 mmol). The reaction was warmed at 40° C. for 18 hours and solvent removed under reduced pressure to yield 4-(1H-2-methylimidazo[4,5-c]pyridin-1-yl)-butanoic acid sodium salt as a pale yellow solid (680 mg, 96%). $^1$H-NMR; δ (MeOD), 8.67 (1H, d, J=0.9 Hz), 8.19 (1H, d, J=5.8 Hz), 7.56 (1H, dd, J=5.5, 0.9 Hz), 4.20 (2H, t, J=7.4 Hz), 2.58 (3H, s), 2.11 (2H, t), 1.96 (2H, s).

(c) N-Cyclohexyl-N-{3-[6-(3-pyrrolidin-1-yl-1-{4-tolyl}-prop-1E-enyl)-pyridin-2-yl]-prop-2E-enyl}-4-(1H-2-methylimidazo[4,5-c]pyridin-1-yl)-butylamide.

A solution of cyclohexyl-{3-(6-[3-pyrrolidin-1-yl-1-{4-tolyl}-prop-1E-enyl]-pyridin-2-yl)-prop-2E-enyl)-amine (990 mg, 2.37 mmol), 4-(1H-2-methylimidazo[4,5-c]pyridin-1-yl)}-butanoic acid sodium salt (680 mg, 2.82 mmol), EDC (681 mg, 3.60 mmol) and HOAt (10 mg) in DMF (15 ml) was stirred at room temperature for 96 hours. Solvent was removed under reduced pressure and the residue partitioned between DCM and brine. The organics were dried over magnesium sulphate, filtered and solvent removed under reduced pressure to leave a brown foam. The product was purified by column chromatography on silica-gel eluting with 5% methanol and 1% triethylamine in DCM. Product containing fractions were combined and solvent removed to yield N-cyclohexyl-N-{3-[6-(3-pyrrolidin-1-yl-1-{4-tolyl}-prop-1E-enyl)-pyridin-2-yl]-prop-2E-enyl}-3-(1H-2-methylimidazo[4,5-c]pyridin-1-yl)-butylamide as an off-white foam (279 mg, 19%). $^1$H-NMR; δ (CDCl$_3$), 8.67 (0.5H, s), 8.61 (0.5H, s), 8.15 (0.5H, d, J=5.7 Hz), 8.11 (0.5H, d, J=5.7 Hz), 7.43 (2H, m), 7.10 (3H, m), 6.94 (2H, d, J=8.1 Hz), 6.85 (0.5H, t, J=6.9 Hz), 6.60 (3.5H, m), 4.26 (1H, t, J=7.3 Hz), 4.17 (1H, t, J=7.4 Hz), 4.01 (2H, m), 3.13 (2H, m), 2.51 (8H, m), 2.25 (3H, s), 2.01 (2H, m) and 1.50 (16H, m); $^{13}$C-NMR; δ (MeOD), 170.2, 169.2, 154.8, 152.7, 152.5, 152.1, 151.2, 140.4, 140.3, 138.0, 137.9, 136.9, 136.4, 134.6, 134.4, 134.2, 132.4, 129.1, 129.0, 128.3, 126.8, 126.2, 125.4, 125.1, 118.2, 118.1, 117.3, 117.0, 103.4, 103.3, 54.6, 51.5, 50.8, 42.0, 40.5, 40.4, 40.4, 40.1, 28.7, 27.6, 27.3, 26.8, 26.4, 23.1, 22.9, 22.3, 22.0, 21.9, 21.2, 9.7 and 9.6.

EXAMPLE 30

N-Cyclohexyl-3-fluoro-4-(1H-2-methylimidazo[4,5-c)pyridin-1-ylmethyl)-N-{3-[6-(3-pyrrolidin-1-yl-1-{4-tolyl}-prop-1E-enyl)-pyridin-2-yl]-prop-2E-enyl}-benzamide

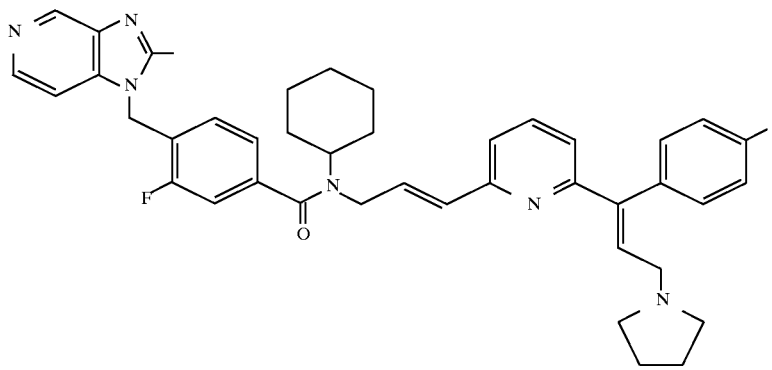

(a) 3-Fluoro-4-(1H-2-methylimidazo[4,5-c]pyridin-1-ylmethyl)benzoic acid sodium salt.

3-Fluoro-4-(1H-2-methylimidazo[4,5-c]pyridin-1-ylmethyl)benzoic acid sodium salt was prepared using chemistry similar to that reported in the literature for 4-(1H-2-methylimidazo[4,5-c]pyridin-1-ylmethyl)benzoic acid sodium salt. $^1$H-NMR; δ (MeOD), 8.71 (1H, d. J=0.79 Hz), 8.18 (1H, d, J=5.8 Hz), 7.62–7.53 (2H, m), 7.43 (1H, d, J=5.5 Hz), 6.97 (1H, t, J=7.7 Hz), 5.49 (2H, s), 2.56 (3H, s).

(b) N-Cyclohexyl-3-fluoro-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide.

A solution of cyclohexyl-{3-(6-[3-pyrrolidino-1-{4-tolyl}-prop-1E-enyl]-pyridin-2-yl)-prop-2-enyl}-amine (1.13 g, 2.72 mmol), 4-(1H-2-methylimidazo[4,5-c]pyridin-1-ylmethyl)benzoic acid sodium salt (920 mg, 3.00 mmol), EDC (780 mg, 4.08 mmol) and HOAt (370 mg, 2.72 mmol) in DMF (1 5 ml) was stirred at room temperature for 96 hours. Solvent was removed under reduced pressure and the residue partitioned between DCM and brine. The organics were dried over magnesium sulphate, filtered and solvent removed under reduced pressure to leave a brown foam. The product was purified by column chromatography on silica-gel eluting with 5–15% methanol in DCM. Product containing fractions were combined and solvent removed to yield N-cyclohexyl-3-fluoro-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide as a pale brown foam (747 mg, 40%). $^1$H-NMR; δ (CDCl$_3$), 9.03 (1H, s), 8.39 (1H, d, J=5.6 Hz), 7.43 (1H, t, J=7.8 Hz), 7.27–7.07 (9H, m), 6.78 (4H, m), 5.39 (2H, s), 4.23 (2.3H, m), 3.98 (0.7H, m), 3.26 (2H, d, J=6.7 Hz), 2.64 (7H, bs), 2.40 (3H, s), 1.80 (4H, bs) and 1.62–1.06 (10H, bm); $^{13}$C-NMR; δ (CDCl$_3$), 161.8, 157.8, 157.1, 153.4, 142.0, 141.9, 140.1, 139.7, 136.9, 136.5, 135.0, 131.8, 131.3, 130.6, 129.6, 129.0, 128.2, 123.2, 123.0, 122.6, 120.8, 119.7, 114.5, 114.1, 104.7, 59.1, 54.9, 54.4, 53.8, 50.4, 47.2, 43.2, 41.3, 41.2, 31.8, 30.6, 25.6, 24.9, 23.4 and 13.8.

EXAMPLE 31

N-Cyclohexyl-3-methoxy-4-(1H-2-methylimidazo[4, 5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide

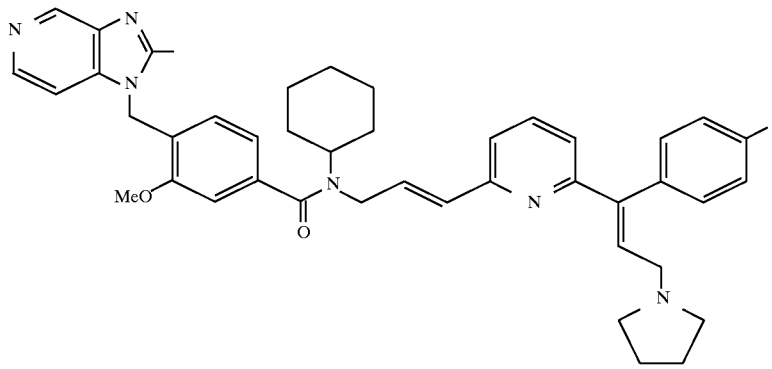

(a) 3-Methoxy-4-(1H-2-methylimidazo[4,5-c]pyridin-1-ylmethyl)benzoic acid sodium salt.

3-Methoxy-4-(1H-2-methylimidazo[4,5-c]pyridin-1-ylmethyl)benzoic acid sodium salt was prepared using chemistry similar to that reported in the literature for 4-(1H-2-methylimidazo[4,5-c]pyridin-1-ylmethyl)benzoic acid sodium salt. $^1$H-NMR; δ (MeOD), 7.99 (1H, d, J=0.8 Hz), 7.45 (1H, d, J=5.8 Hz), 6.80 (1H, d, J=1.3 Hz), 6.73–6.67 (2H, m), 6.19 (1H, d, J=7.8 Hz), 4.06 (3H, s), 3.03 (3H, s).
(b) N-Cyclohexyl-3-methoxy-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide.

A solution of cyclohexyl-{3-(6-[3-pyrrolidino-1-{4-tolyl}-prop-1E-enyl]-pyridin-2-yl)-prop-2E-enyl}-amine (1.05 g, 2.53 mmol), 4-(1H-2-methylimidazo[4,5-c]pyridin-1-ylmethyl)benzoic acid sodium salt (890 mg, 2.78 mmol), EDC (730 mg, 3.80 mmol) and HOAt (340 mg, 2.53 mmol) in DMF (15 ml) was stirred at room temperature for 48 hours. Solvent was removed under reduced pressure and the residue partitioned between DCM and brine. The organics were dried over magnesium sulphate, filtered and solvent removed under reduced pressure to leave a brown foam. The product was purified by column chromatography on silica-gel eluting with 5–15% methanol in DCM. Product containing fractions were combined and solvent removed to yield N-cyclohexyl-3-fluoro-4-(1H-2-methylimidazo[4,5-c]pyridin-1-ylmethyl)-N-{3-(6-[3-pyrrolidino-1-{4-tolyl}-prop-1E-enyl]-pyridin-2-yl)-prop-2E-enyl}-benzamide as a pale brown foam (646 mg, 37%). $^1$H-NMR; δ (CDCl$_3$), 9.00 (1H, s), 8.34 (1H, d, J=5.5 Hz), 7.42 (1H, t, J=7.8 Hz), 7.22 –6.70 (13H, m), 5.31 (2H, bs), 4.23–3.56 (6H, bm), 3.30 (2H, d, J=6.2 Hz), 2.67 (4H, bs), 2.60 (3H, s), 2.39 (3H, s) and 1.82–1.06 (14H, m); 156.7, 153.9, 141.7, 140.5, 139.8, 137.2, 136.6, 134.8, 131.7, 131.2, 129.5, 129.2, 127.2, 124.0, 120.9, 119.9, 118.3, 109.1, 105.1, 55.5, 54.1, 53.6, 42.9, 32.0, 25.7, 23.4, 21.1 and 13.9.

Pharmacology Example 1
Inhibition of [$^3$H]-Pyrilamine Binding to Histamine-1 Receptors on Hela-S3 Cells The inhibition of [$^3$H]-pyrilamine binding to histamine-1 receptors on Hela-S3 cells (American Type Culture Collection) was determined by isotopic labelling and filtration techniques. A suspension of the cells in buffer (25 ml, 0.5% Bovine Serum Albumin, 0.1% sodium azide, phosphate buffered saline (PBS)) was centrifuged at 1000 rpm for 5 minutes in a JOUAN CR 422 centrifuge, collected, resuspended in buffer (25 ml) and spun again. The cells were counted using a haemocytometer and resuspended in buffer to provide a final concentration of $4.5 \times 10^6$ cells ml$^{-1}$. A portion of the Hela-S3 cell suspension (1 ml) was added to each assay tube containing 25 μl of vehicle (50% DMSO/buffer) or 25 μl of test compound solution (dissolved in DMSO and diluted with sufficient PBS to give a final test concentration of 1 μM) and 25 μl of [$^3$H]-pyrilamine (supplied by Amersham International and diluted with PBS to 3 nM). The tubes were mixed, incubated at 37° C. for 30 minutes and then spun at 4° C. at 2000 rpm for 2 minutes. The supernatant was removed and the cells resuspended in buffer (repeated x2). The cells were suspended in 300 μl of a 2:1 solution of 1M sodium hydroxide and 1% sodium dodecyl sulphate. The tubes were left overnight before the contents were tranferred to a scintillation vial, treated with 10 ml, OPTIPHASE MP scintillation fluid (OPTIPHASE MP is a trade mark) and the radioactivity counted in a scintillation counter. Non-displacable binding (NDB) was determined using Astemizole ($5 \times 10^{-5}$M) in place of test compounds. Defining the counts for total binding from the vehicle control sample as "TB" and the counts for total binding with antogonist as "TBA" the percentage specific binding (% SB) can be determined from the following equation.

$$\% \text{ SB} = \frac{(\text{TBA} - \text{NDB})}{(\text{TB} - \text{NDB})} \times 100\%$$

Results

| Example | % Specific Binding at 1 μM |
|---------|----------------------------|
| 1       | 16                         |
| 2       | 15                         |
| 3       | 19                         |
| 4       | 42                         |
| 5       | 16                         |
| 6       | 29                         |
| 7       | 40                         |
| 8       | 34                         |
| 9       | 63                         |
| 10      | 62                         |
| 11      | 60                         |

-continued $$\% \text{ SB} = \frac{(TBA - NDB)}{(TB - NDB)} \times 100\%$$

Results

| Example | % Specific Binding at 1 μM |
|---------|---------------------------|
| 12 | 64 |
| 13 | 30 |
| 16 | 30 |
| 17 | 58 |
| 22 | 31 |
| 26 | 26 |

Pharmacology Example 2

Inhibition of PAF-Induced Platelet Aggregation

Male New Zealand White rabbits (3.0–3.5 kg) were anaesthetised by intravenous administration of sodium pentobarbitone, 18 mg.ml$^{-1}$, via a marginal ear vein. The trachea was exposed and connected to a respiratory pump (Harvard UK) to provide artificial ventilation. A carotid artery was exposed and cannulated and the animal was exsanguinated. Whole blood was collected in a syringe containing tri-sodium citrate (3.8% w/v) to a ratio of 1 part citrate:9 parts blood.

Collected blood was centrifuged at 180×g for 15 minutes at room temperature (21° C.) to prepare platelet-rich plasma (PRP). The remaining blood was then centrifuged at 1800×g for 10 minutes at room temperature to obtain platelet poor plasma (PPP).

Platelet count of the PRP was measured using a Technicon H1 blood cell differential analyser (Bayer Diagnostics UK) and adjusted with PPP to obtain a final platelet count of 500,000 platelets per μl of plasma, this being the normal physiological platelet count for rabbits. Corrected PRP was left to equilibrate at room temperature for 30 minutes before use.

Aggregation studies were carried out using a 4-channel aggregometer (PAP-4C, BioData USA) as follows: 400 μl aliquots of PRP were placed in siliconised cuvettes and incubated to 37° C. for 1 to 2 minutes in the heating block of the aggregometer. Baseline (100% aggregation) was set up using PPP (500 μl in a siliconised cuvette). The PRP was placed into a measuring well of the aggregometer, and a stirrer bar was added. The sample was stirred at 1000 rpm. The machine was activated to set the 0% aggregation level. Test compound or vehicle (50 μl) was added to the PRP, where any effects on the baseline was noted. PAF (100 ngml$^{-1}$ as 50 μl aliqout) was added to the PRP 3 minutes after test compound or vehicle. Aggregation was measured for a further 4 minutes after PAF addition and the maximum aggregation over the 4 minutes was recorded.

The investigation of different concentrations of test compound was performed in triplicate. Data were expressed as 0% aggregation of the sample and test compound data were compared to vehicle data to obtain % inhibition of the PAF-induced aggregation from which IC$_{50}$ values could be determined.

PAF was made up in sterile saline (NaCl 0.9% w/v) containing BSA (0.25% w/v) from an initial stock solution (10 mgml$^{-1}$ in EtOH). Test compounds were made up as 1×10$^{-3}$M stock solutions in sterile saline containing molar equivalents of 1N HCl (v/v) or in DMSO.

In the results which follow, a comparison compound A was included. Compound A was prepared as described in EP-A-260613 (G. D. Searle), but is not part of the present invention. As appears from the results of the comparison, compounds of this invention, all of which incorporate a fragment capable of H$_1$ antagonist activity, are observed to show improved PAF antagonist activity over compound A.

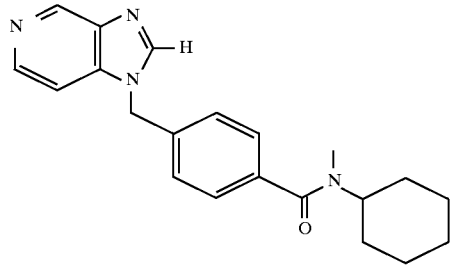

Results

| Example | PAF-Induced Platelet Aggregation IC$_{50}$ (nM) |
|---------|------------------------------------------------|
| 1 | 2100 |
| 2 | 542 |
| 3 | 1480 |
| 4 | 167 |
| 5 | 2200 |
| 6 | 333 |
| 7 | 133 |
| 8 | 92 |
| 9 | 43 |
| 10 | 2010 |
| 11 | 176 |
| 12 | 58 |
| 13 | 238 |
| 16 | 130 |
| 17 | 315 |
| 22 | 62 |
| Compound A | 74000 |

Pharmacology Example 3

Histamine Induced Bronchoconstriction in the Anaesthetised Guinea Pig

Following oral administration of test compound or vehicle by oral gavage, male Dunkin-Hartley guinea pigs (350–400 g) were anaesthetised by intraperitoneal injection of 60 mgkg$^{-1}$ sodium pentobarbitone (Sagatal, May & Baker UK). Through a midline incision of the neck, the trachea was cannulated and connected to a small animal respirator (Harvard, UK). Animals were artificially ventilated at a rate of 30 breaths per minute with a tidal volume of 8–10 ml to give a resting tracheal inflation pressure of 15 mmHg as measured by a physiological pressure transducer (type P23XL, Spectramed USA) connected to a side arm of the respiratory circuit.

A jugular vein was cannulated for the administration of propranolol and for the infusion of histamine. A carotid artery was cannulated for the measurement of arterial blood pressure via a physiological pressure transducer (type P23XL, Spectramed USA). Blood pressure and tracheal inflation pressure were recorded on a thermal array chart recorder (type TA4000, Gould Electronics UK).

Following a suitable equilibration period, propranolol (1 mgkg$^{-1}$ i.v. & 3 mgkg$^{-1}$ s.c. Sigma Chemical Co. UK) was administered to inhibit any resulting catecholamine release following histamine administration.

Histamine infusion (10 μgkg$^{-1}$min$^{-1}$ at a rate of 10 mlhr$^{-1}$ using a perfusion pump type Perfuser securer FT, B. Braun Germany) was started at the one hour time point following oral administration of the test compound or vehicle.

Changes in tracheal inflation pressure and blood pressure of drug treated animals were compared with changes from vehicle treated animals and $ED_{50}$ values determined. One dose of test compound was investigated per animal.

| Example | Results $ED_{50}$ mg kg$^{-1}$, p.o. or % inhibition |
|---|---|
| 3 | 0.40 |
| 4 | 0.85 |
| 13 | 1.00 |
| 16 | 46% at 10 mg/kg |
| 20 | 1.00 |

Pharmacology Example 4

PAF Induced Bronoconstriction in the Anaesthetised Guinea Pig

Following oral administration of test compound or vehicle, male Dunkin-Hartley guinea pigs (350–400 g) were anaesthetised by intraperitoneal injection of 60 mgkg$^{-1}$ sodium pentobarbitone (Sagatal, May & Baker UK). Through a midline incision of the neck, the trachea was cannulated and connected to a small animal respirator (Harvard, UK) Animals were artificially ventilated at a rate of 30 breaths per minute with a tidal of of 8–10 ml to give a resting tracheal inflation pressure of 15 mmHg as measured by a physiological pressure transducer (type P23XL, Spectramed USA) connected to a side arm of the respiratory circuit.

A jugular vein was cannulated for the administration of a bolus dose of propranolol and for the later administration of bolus PAF. A carotid artery was cannulated for the measurement of arterial blood pressure via a physiological pressure transducer (type P23XL, Spectramed USA). Blood pressure and tracheal inflation pressure were recorded on a thermal array chart recorder (type TA4000, Gould Electronics UK).

Propranolol (1 mgkg$^{-1}$ i.v. & 3 mgkg$^{-1}$ s.c. Sigma Chemical Co. UK) was administered 10 minutes before PAF in order to prevent the bronchodilatory activity of catecholamines which may be released in response to PAF administration. PAF (100 ngkg$^{-1}$ i.v. bolus) was administered at the one hour time point following oral administration of the test compound or vehicle.

Changes in tracheal inflation pressure and blood pressure of drug treated animals were compared with changes from vehicle treated animals and percentage inhibition determined. One dose of test compound was investigated per animal.

| Example | Results $ED_{50}$ mg kg$^{-1}$, p.o. |
|---|---|
| 3 | 5.8 |
| 4 | 1.55 |
| 13 | 2.55 |
| 16 | 1.55 |
| 20 | 4.20 |

What is claimed is:

1. A compound of formula (II)

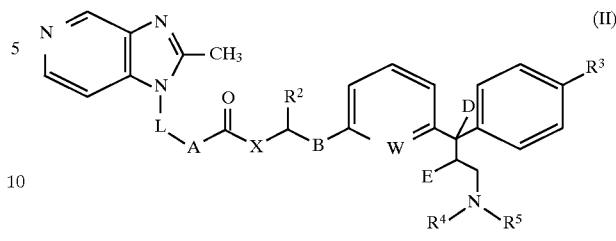

wherein:
L and A are such that (i) L represents an unbranched saturated or unsaturated divalent hydrocarbon chain having up to 6 carbon atoms and A represents a bond, or (ii) L represents a bond or —CH$_2$— and A represents a divalent 1,4-phenylene group which may be substituted by $C_1$-$C_6$ alkyl, $C_2$-$C_6$ alkenyl, cyano, halogen or $C_1$-$C_6$ alkoxy;

X represents (a) —O—; or (b) —N(R$^1$)— wherein R$^1$ represents hydrogen, $C_1$-$C_6$ alkyl, $C_2$-$C_6$ alkenyl, $C_2$-$C_6$ alkynyl, $C_3$-$C_8$ cycloalkyl or non-aromatic saturated heterocyclic monocyclic group having from 5 to 7 ring atoms wherein the heteroatom is selected from O, any of which may be substituted with one or more $C_1$-$C_6$ alkyl, —(C═O)O($C_1$-$C_6$ alkyl), —COOH, or phenyl groups;

R$^2$ represents hydrogen, or $C_1$-$C_6$ alkyl;

B represents a bond, or a straight or branched saturated or unsaturated divalent hydrocarbon chain of up to 2 carbon atoms;

R$^3$ represents hydrogen, $C_1$-$C_4$ alkyl, halogen, cyano, trifluoromethyl or $C_1$-$C_4$ alkoxy;

W represents —N═;

D and E taken together represent a bond;

R$^4$ and R$^5$ together with the nitrogen atom to which they are attached form a pyrrolidino ring;

or a pharmaceutically or veterinarily acceptable acid addition salt, solvate or hydrate thereof.

2. A compound as claimed in claim 1 wherein L is —CH$_2$— and A is 1,4-phenylene, 3-fluoro-1,4-phenylene or 3-methoxy-1,4-phenylene.

3. A compound as claimed in claim 1, wherein X represents —N(R$^1$)— wherein R$^1$ represents hydrogen, cyclopropyl, cyclopentyl, 3,5-dimethylcyclohex-1-yl, 3-methylbut-1-yl, n-butyl, iso-butyl, sec-butyl, tert-butyl, n-propyl, isopropyl, n-pentyl, 2-ethylcarboxylate-3-methylbut-1-yl, benzyl, or tetrahydropyranyl.

4. A compound as claimed in claim 1 wherein X represents —N(R$^1$)— wherein R$^1$ represents cyclohexyl, methyl or ethyl.

5. A compound as claimed in claim 1, wherein R$^2$ represents hydrogen.

6. A compound as claimed in claim 1 wherein B represents —CH$_2$CH$_2$—.

7. A compound as claimed in any one of claims 1 to 6 wherein B represents —CH═CH— (trans).

8. A compound as claimed in claim 1, wherein R$^3$ represents hydrogen, $C_1$-$C_4$ alkyl, or halogen.

9. A compound as claimed in claim 1, wherein R$^3$ represents methyl.

10. A compound as claimed in claim 1 wherein L is —CH$_2$— and A is 1,4-phenylene, 3-fluoro-1,4-phenylene or 3-methoxy-1,4-phenylene; X represents —N(R$^1$)— wherein R$^1$ is cyclohexyl, methyl or ethyl; R$^2$ is hydrogen; B is —CH=CH— (trans); R³ is methyl; W is —N=; D and E taken together represent a bond; and R⁴ and R⁵ together with the nitrogen atom to which they are attached form a pyrrolidino ring, or a pharmaceutically or veterinarily acceptable acid addition salt, solvate or hydrate thereof.

11. N-Cyclohexyl-4-(1H-2-methylimidazo[4,5-c]pyridin-1-ylmethyl)-N-(E)-{3-[6-(3-pyrrolidin-1-yl-1-{4-tolyl}-prop-1E-enyl)-pyridin-2-yl]-prop-2-enyl}-benzamide, or a pharmaceutically or veterinarily acceptable acid addition salt, solvate or hydrate thereof.

12. N-Ethyl-4-(1H-2-methylimidazo[4,5-c]pyridin-1-ylmethyl)-N-(E)-{3-[6-(3-pyrrolidin-1-yl-1-{4-tolyl}-prop-1E-enyl)-pyridin-2-yl]-prop-2-enyl}-benzamide, or a pharmaceutically or veterinarily acceptable acid addition salt, solvate or hydrate thereof.

13. A compound selected from the group consisting of:

4-(1H-2-Methylimidazo[4,5-c]pyridin-1-ylmethyl) benzoic acid 3-[6-(3-pyrrolidin-1-yl-1-{4-tolyl}-prop-1E-enyl)-pyridin-2-yl]prop-2E-enyl ester, 4-(1H-2-Methylimidazo[4,5-c]pyridin-1-ylmethyl) benzoic acid 3-[6-(3-pyrrolidin-1-yl-1-{4-tolyl}-prop-1E-enyl)-pyridin-2-yl]propyl ester, N-Methyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, 4-(1H-2-Methylimidazo[4,5-c]pyridin-1-ylmethyl)-N-{3-[6-(3-pyrrolidino-1-{4-tolyl}-prop-1E-enyl)-pyridin-2-yl]-prop-2E-enyl}-benzamide, N-(3-Methyl-but-1-yl)-4-(1H-2-methylimidazo[4,5-c]pyridin-1-ylmethyl)-N-{3-[6-(3-pyrrolidin-1-yl-1-{4-tolyl}-prop-1E-enyl)-pyridin- 2-yl]-prop-2E-enyl}-benzamide, N-iso-Butyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Cyclopentyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-(R,S) sec-Butyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-tert-Butyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-3,5-Dimethylcyclohexyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-iso-Propyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, (S)-4-Methyl-2-([4-(1H-2-methylimidazo[4,5-c]pyridin-1-ylmethyl)-benzoyl]-{3-[6-(3-pyrrolidin-1-yl-1-{4-tolyl}-prop-1E-enyl)-pyridin-2-yl]-prop-2E-enyl}-amino)-pentanoic acid ethyl ester, N-Benzyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Propyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Cyclohexyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-propyl}-benzamide, N-Cyclopropyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, (R,S)-4-(1H-2-Methylimidazo[4,5-c]pyridin-1-ylmethyl) benzoic acid 3-[6-(3-pyrrolidin-1-yl-1-{4-tolyl}-prop-1E-enyl)-pyridin-2-yl]but-3E-en-2-yl ester, N-Cyclohexyl-4-(1H-2-methylimidazo[4,5-c]pyridin-1-ylmethyl)-N-{3-[6-(3-pyrrolidin-1-yl-1-{4-p-chlorophenyl}-prop-1E-enyl)-pyridin-2-yl]-prop-2E-enyl}-benzamide, N-4-Tetrahydropyranyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Butyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Pentyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Nonyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Hexyl-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Methyl-4-(1H-2-methylimidazo[4,5-c]pyridin-1-yl)-N-{3-[6-(3-pyrrolidin-1-yl-1-{4-tolyl}-prop-1E-enyl)-pyridin-2-yl]-prop-2E-enyl}-benzamide, (R,S)-4-(1H-2-Methylimidazo[4,5-c]pyridin-1-ylmethyl) benzoic acid (E)-1-[6-(3-pyrrolidin-1-yl-1-{4-tolyl}-prop-1E-enyl)-pyridin-2-yl]hex-1E-en-3-yl ester, N-Ethyl-N-{3-[6-(3-pyrrolidin-1-yl-1-{4-tolyl}-prop-1E-enyl)-pyridin-2-yl]-prop-2E-enyl}-3-(1H-2-methylimidazo[4,5-c]pyridin-1-yl)-propylamide, N-Cyclohexyl-N-{3-[6-(3-pyrrolidin-1-yl-1-{4-tolyl}-prop-1E-enyl)-pyridin-2-yl]-prop-2E-enyl}-4-(1H-2-methylimidazo[4,5-c]pyridin-1-yl)-butylamide N-Cyclohexyl-3-fluoro-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, N-Cyclohexyl-3-methoxy-4-(1H-2-methylimidazo[4,5-c]pyridin-1-ylmethyl)-N-{3-[6-(3-pyrrolidin-1-yl-1-{4-tolyl}-prop-1E-enyl)-pyridin-2-yl]-prop-2E-enyl}-benzamide, and their pharmaceutically or vererinarily acceptable salts, hydrates and solvates.

14. A pharmaceutical or veterinary composition comprising a compound as claimed in claim 1, together with a pharmaceutically or veterinarily acceptable carrier.

15. A composition as claimed in claim 14 which is adapted for oral administration.

16. A method of treating diseases or conditions mediated by histamine and/or PAF in mammals which method comprises administering to the mammal an effective amount of a compound as claimed in claim 1.

17. A method as claimed in claim 16, wherein the disease or condition referred to is hypotension, thrombocytopenia, bronchoconstriction, circulatory shock, increased vascular permeability (oedema/erythema), allergic rhinitis, sinusitis, asthma, dermatitis, psoriasis, urticaria, anaphylactic shock, conjunctivitis, pruritis, inflammatory bowel disease or colitis.

* * * * *